US010575808B2

(12) United States Patent  (10) Patent No.: US 10,575,808 B2
Zan  (45) Date of Patent: *Mar. 3, 2020

(54) INTEGRATED MULTI-RAIL IMAGING SYSTEM

(71) Applicant: FUJIFILM SonoSite, Inc., Bothell, WA (US)

(72) Inventor: Leo Zan, Toronto (CA)

(73) Assignee: FUJIFILM SONOSITE, INC., Bothell, WA (US)

( * ) Notice: Subject to any disclaimer, the term of this patent is extended or adjusted under 35 U.S.C. 154(b) by 699 days.

This patent is subject to a terminal disclaimer.

(21) Appl. No.: 15/288,752

(22) Filed: Oct. 7, 2016

(65) Prior Publication Data

US 2017/0095220 A1  Apr. 6, 2017

Related U.S. Application Data

(63) Continuation of application No. 14/576,113, filed on Dec. 18, 2014, now Pat. No. 9,474,498, which is a (Continued)

(51) Int. Cl.
*A61B 6/00* (2006.01)
*A61B 5/055* (2006.01)
(Continued)

(52) U.S. Cl.
CPC ............ *A61B 6/508* (2013.01); *A61B 5/0555* (2013.01); *A61B 6/032* (2013.01); *A61B 6/0457* (2013.01);
(Continued)

(58) Field of Classification Search
CPC ... A61B 8/0833; A61B 8/0841; A61B 8/4209; A61B 5/0555; A61B 6/508; A61B 6/032;
(Continued)

(56) References Cited

U.S. PATENT DOCUMENTS 1,573,571 A   2/1926 Pohl
1,599,134 A   9/1926 King
(Continued)

FOREIGN PATENT DOCUMENTS

FR   2670097 A1   6/1992
JP   55003740 Y2   1/1980
(Continued)

OTHER PUBLICATIONS

Foster, F.S. et al. "A new ultrasound instrument for in vivo microimaging of mice," *Ultrasound in Medicine & Biology*, vol. 28, Issue 9, Sep. 2002, pp. 1165-1172.
(Continued)

*Primary Examiner* — Oommen Jacob
(74) *Attorney, Agent, or Firm* — Baker Botts L.L.P.

(57) ABSTRACT

The imaging system can comprise a plurality of elongated rails, a scanhead assembly, and a small animal mount assembly. The scanhead assembly is selectively mounted onto a first rail and is constructed and arranged for movement in a linear bi-directional manner along the longitudinal axis of the first rail. The small-animal mount assembly is selectively mounted onto a second rail and is constructed and arranged for movement in a linear bi-directional manner along the longitudinal axis of the second rail. The second rail being mounted relative to the first rail such that the longitudinal axis of the second rail is at an angle to the longitudinal axis of the first rail. The imaging system can also comprise a needle injection assembly that is selectively mounted onto the third rail and is constructed and arranged for movement in a linear bi-directional manner along the longitudinal axis of the third rail. The third rail being mounted relative to the second rail and the first rail such that the longitudinal axis of the third rail is substantially coaxial to the longitudinal axis of the first rail. Alternatively, the
(Continued)

needle injection assembly is mounted onto the first rail, such that the second rail is positioned therebetween the needle injection assembly and the scanhead assembly.

18 Claims, 67 Drawing Sheets

Related U.S. Application Data continuation of application No. 13/324,996, filed on Dec. 13, 2011, now Pat. No. 8,945,014, which is a continuation of application No. 11/053,748, filed on Feb. 7, 2005, now Pat. No. 8,078,256, which is a continuation-in-part of application No. 10/683,168, filed on Oct. 10, 2003, now Pat. No. 7,133,713.

(60) Provisional application No. 60/417,167, filed on Oct. 10, 2002, provisional application No. 60/468,959, filed on May 9, 2003, provisional application No. 60/468,960, filed on May 9, 2003.

(51) Int. Cl.
*A61D 3/00* (2006.01)
*A61B 8/08* (2006.01)
*A61B 90/11* (2016.01)
*A61B 8/00* (2006.01)
*A61B 6/03* (2006.01)
*A61B 6/04* (2006.01)
*A61B 6/12* (2006.01)

(52) U.S. Cl.
CPC .............. *A61B 6/44* (2013.01); *A61B 8/0833* (2013.01); *A61B 8/0841* (2013.01); *A61B 8/40* (2013.01); *A61B 8/4209* (2013.01); *A61B 8/4461* (2013.01); *A61B 90/11* (2016.02); *A61D 3/00* (2013.01); *A61B 6/12* (2013.01)

(58) Field of Classification Search
CPC ........... A61B 6/0457; A61B 6/44; A61B 8/40; A61B 8/4461; A61B 90/11; A61B 6/00; A61D 3/00
USPC .......................................... 600/459, 437, 407
See application file for complete search history.

(56) References Cited

U.S. PATENT DOCUMENTS

| | | | |
|---|---|---|---|
| 2,789,538 A | 4/1957 | Merritt | |
| 2,828,172 A | 3/1958 | McDonald | |
| 3,028,836 A | 4/1962 | Strauss | |
| 3,120,836 A | 2/1964 | Brauning | |
| 3,327,656 A | 6/1967 | Schwartz | |
| 3,474,763 A | 10/1969 | Kissil et al. | |
| 3,476,104 A | 11/1969 | Davis | |
| 3,589,257 A * | 6/1971 | Horiuchi | G03B 35/04 396/324 |
| 3,628,015 A * | 12/1971 | Franks | G01N 23/2076 250/374 |
| 3,685,779 A | 8/1972 | Papritz | |
| 3,720,209 A | 3/1973 | Bolduc | |
| 3,888,240 A | 6/1975 | Reinhold, Jr. et al. | |
| 3,955,788 A * | 5/1976 | Delage | B01L 9/00 248/228.3 |
| 3,970,046 A | 7/1976 | Boggs | |
| 4,033,539 A * | 7/1977 | Bardocz | G01M 11/04 248/228.6 |
| 4,082,086 A | 4/1978 | Page et al. | |
| 4,148,280 A | 4/1979 | Masuda et al. | |
| 4,177,967 A * | 12/1979 | Marchus | F16M 11/126 248/229.1 |
| 4,181,297 A * | 1/1980 | Nichols | A61F 5/3761 128/878 |
| 4,184,451 A * | 1/1980 | Carlin | A61D 3/00 119/755 |
| 4,257,349 A | 3/1981 | Carlin | |
| 4,363,128 A * | 12/1982 | Grady | A61B 6/4441 378/181 |
| 4,365,561 A | 12/1982 | Roneo | |
| 4,672,697 A | 6/1987 | Schuerch | |
| 4,727,564 A * | 2/1988 | Mekker | A61B 6/4283 378/176 |
| 4,779,540 A | 10/1988 | Dion | |
| 4,842,259 A | 6/1989 | Rice | |
| 5,014,292 A * | 5/1991 | Siczek | A61B 6/00 378/195 |
| 5,020,520 A | 6/1991 | Lawlis | |
| 5,022,762 A | 6/1991 | Stroud et al. | |
| 5,023,899 A * | 6/1991 | Ohlson | A61B 6/022 378/177 |
| 5,104,621 A | 4/1992 | Pfost et al. | |
| 5,138,138 A | 8/1992 | Theilacker et al. | |
| 5,163,380 A | 11/1992 | Duffy et al. | |
| 5,168,634 A | 12/1992 | Misevich | |
| 5,279,309 A * | 1/1994 | Taylor | A61B 34/20 600/595 |
| 5,309,847 A | 5/1994 | Matsumoto | |
| 5,324,911 A | 6/1994 | Cranston et al. | |
| 5,386,453 A * | 1/1995 | Harrawood | A61B 6/0442 378/193 |
| 5,615,854 A * | 4/1997 | Nomura | F16M 11/10 248/205.3 |
| 5,642,432 A * | 6/1997 | Mori | G01R 1/06705 382/145 |
| 5,732,912 A * | 3/1998 | Nomura | F16C 11/103 248/187.1 |
| 5,826,286 A | 10/1998 | Cranston | |
| 5,915,334 A | 6/1999 | Cummings et al. | |
| 5,976,156 A * | 11/1999 | Taylor | A61B 34/20 606/130 |
| 5,985,214 A | 11/1999 | Stylli et al. | |
| 6,001,309 A | 12/1999 | Gamble et al. | |
| 6,094,760 A * | 8/2000 | Nonaka | A61B 6/0457 5/600 |
| 6,155,260 A | 12/2000 | Lavin et al. | |
| 6,225,631 B1 | 5/2001 | Mastrippolito et al. | |
| 6,258,103 B1 | 7/2001 | Saracione | |
| 6,264,364 B1 * | 7/2001 | Pflaum | A61B 6/4441 378/196 |
| 6,275,723 B1 | 8/2001 | Ferris et al. | |
| 6,282,264 B1 * | 8/2001 | Smith | A61B 6/0457 378/167 |
| 6,327,982 B1 | 12/2001 | Jackson | |
| 6,349,912 B1 * | 2/2002 | Schauss | E04B 1/58 248/228.1 |
| 6,434,329 B1 * | 8/2002 | Dube | F16M 11/126 128/897 |
| 6,445,941 B1 | 9/2002 | Hampton | |
| 6,520,093 B1 | 2/2003 | Merl | |
| 6,627,446 B1 | 9/2003 | Roach et al. | |
| 6,653,607 B2 | 11/2003 | Ellis et al. | |
| 6,675,037 B1 * | 1/2004 | Tsekos | A61B 5/0555 600/417 |
| 6,685,884 B2 | 2/2004 | Stylli et al. | |
| 6,710,798 B1 * | 3/2004 | Hershel | G01R 31/2887 324/750.23 |
| 6,711,430 B1 | 3/2004 | Ferris et al. | |
| 6,764,648 B1 | 7/2004 | Roach et al. | |
| 6,789,510 B1 | 9/2004 | Lee | |
| 6,840,180 B2 | 1/2005 | Ulmer | |
| 6,851,392 B2 | 2/2005 | Zan et al. | |
| 6,869,593 B2 | 3/2005 | Frangioni | |
| 6,873,156 B2 | 3/2005 | Ferris et al. | |
| 6,890,485 B1 | 5/2005 | Stylli et al. | |
| 6,924,467 B2 | 8/2005 | Ellis et al. | |
| 6,957,794 B2 * | 10/2005 | Landreville | F16M 11/2085 248/123.2 |
| 7,096,059 B2 | 8/2006 | Geddes et al. | |

(56) References Cited

U.S. PATENT DOCUMENTS

| | | |
|---|---|---|
| 7,133,713 B2 | 11/2006 | Zan |
| 7,190,991 B2 | 3/2007 | Cable et al. |
| 7,223,018 B2 | 5/2007 | Kanehira |
| 7,337,751 B2 | 3/2008 | Lopez et al. |
| 7,352,889 B2 | 4/2008 | Ganz et al. |
| 7,380,299 B1 | 6/2008 | DeMayo |
| 7,414,403 B2 | 8/2008 | Chiodo |
| 7,426,904 B2 | 9/2008 | Zan et al. |
| 7,434,542 B2 | 10/2008 | Zan et al. |
| 7,865,226 B2 | 1/2011 | Chiodo |
| 8,078,256 B2 * | 12/2011 | Zan .................. A61B 8/0833 219/218 |
| 8,334,698 B2 | 12/2012 | Tammer et al. |
| 8,401,620 B2 | 3/2013 | Velusamy et al. |
| 8,945,014 B2 * | 2/2015 | Zan .................. A61B 8/0833 119/722 |
| 9,474,498 B2 * | 10/2016 | Zan .................. A61B 8/0833 |
| 2002/0012611 A1 | 1/2002 | Stylli et al. |
| 2002/0112672 A1 | 8/2002 | Schafhalter |
| 2003/0069471 A1 | 4/2003 | Nakanishi et al. |
| 2003/0094123 A1 | 5/2003 | Ulmer |
| 2003/0111021 A1 | 6/2003 | Lee |
| 2003/0120282 A1 * | 6/2003 | Scouten .................. A61B 90/10 606/130 |
| 2003/0166996 A1 | 9/2003 | Kim et al. |
| 2004/0028611 A1 | 2/2004 | Frangioni |
| 2004/0102705 A1 | 5/2004 | Zan et al. |
| 2004/0122324 A1 | 6/2004 | Zan |
| 2004/0131234 A1 * | 7/2004 | Long .................. A61B 5/0059 382/110 |
| 2004/0176677 A1 * | 9/2004 | Hwu .................. A61B 6/481 600/407 |
| 2004/0206419 A1 | 10/2004 | Ganz et al. |
| 2005/0010121 A1 | 1/2005 | Ross et al. |
| 2005/0039699 A1 | 2/2005 | Sato et al. |
| 2005/0197543 A1 | 9/2005 | Zan et al. |
| 2005/0215878 A1 | 9/2005 | Zan |
| 2006/0078501 A1 | 4/2006 | Goertz et al. |
| 2007/0131149 A1 | 6/2007 | Mayben |
| 2007/0185396 A1 | 8/2007 | Zan |
| 2008/0015420 A1 | 1/2008 | Zan et al. |
| 2009/0000567 A1 | 1/2009 | Hadjioannou et al. |
| 2012/0316404 A1 | 12/2012 | Zan et al. |
| 2013/0184572 A1 | 7/2013 | Velusamy et al. |

FOREIGN PATENT DOCUMENTS

| | | |
|---|---|---|
| JP | 2249536 | 10/1990 |
| JP | 3077552 | 4/1991 |
| JP | H4-40942 | 2/1992 |
| JP | 4256734 B2 | 9/1992 |
| JP | 08047501 B3 | 2/1996 |
| JP | 09187192 B7 | 7/1997 |
| JP | 11221242 B4 | 8/1999 |
| JP | 2001503627 B6 | 3/2001 |
| JP | 2002051662 B2 | 2/2002 |
| JP | 2002224051 B1 | 8/2002 |
| JP | 2002263076 B5 | 9/2002 |
| WO | 2002032306 | 4/2002 |
| WO | 2004032725 | 4/2004 |

OTHER PUBLICATIONS

International Searching Authority, International Preliminary Examination Report, PCT Application No. PCT/US 2003/032437, completed Mar. 3, 2006, 8 pages.

International Searching Authority, International Search Report, PCT Application PCT/US2003/032437, dated Sep. 10, 2004, 1 page.

International Searching Authority, Supplementary European Search Report, European Patent Application 03774811.8, dated Nov. 27, 2008, 5 pages.

Japan Patent Office, Notice of Reasons for Rejection, JP Patent Application 2009-098634, dated Jan. 10, 2012, 7 pages.

Turnbull, D.H. et al. "In vivo ultrasound biomicroscopy in developmental biology," *Trends in Biotechnology*, vol. 20, No. 8 (suppl.), 2002, pp. S29-S33.

VisualSonics: "Products—Vevo Integrated Rail System." <http://www.visualsonics.com/productrs/products_rail.htm>, accessed on Apr. 22, 2008; images published on Jan. 17, 2005, 4 pages.

* cited by examiner

INTEGRATED MULTI-RAIL IMAGING SYSTEM

CROSS-REFERENCE TO RELATED APPLICATIONS

This application is a continuation of U.S. patent application Ser. No. 14/576,113 filed Dec. 18, 2014, now U.S. Pat. No. 9,474,498, which is a continuation of U.S. patent application Ser. No. 13/324,996 filed Dec. 13, 2011, now U.S. Pat. No. 8,945,014, which is a continuation of U.S. patent application Ser. No. 11/053,748, filed Feb. 7, 2005, now U.S. Pat. No. 8,078,256, which is a continuation-in-part of U.S. patent application Ser. No. 10/683,168 filed on Oct. 10, 2003, now U.S. Pat. No. 7,133,713, which claims priority to and the benefit of U.S. Provisional Application No. 60/417,167 filed on Oct. 10, 2002; U.S. Provisional Application No. 60/468,959 filed on May. 9, 2003; U.S. Provisional Application No. 60/417,185, filed on Oct. 10, 2002; and U.S. Provisional Application No. 60/468,960, filed on May. 9, 2003, all of which are incorporated in their entireties in this document by reference.

BACKGROUND OF THE INVENTION

Field of the Invention

The present invention relates to a small-animal imaging system, and more particularly to a multi-rail imaging system for maintaining a desired image plane during an imaging session.

Description of the Prior Art

Over the past few years researchers in disciplines as diverse as neuroscience, developmental biology, genetics, and oncology have struggled with the challenge of injecting microliter and nanoliter quantities of fluid into discrete regions of organ systems. With the development and launch of ultrasound biomicroscopy (UBM) technology in the small animal imaging marketplace, the capacity to non-invasively observe, in real-time, the position of a needle or probe relative to an organ became a reality. One disadvantage with present positioning systems for animals is that straightforward repeatability of position with different animals is not possible.

For example, during injections procedures, a common problem has been the challenge of aligning a needle guidance device, which injects very small quantities of fluid, with a UBM scanhead device. Micromanipulation of both devices is necessary to help ensure that the injector needle of the needle guidance device lies within the same plane as the ultrasound scanhead so that the operator can guide the needle to the organ of interest. Consequently, this is a laborious and time-consuming process, which is aggravated by the need to move both devices away from an animal handling device, upon which a small animal is mounted, when a different animal is to be scanned. Current systems use independent, non-integrated, positioning methods for the various devices used in the imaging session.

Much information and expertise is available on the sequence and the manipulation of the mouse genome. Because of the similarity between the mouse and human genomes, the mouse is used as a model for understanding human gene function, and a model for many human disease processes. Manipulations permitted by guided injection technique facilitate experiments to further the understanding of genome function, the functional stages of organ development, the differentiation of stem cells, and facilitate testing of new interventions for models of human disease.

Ultrasound imaging can be used to generate a high resolution, cross sectional image in real-time so the imaging system can be operated while a needle is introduced into the small animal that gives the operator immediate accurate feedback for positioning of the needle tip in the target space. However, there is a need for providing a system to provide for quick manipulation of imaging apparatus and, if used, injection apparatus, around a sequence of different animals in a time efficient manner.

There is a further need for a mounting table for handling of small animals, such as mice, rats, rabbits, and the like, in both a minimally stressful and time efficient manner during the course of an imaging session. Control of the animal's physiological condition is of paramount concern, but doing so in an environment that permits the movement of the immobilized subject in a variety of positions to maximize the success of placing the animal within the imaging plane of the imaging apparatus. Further complicating these procedures is the fact that some protocols necessitate that the embryos of pregnant animals be externalized from the abdomen to provide for improved imaging resolution.

To date, no device serves each of the needs outlined to enable the safe and effective delivery of anaesthesia to small animals, the physiological monitoring of the immobilized subject, the capacity for a range of motion, and the ability to successfully externalize embryos on a specialized table.

SUMMARY

The imaging system of the present invention allows for productive imaging of small-animals. In one example, the imaging system can include a plurality of elongated rails, a scanhead assembly, and a small animal mount assembly. In another example, a needle injection assembly is also included in the imaging system.

The plurality of elongated rails can include a first rail, a second rail, and, if used, a third rail. Each rail has a proximal end, a spaced distal end, and a longitudinal axis. In one exemplary configuration, the proximal end of the first rail is positioned proximate a first edge of the second rail intermediate the proximal end and distal end of the second rail such that the longitudinal axis of the first rail is at an angle to the longitudinal axis of the second rail. In another exemplary example, the proximal end of the third rail is positioned proximate a second edge of the second rail intermediate the proximal end and distal end of the second rail such that the third rail and the first rails are on opposite sides of the second rail. In this example, the longitudinal axis of the third rail is substantially coaxial to the longitudinal axis of the first rail.

The scanhead assembly is selectively mounted onto the first rail and is constructed and arranged for movement in a linear bi-directional manner along the longitudinal axis of the first rail. The small-animal mount assembly is selectively mounted onto the second rail and is constructed and arranged for movement in a linear bi-directional manner along the longitudinal axis of the second rail. In one aspect, the needle injection assembly is selectively mounted onto the third rail and is constructed and arranged for movement in a linear bi-directional manner along the longitudinal axis of the third rail. Alternatively, the needle injection assembly is mounted onto the first rail, such that the second rail is positioned therebetween the needle injection assembly and the scanhead assembly.

BRIEF DESCRIPTION OF THE DRAWINGS

These and other features of the preferred embodiments of the invention will become more apparent in the following detailed description in which reference is made to the appended drawings Wherein.

DETAILED DESCRIPTION OF THE INVENTION

The present invention is more particularly described in the following examples that are intended as illustrative only since numerous modifications and variations therein will be apparent to those skilled in the art. Thus the embodiments of this invention described and illustrated herein are not intended to be exhaustive or to limit the invention to the precise form disclosed. They are chosen to describe or to best explain the principles of the invention and its application and practical use to thereby enable others skilled in the art to best utilize the invention. As used in the specification and in the claims, "a," "an," and "the" can mean one or more, depending upon the context in which it is used. The preferred embodiment is now described with reference to the figures, in which like numbers indicate like parts throughout the figures.

Figure 1:
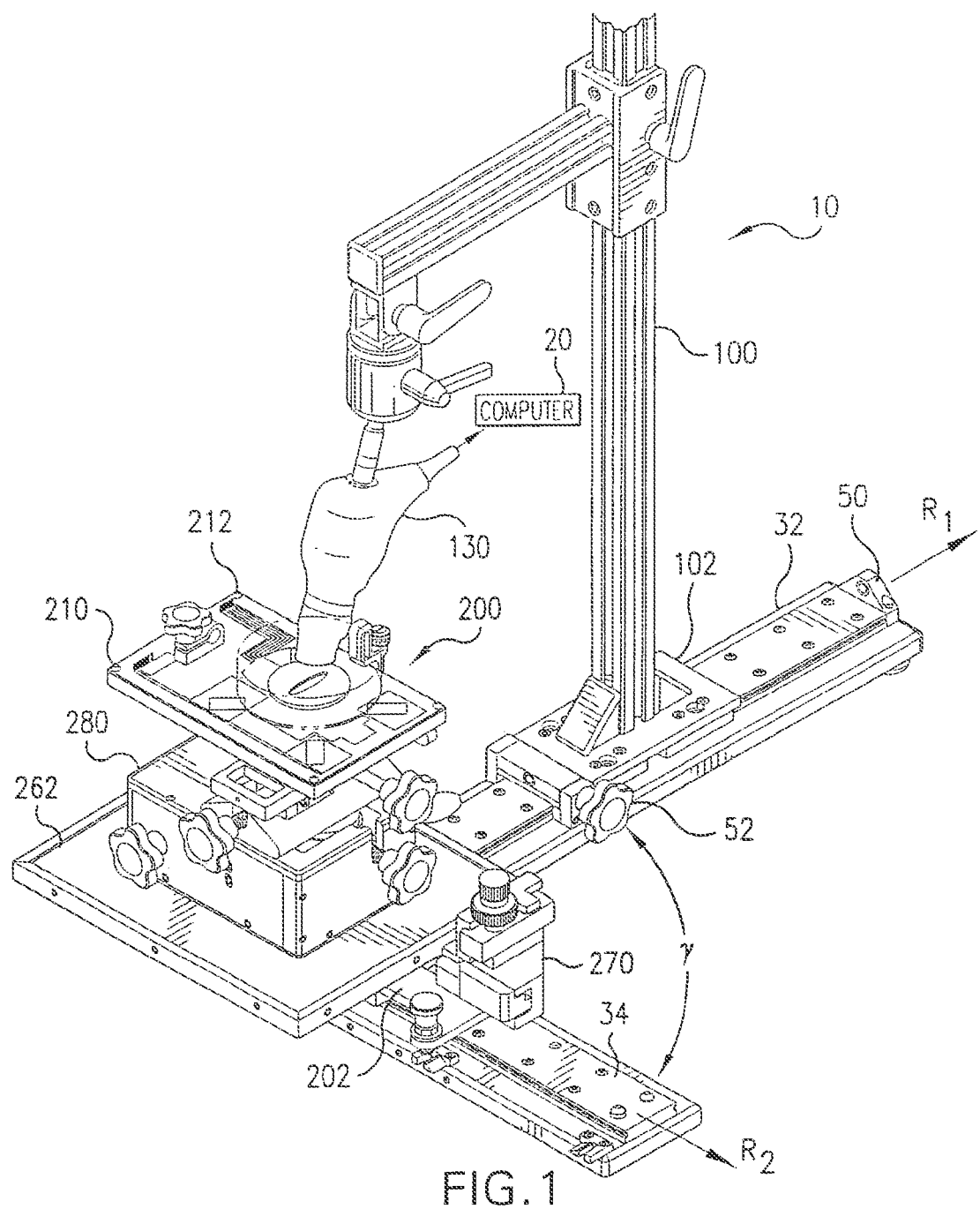
FIG. 1 is a perspective view of one embodiment of a small-animal imaging system of the present invention, showing a scanhead assembly mounted onto a first rail and a small-animal mount assembly mounted onto a second rail.
Figure 2:
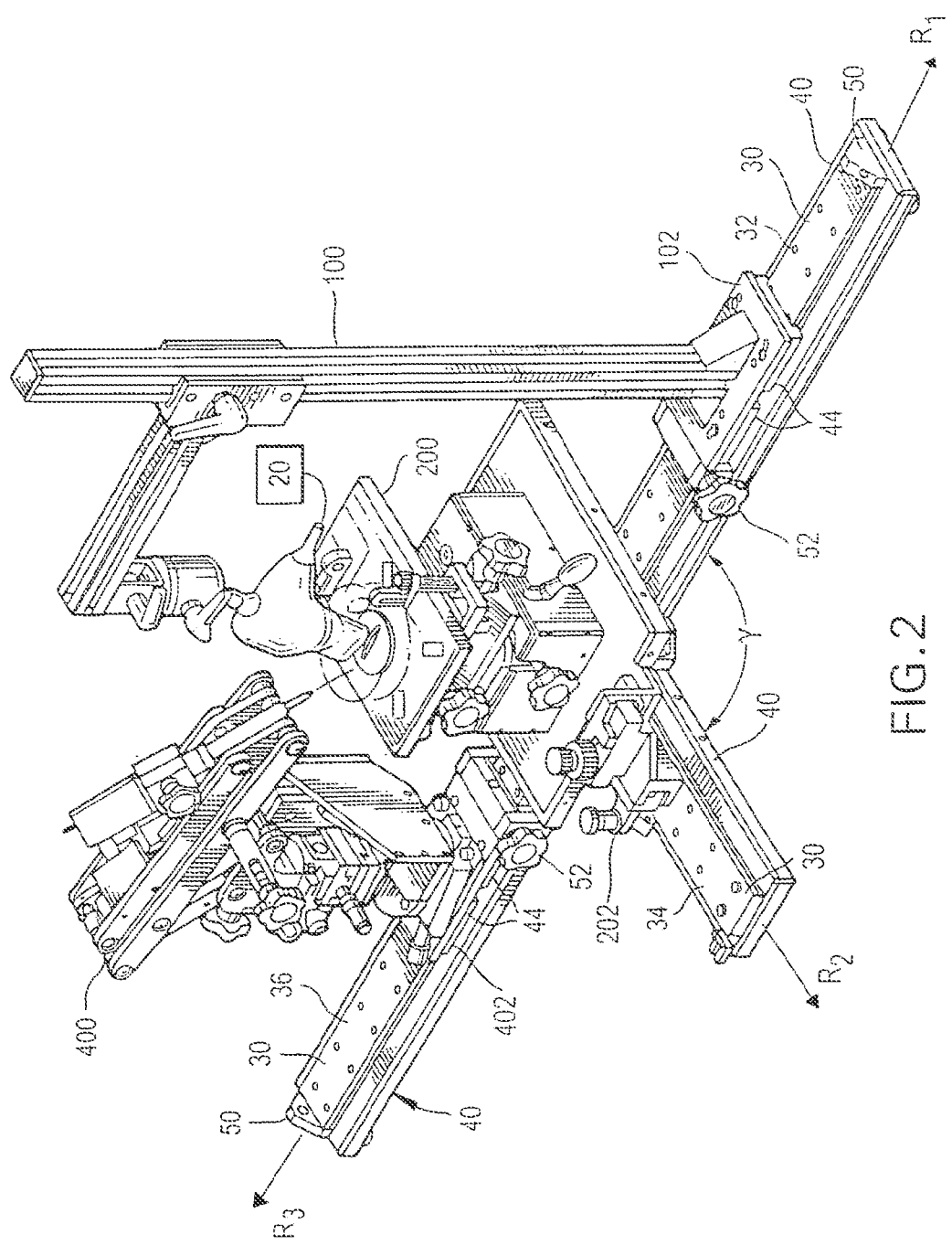
FIG. 2 is a perspective view of an alternative embodiment of a small-animal imaging system of the present invention, showing a scanhead assembly mounted onto a first rail, a small-animal mount assembly mounted onto a second rail, and a needle injection assembly mounted onto a third rail.
Figure 3:
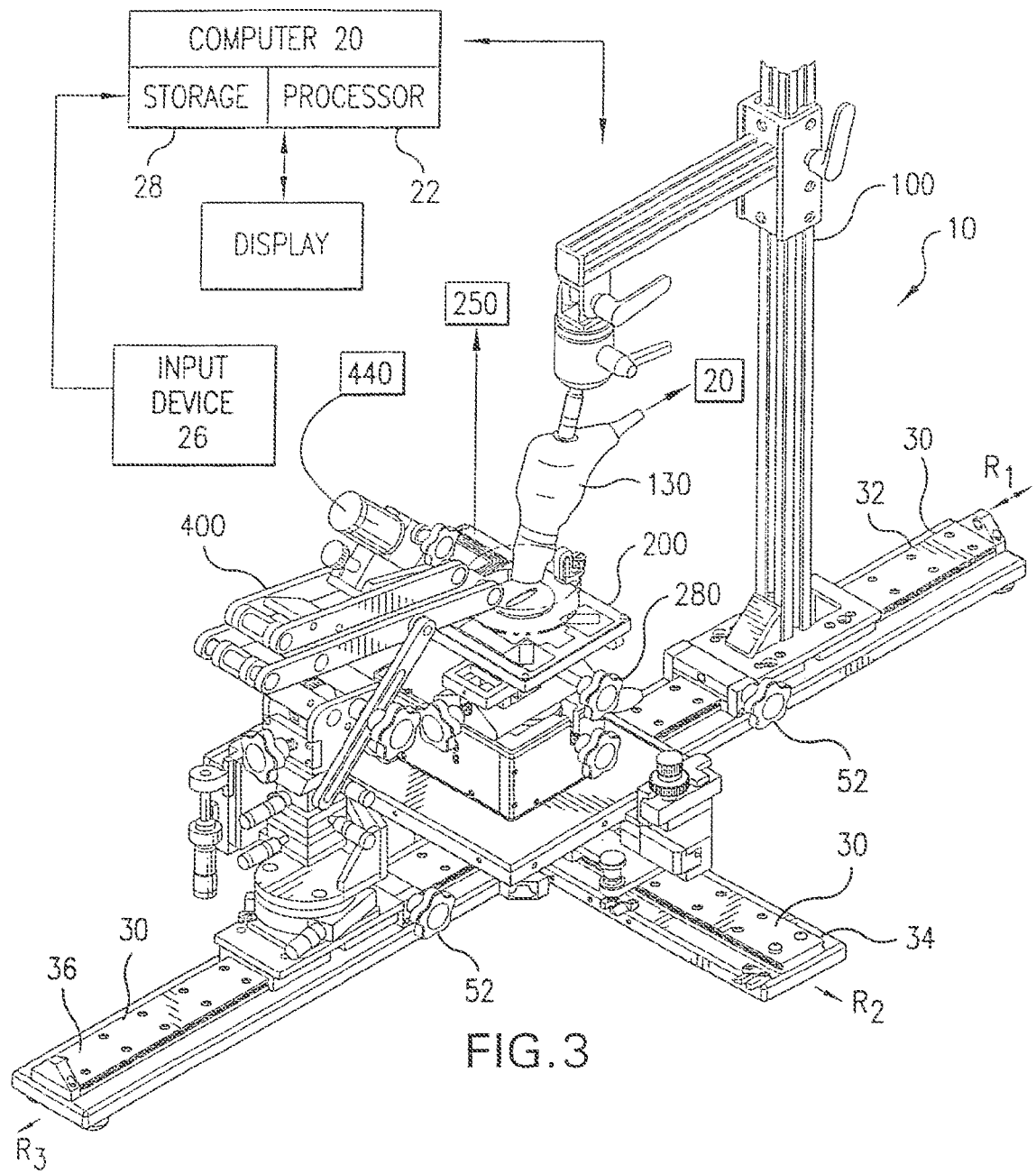
FIG. 3 is a schematic view of the small-animal imaging system of FIG. 2.
Figure 4:
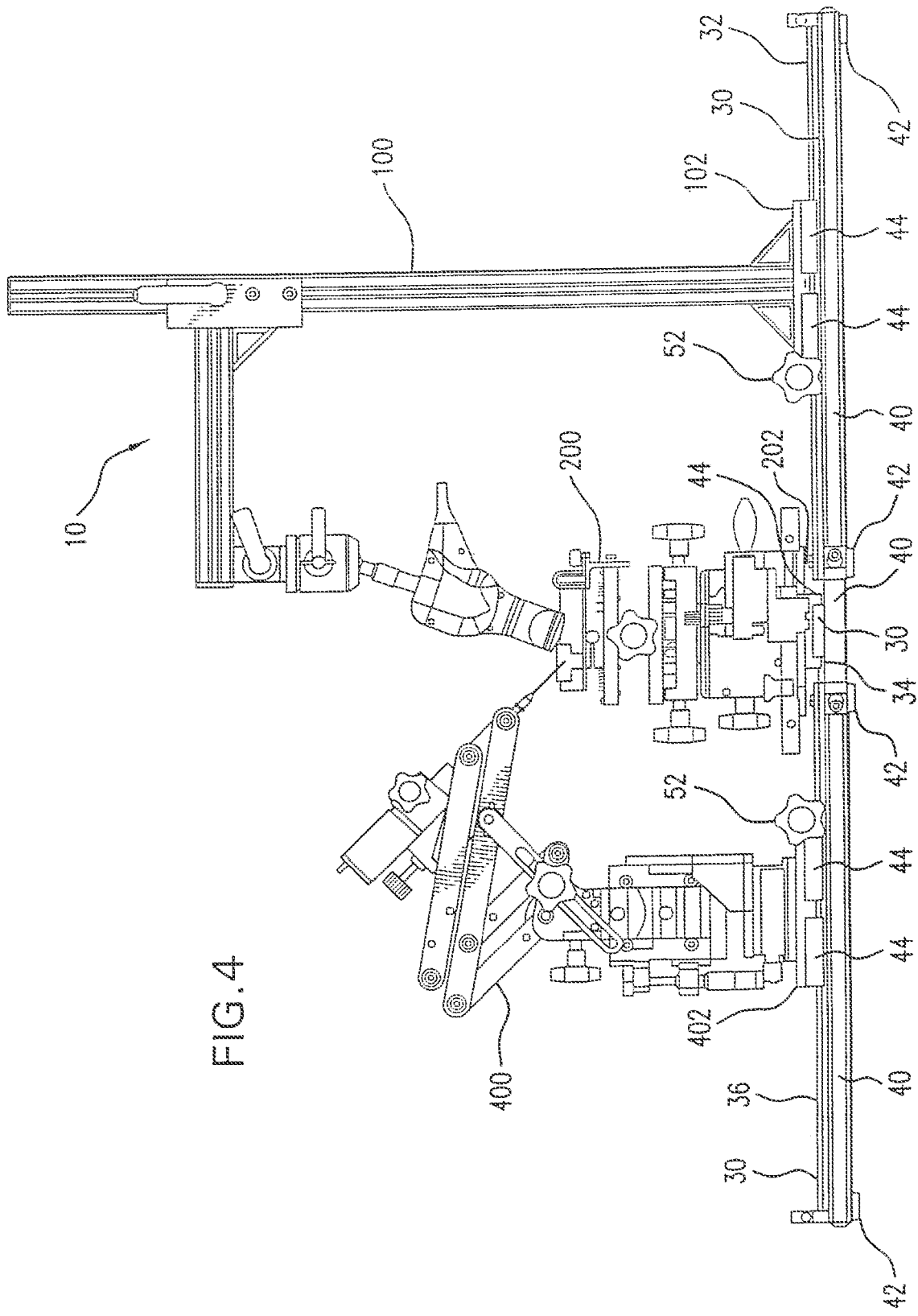
FIG. 4 is a side view of the small-animal imaging system of FIG. 2.
Figure 5:
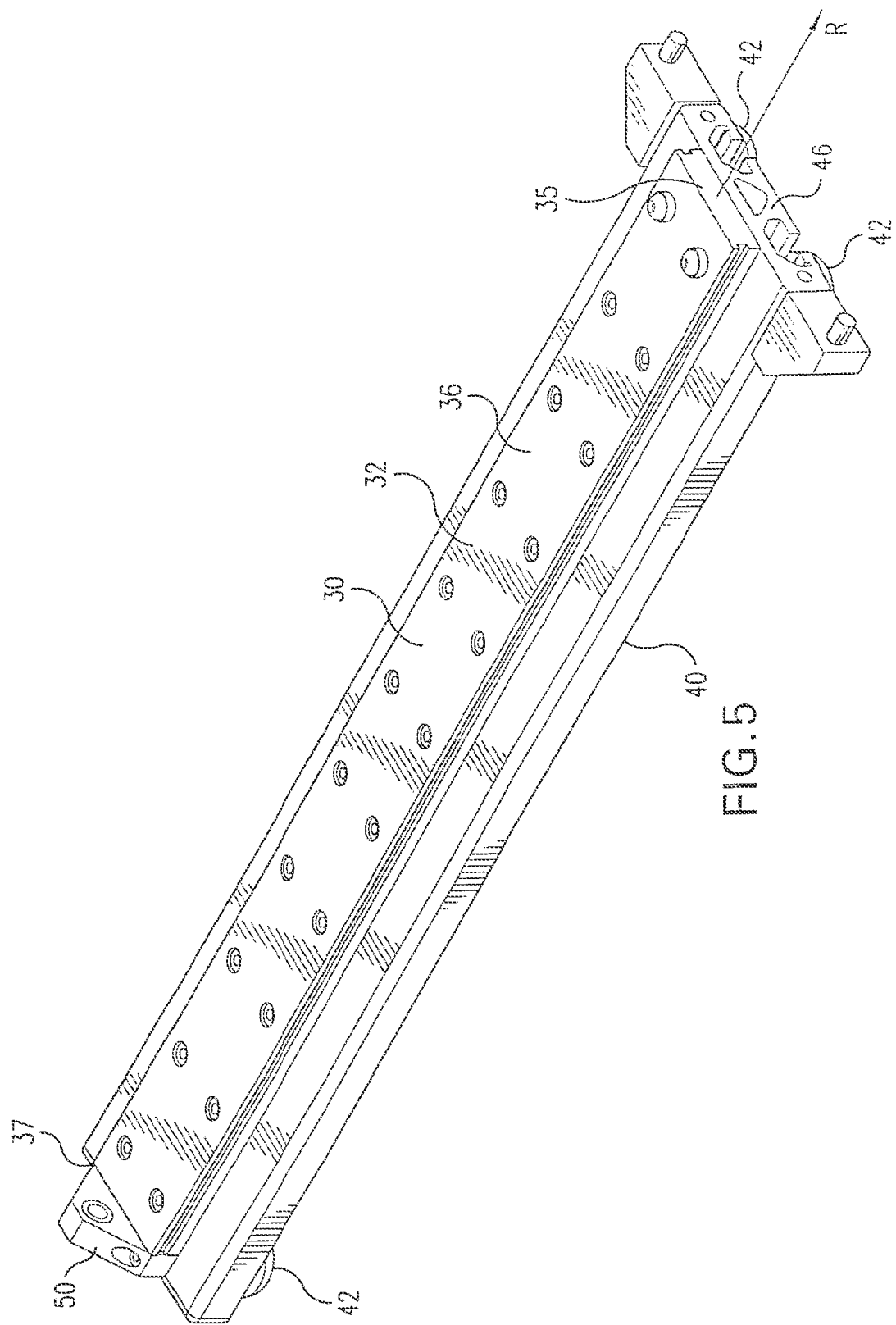
FIG. 5 is a perspective view of a first or third rail of the present invention.
Figure 6:
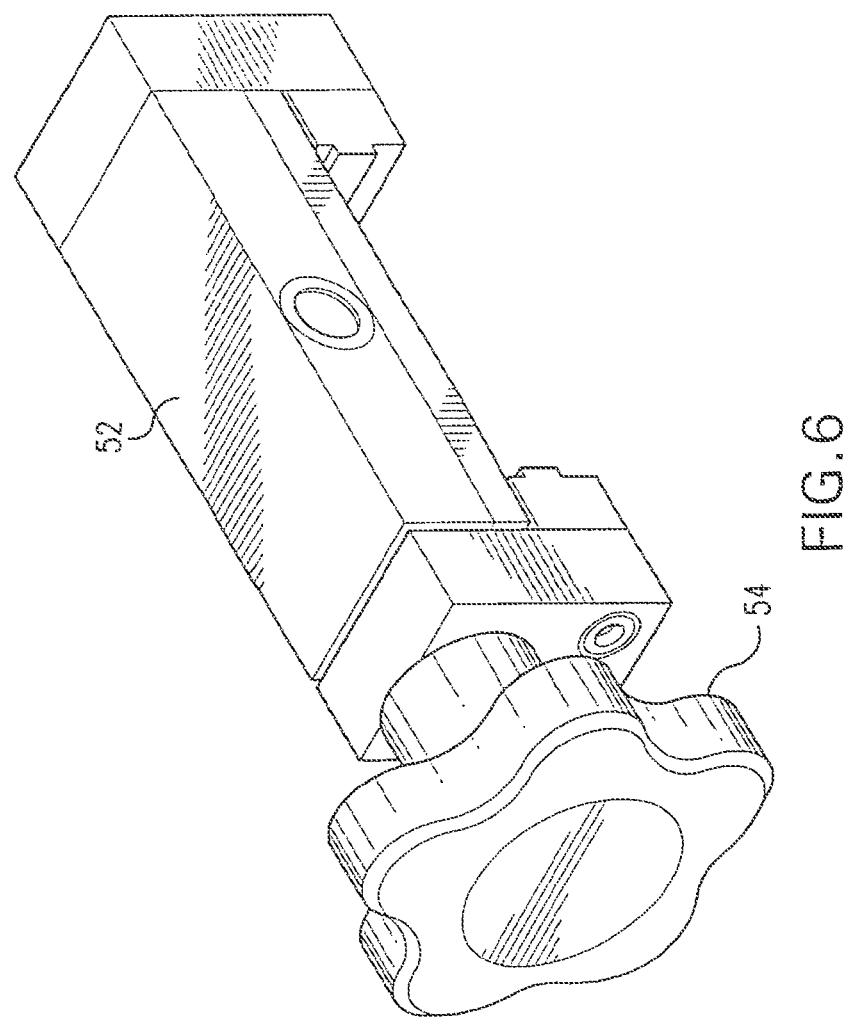
FIG. 6 is a perspective view of a movable stop.
Figure 7:
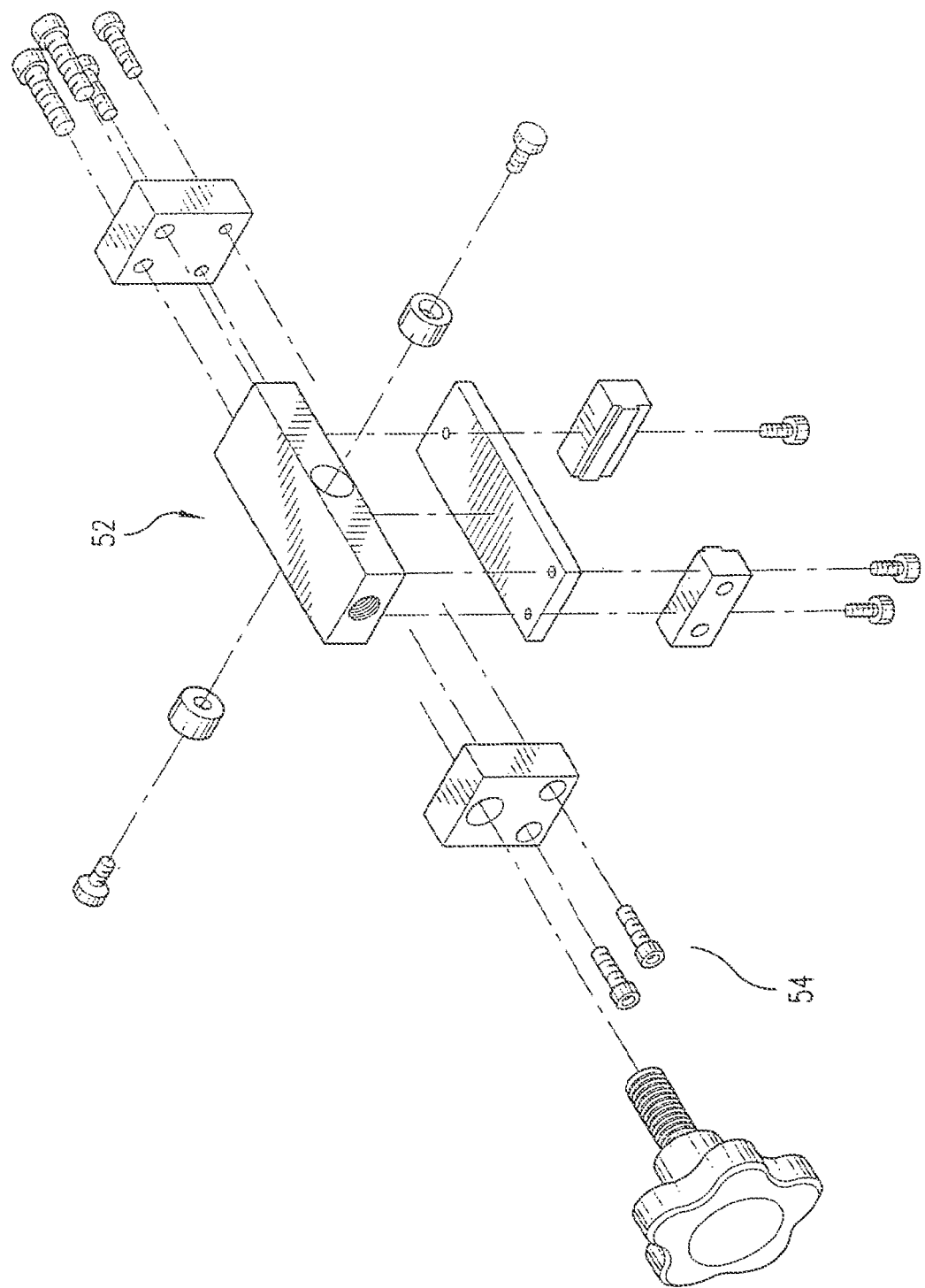
FIG. 7 is an exploded view of the movable stop of FIG. 6.
Figure 8:
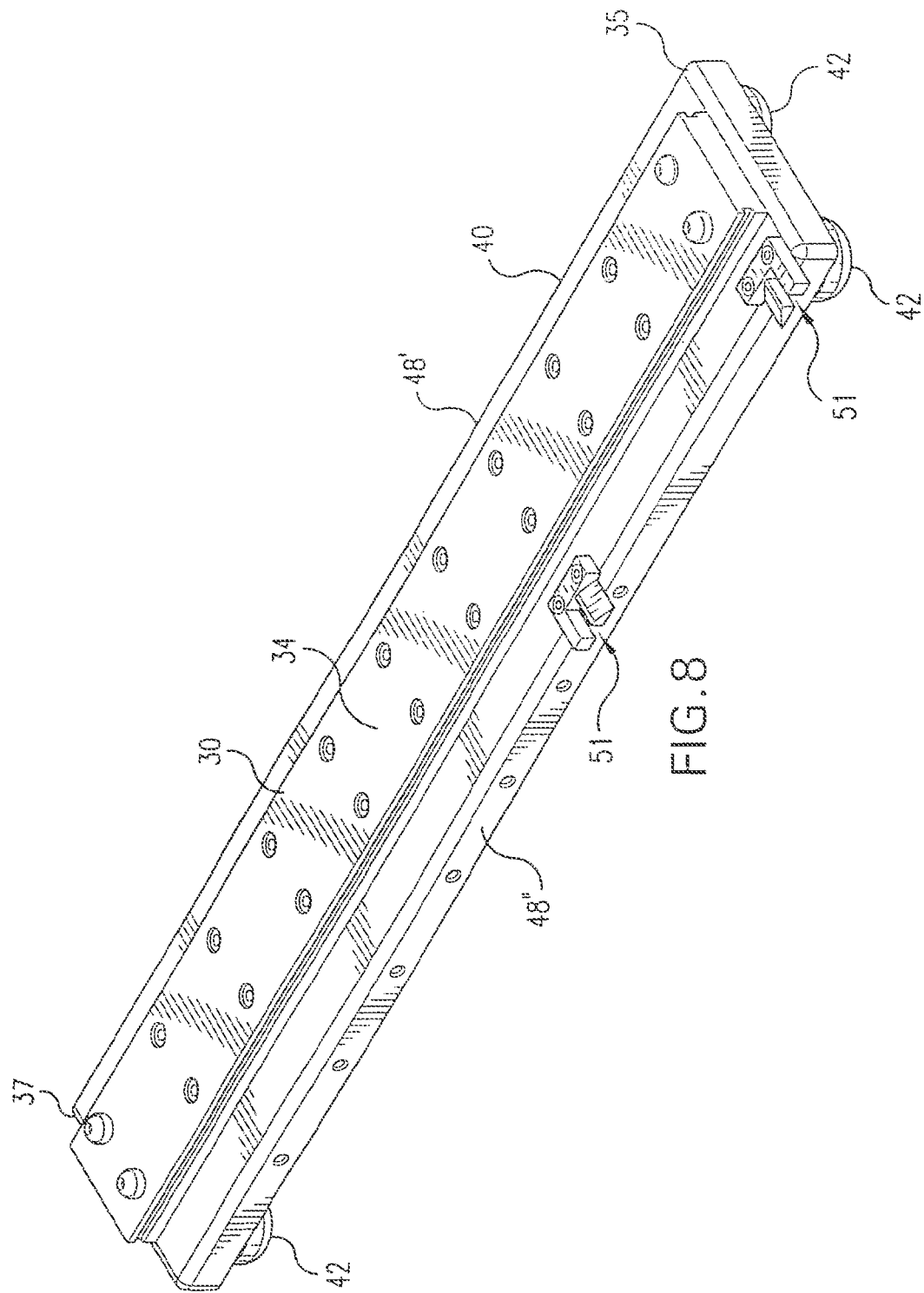
FIG. 8 is a perspective view of an embodiment of the second rail of the present invention showing two spaced fixed stops.
Figure 9:
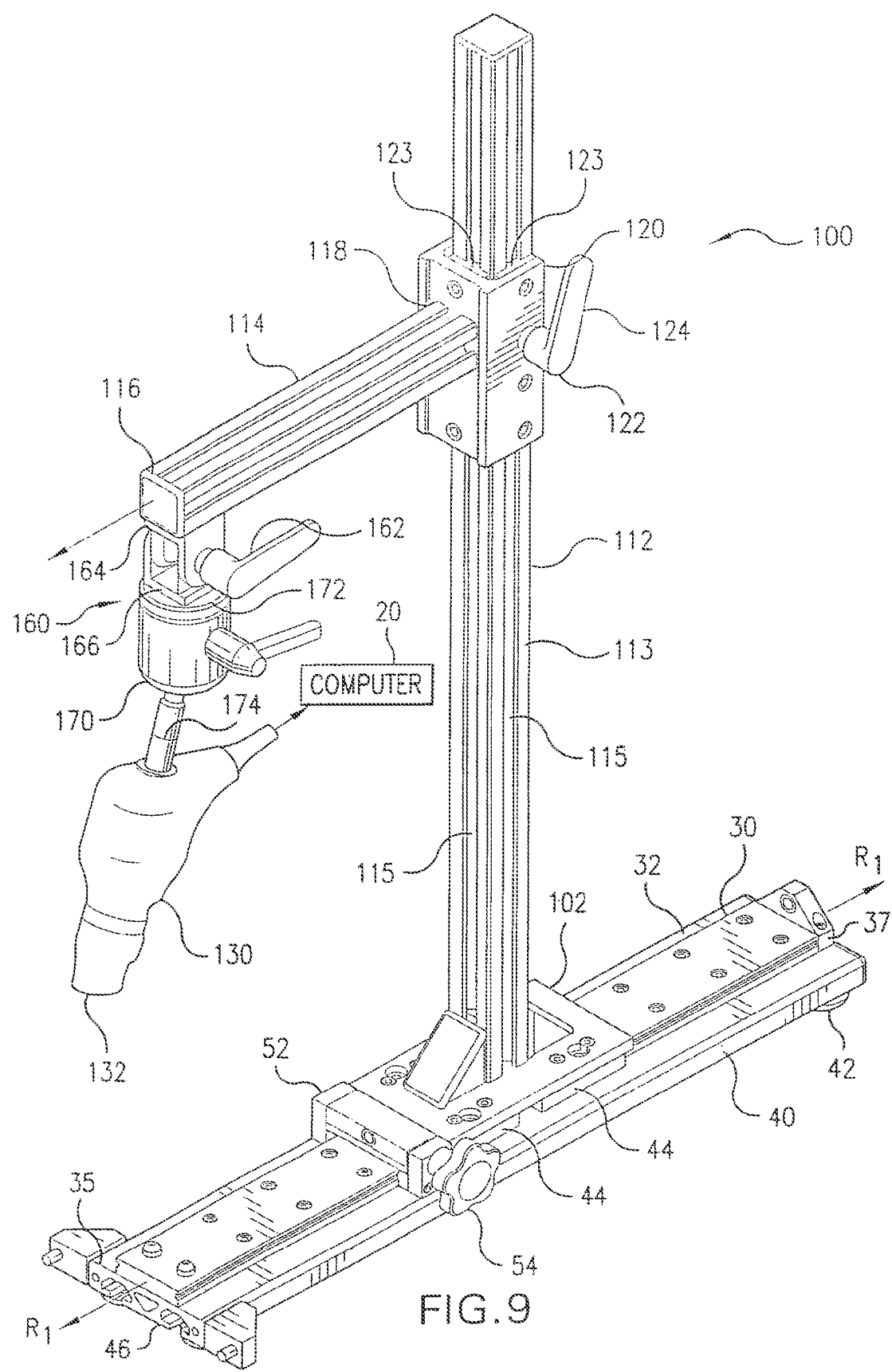
FIG. 9 is a perspective view of the scanhead assembly mounted onto the first rail, showing a mount and a scanhead unit.
Figure 10:
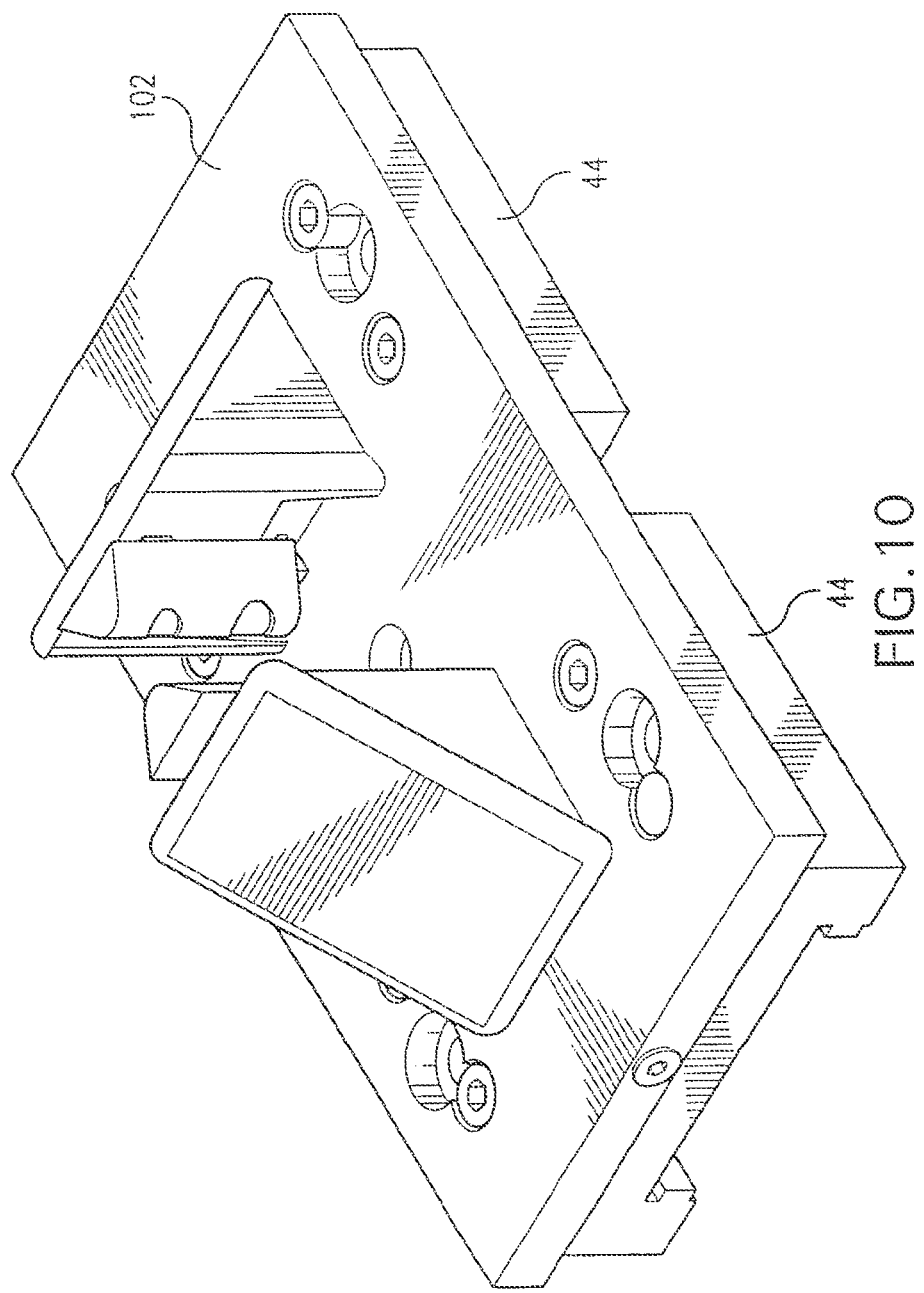
FIG. 10 is a perspective view of a base member of the scanhead assembly showing at least one carriage connected to the bottom of the base member.
Figure 11:
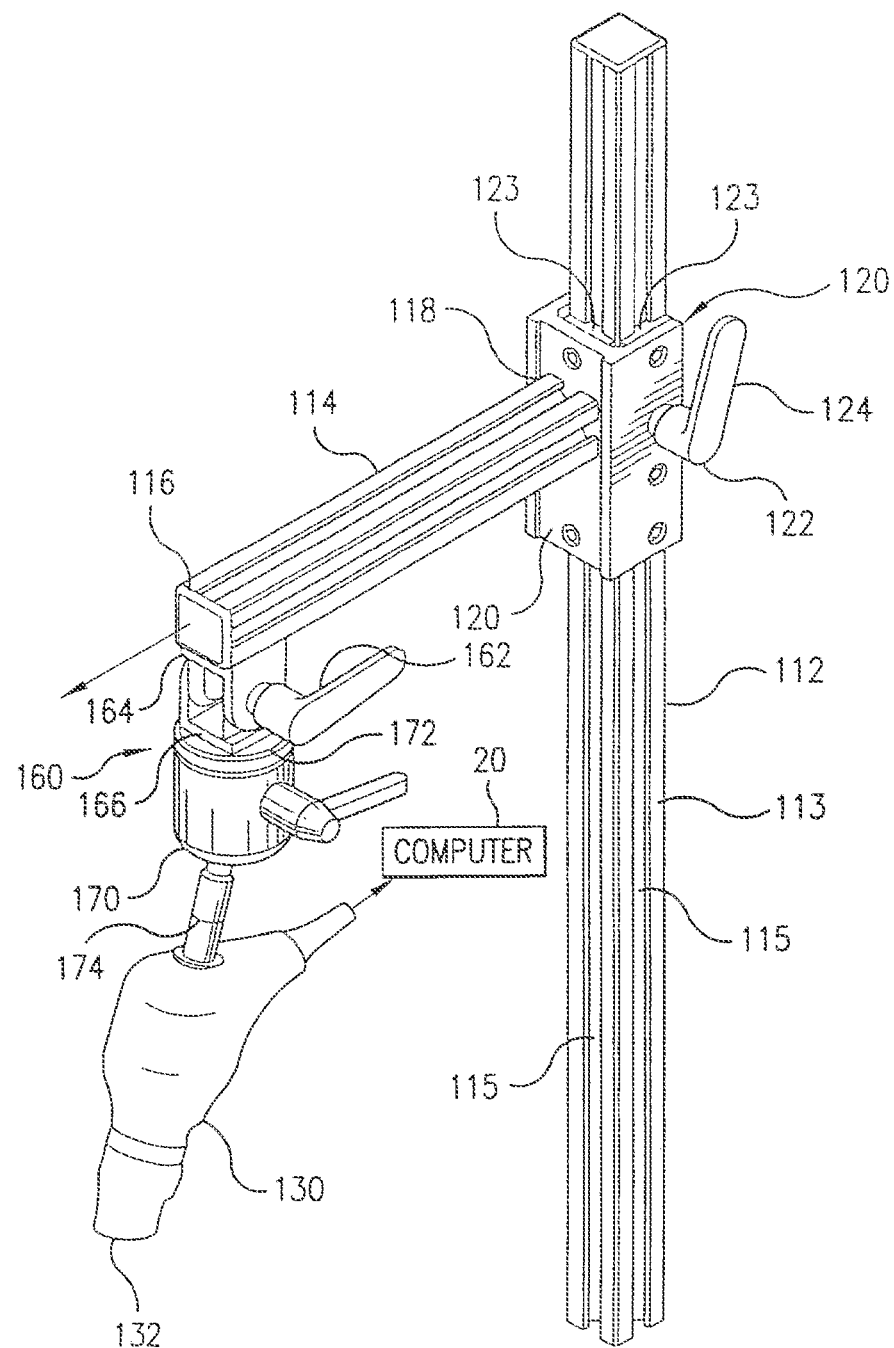
FIG. 11 is a perspective view of an elongate upright member, a cantilever beam, and a scanhead orientation control mechanism of the scanhead assembly of FIG. 9.
Figure 12:
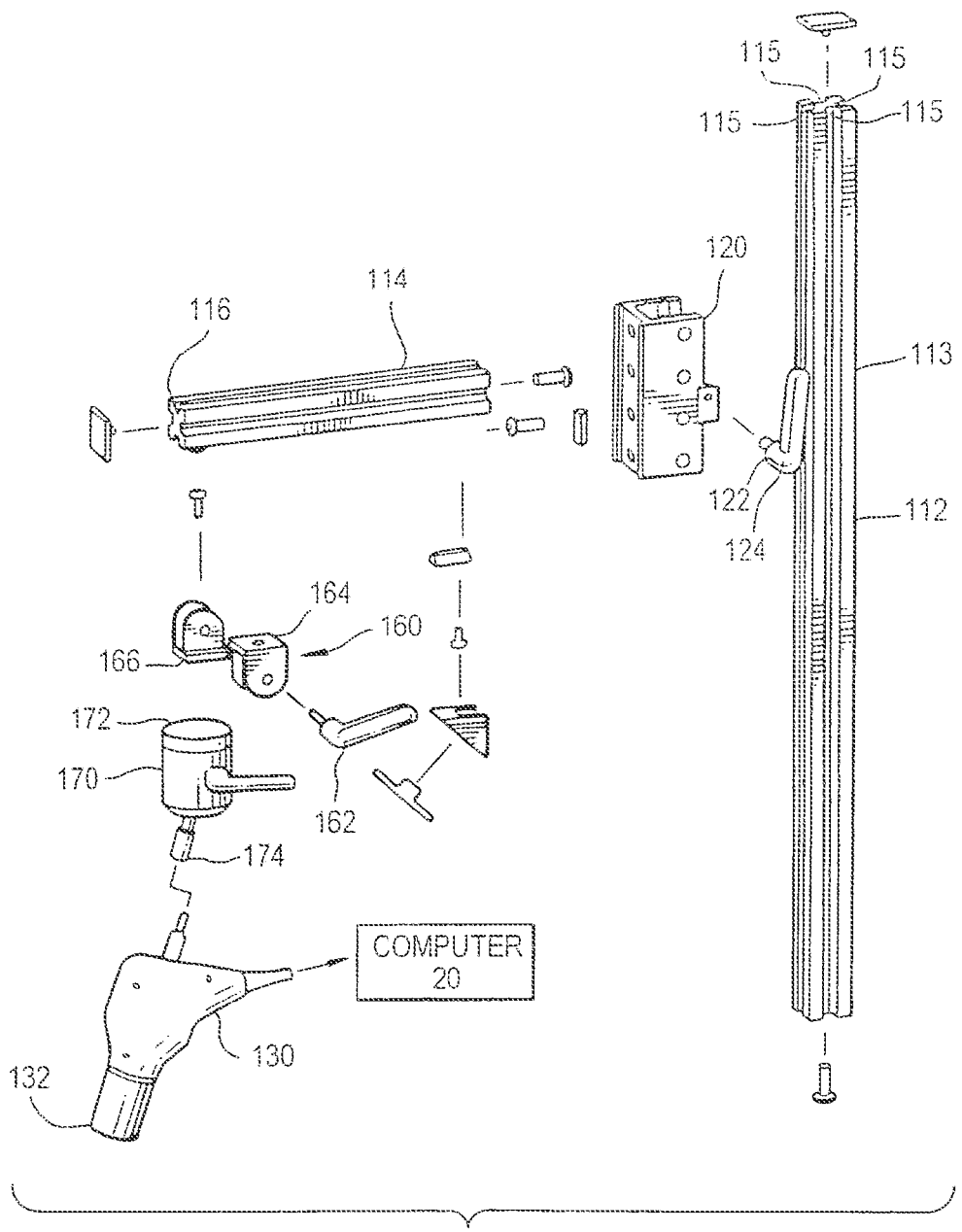
FIG. 12 is an exploded view of the elongate upright member, the cantilever beam, and the scanhead orientation control mechanism shown in FIG. 11.
Figure 13:
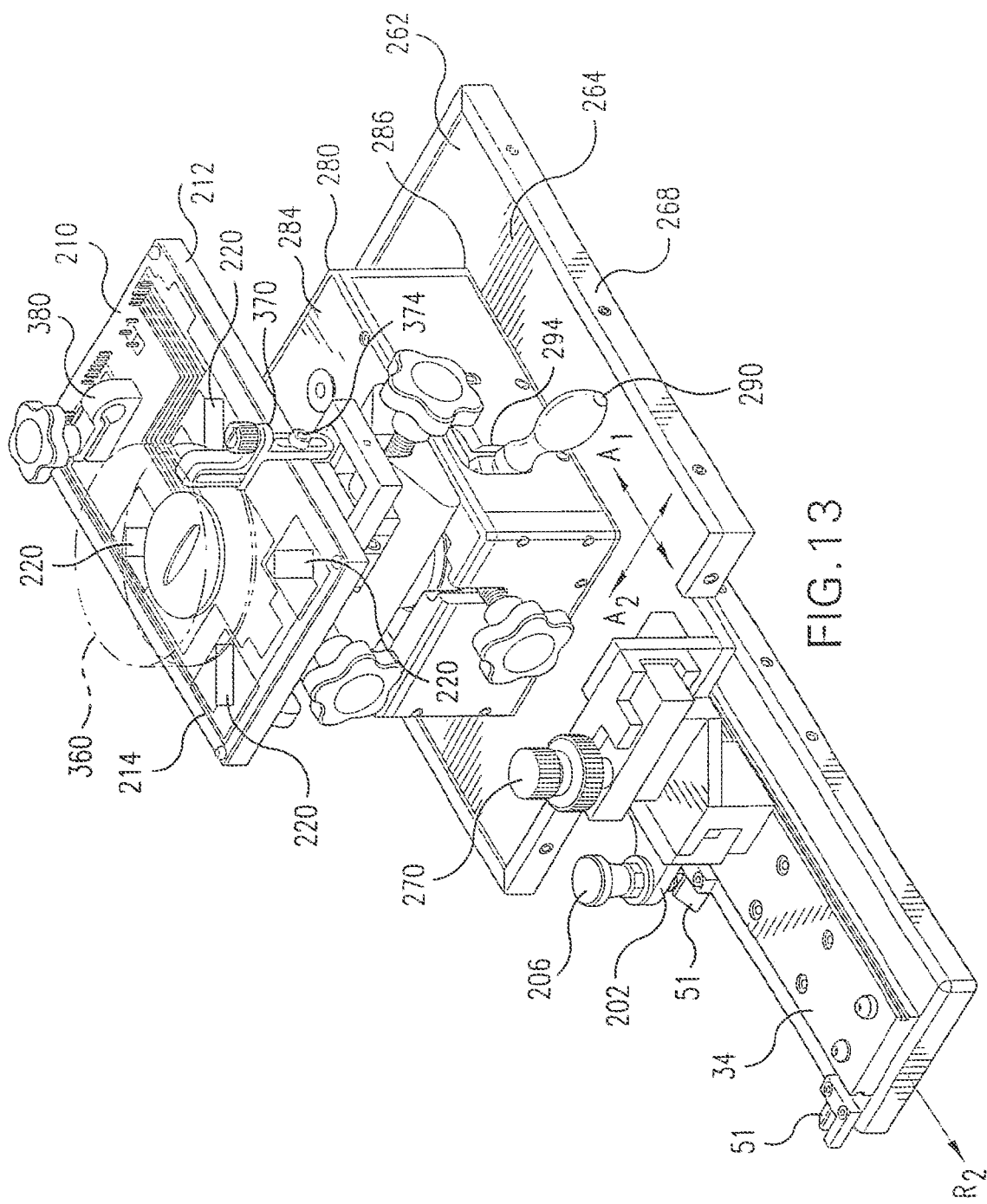
FIG. 13 is a perspective view of the small-animal mount assembly mounted onto the second rail.
Figure 14:
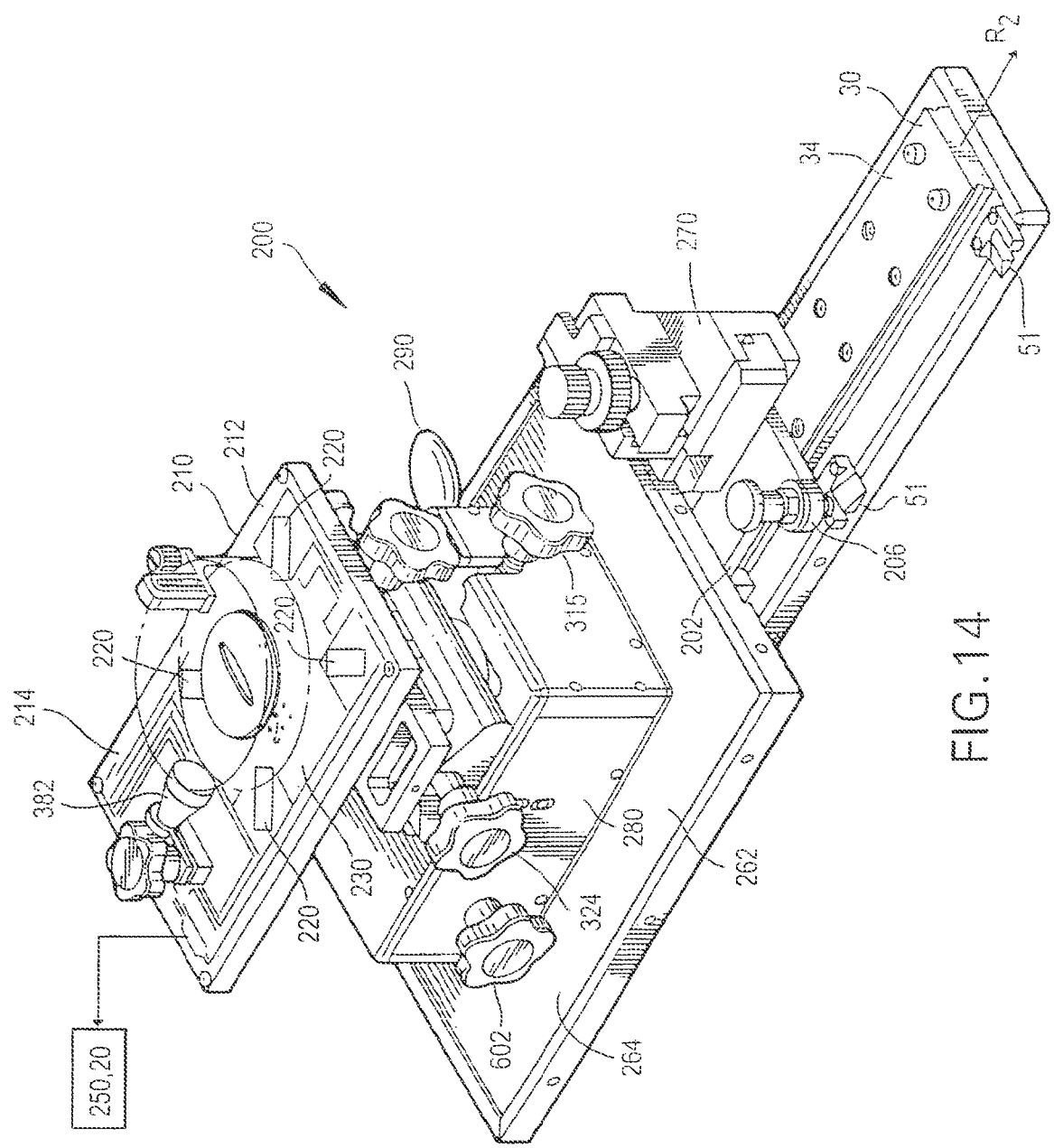
FIG. 14 is a perspective view of the small-animal mount assembly of FIG. 13.
Figure 15:
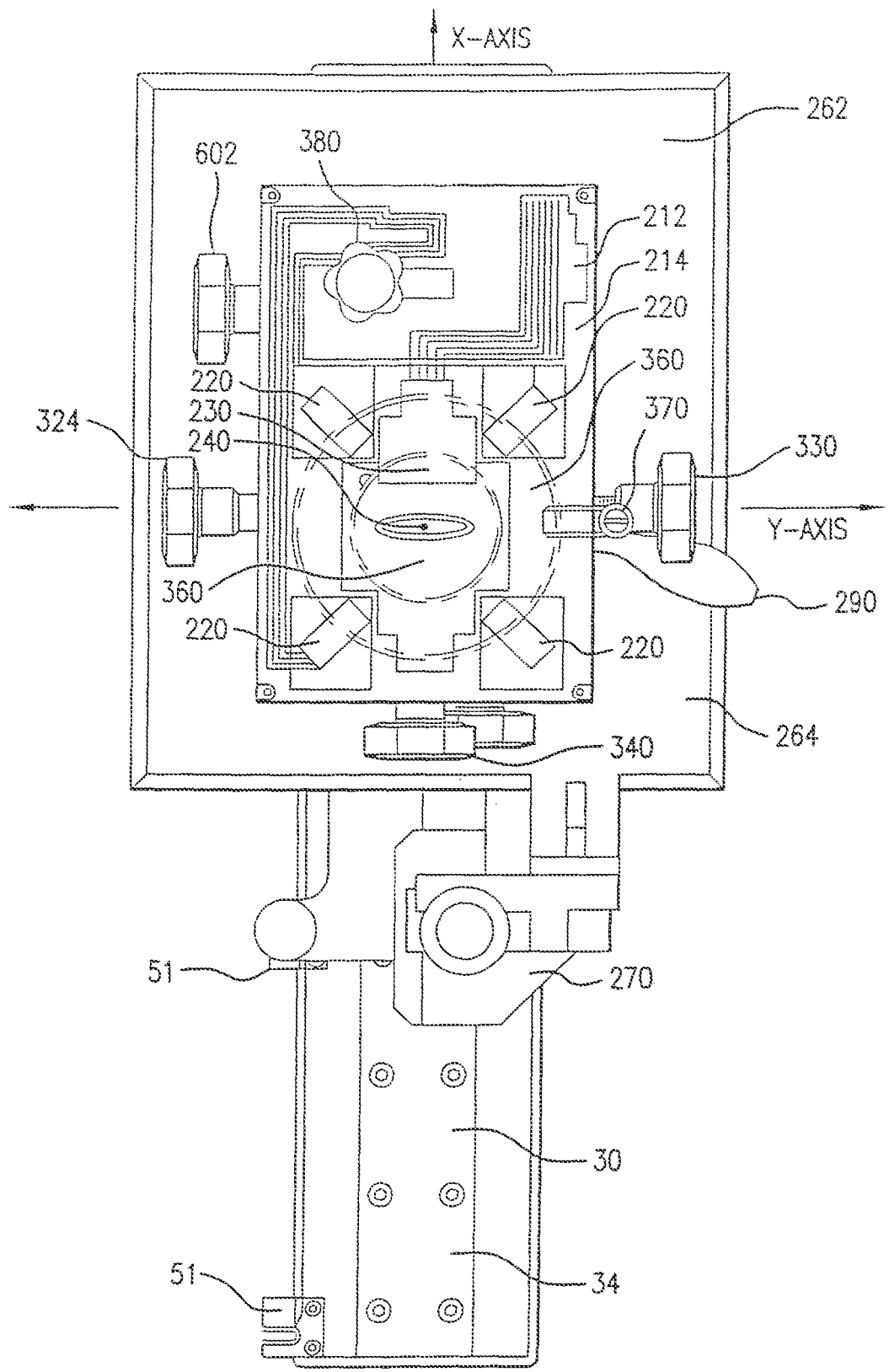
FIG. 15 is a top view of the small-animal mount assembly of FIG. 13.
Figure 16:
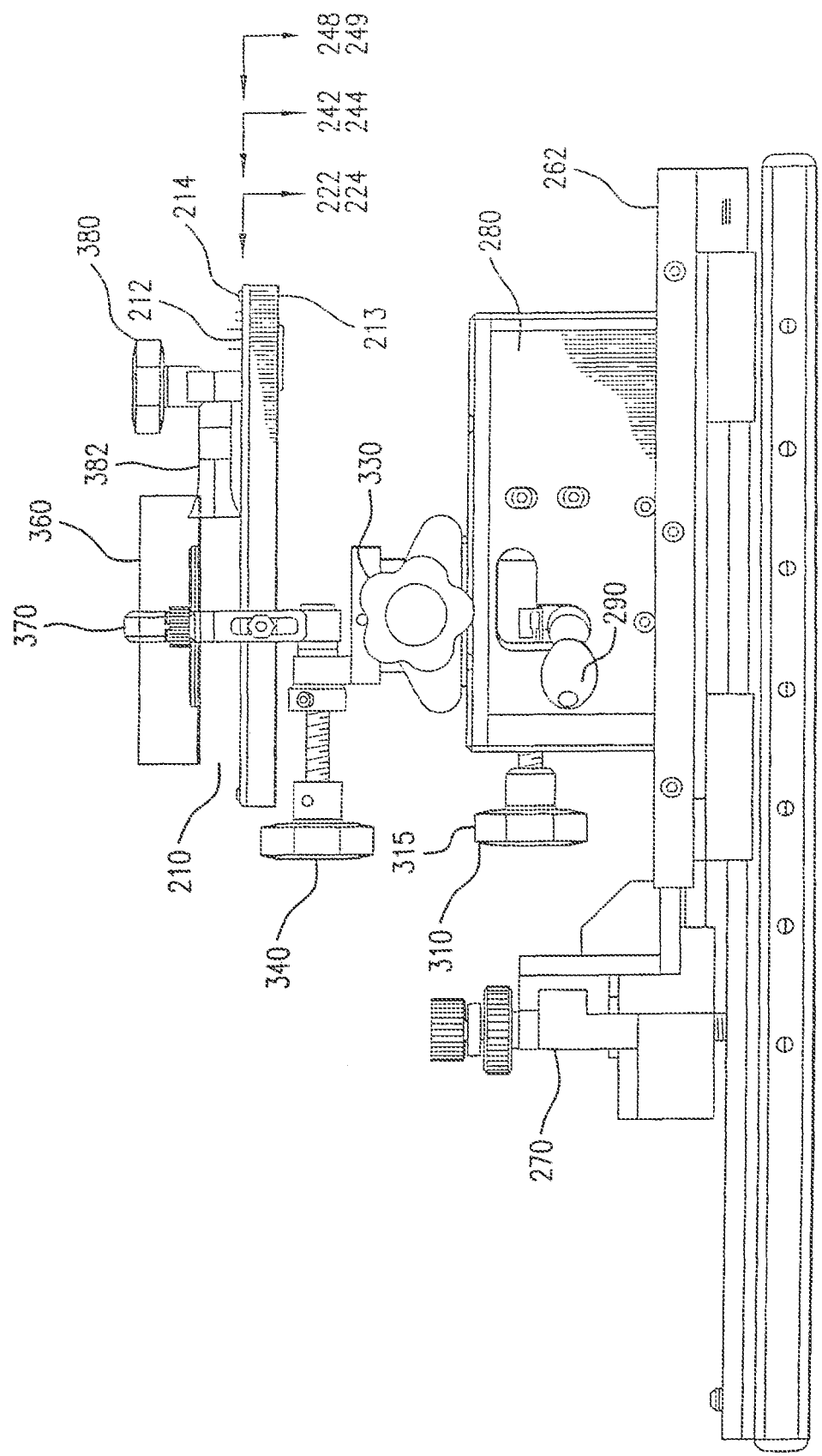
FIG. 16 is a side view of the small-animal mount assembly of FIG. 13.
Figure 17:
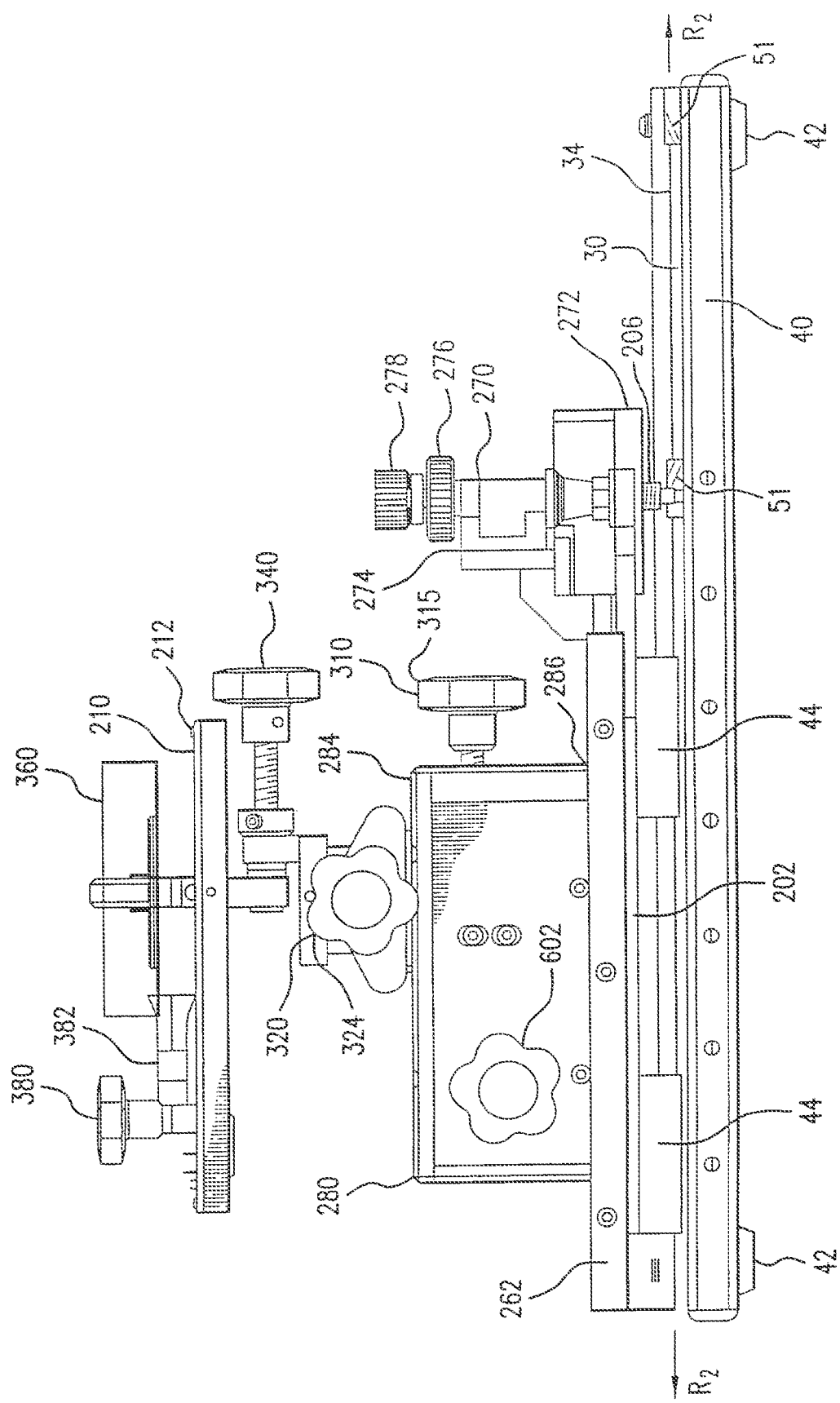
FIG. 17 is a side view of the small-animal mount assembly of FIG. 13.
Figure 18:
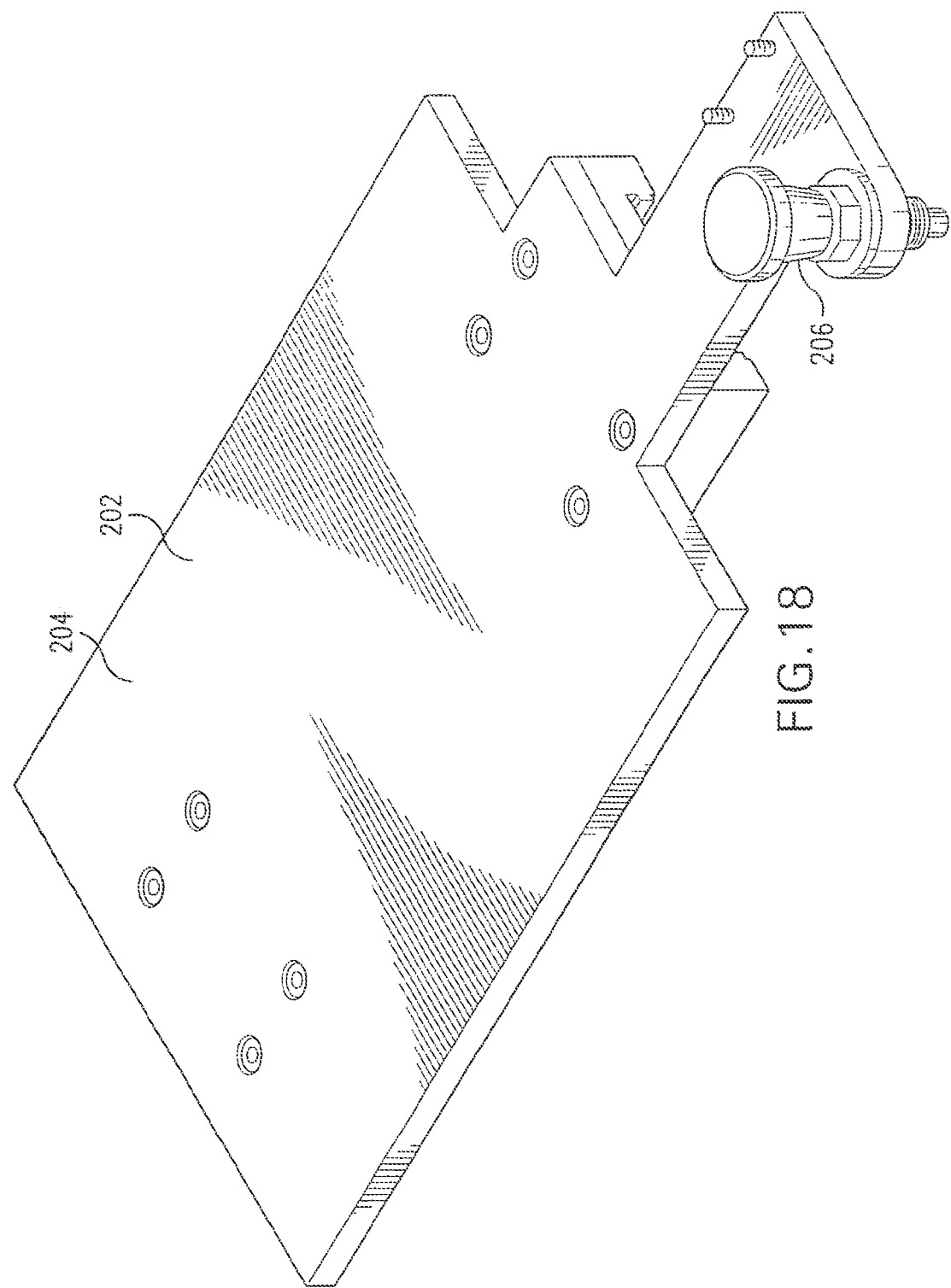
FIG. 18 is a perspective view of a base member of a mount subassembly of the small-animal mount assembly shown in FIG. 13.
Figure 19:
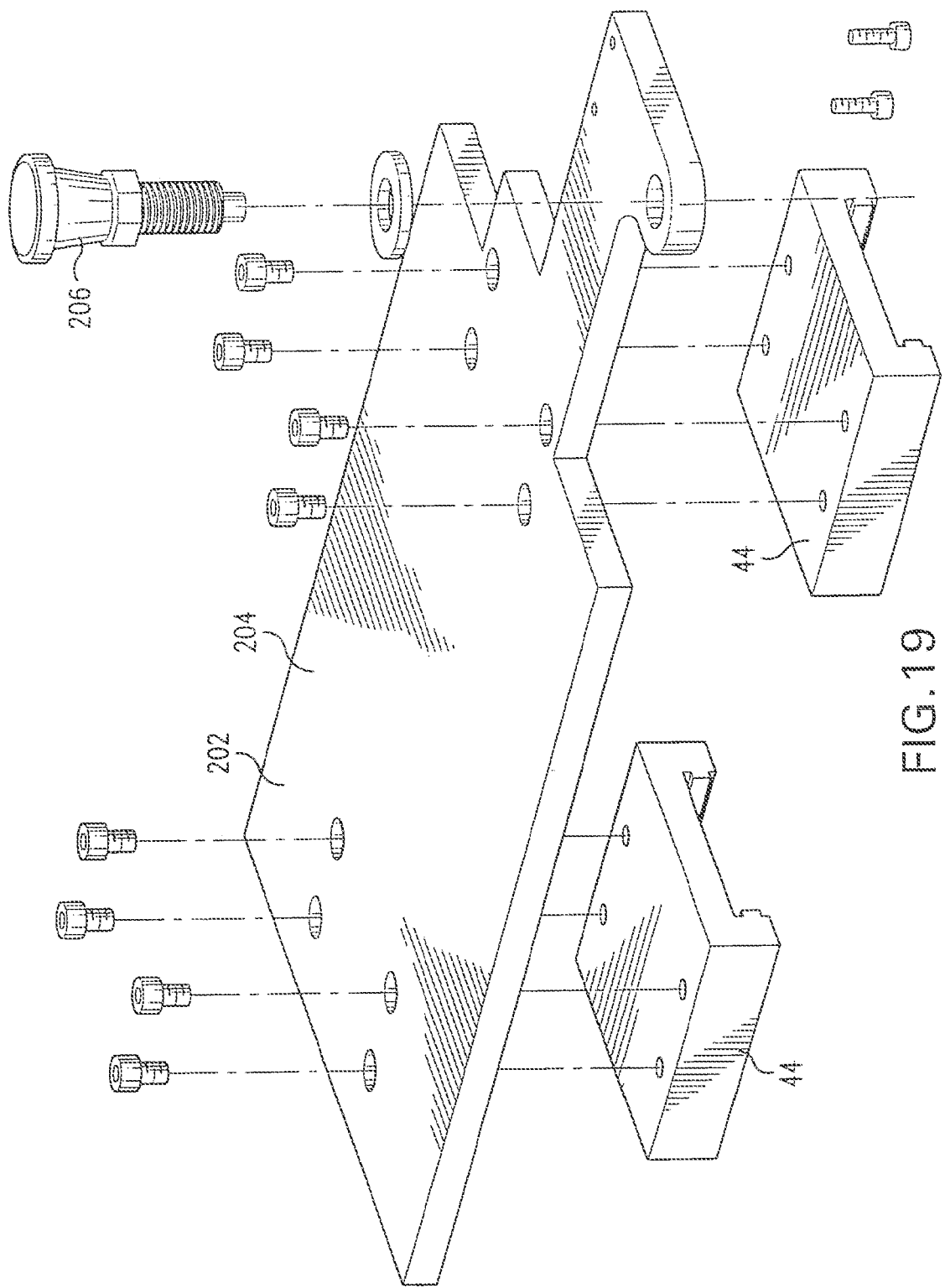
FIG. 19 is an exploded view of the base member shown in FIG. 18.
Figure 20:
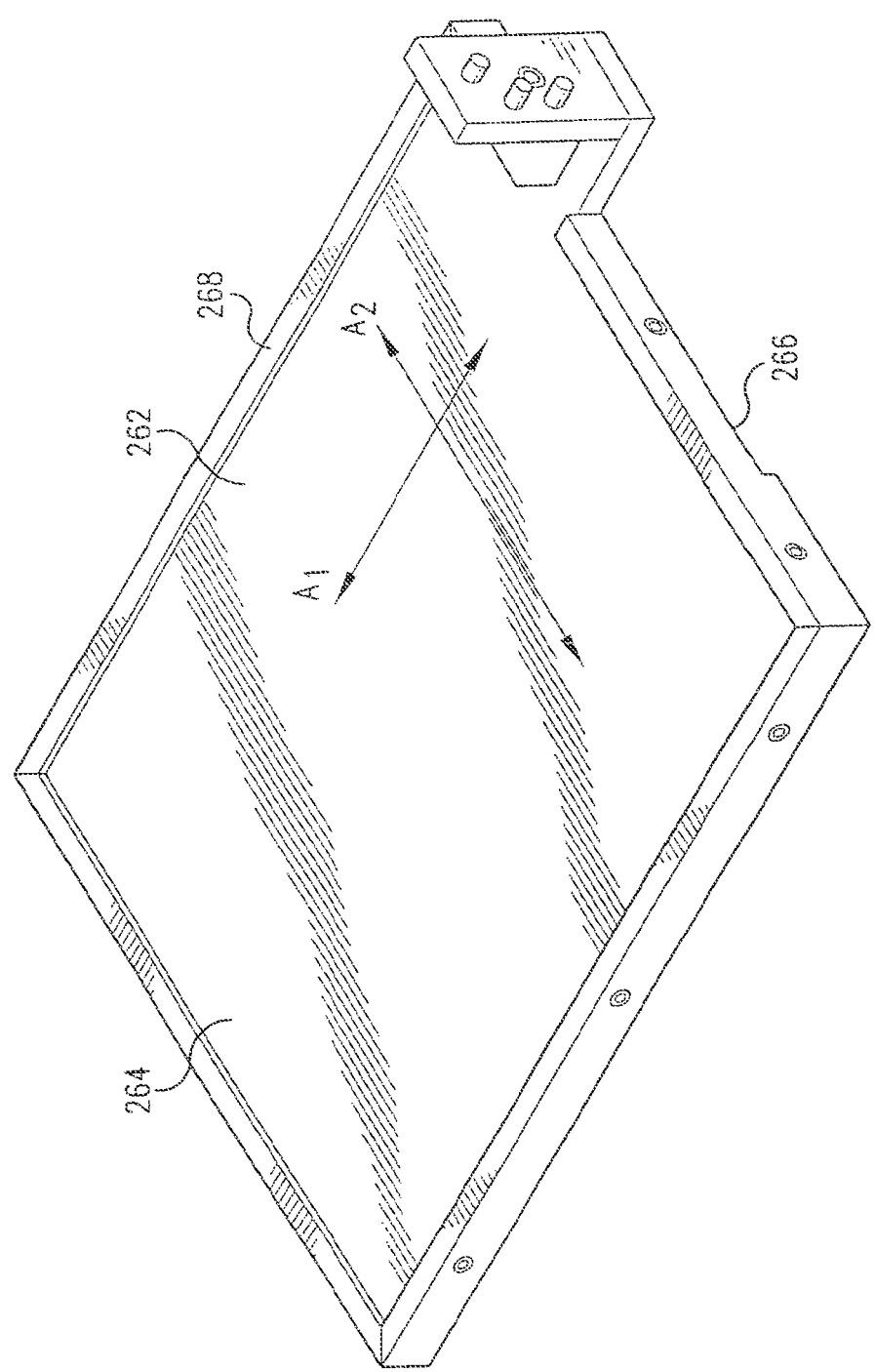
FIG. 20 is a perspective view of a planar platform of the mount subassembly.
Figure 21:
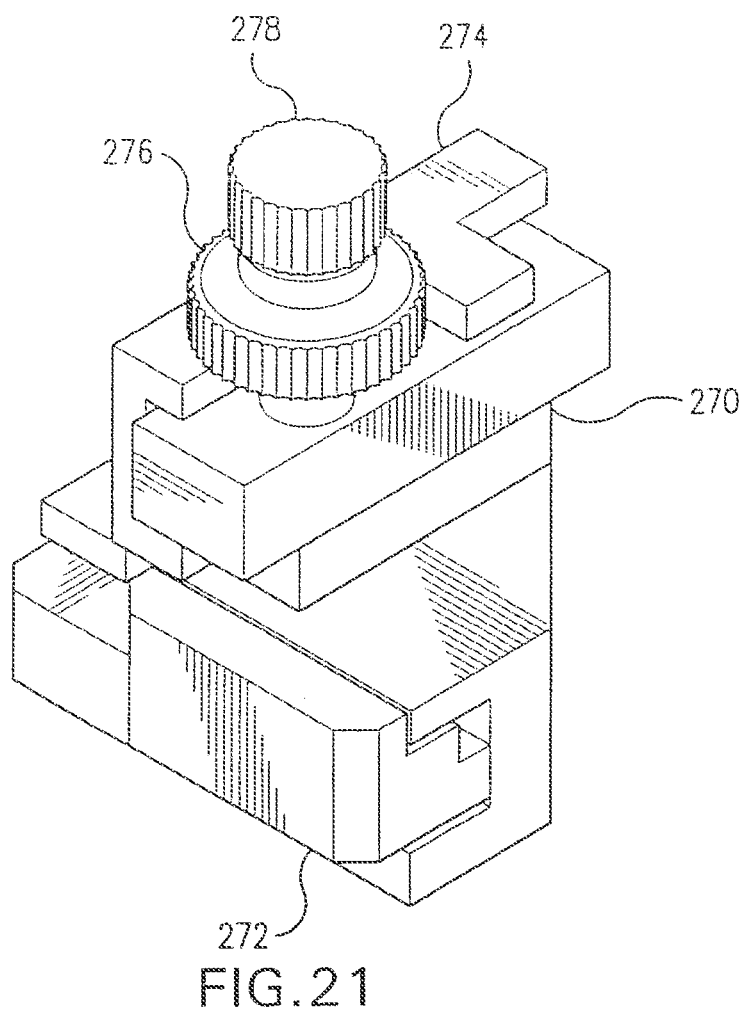
FIG. 21 is a perspective view of a portion of a table orientation control mechanism of the mount subassembly.
Figure 22:
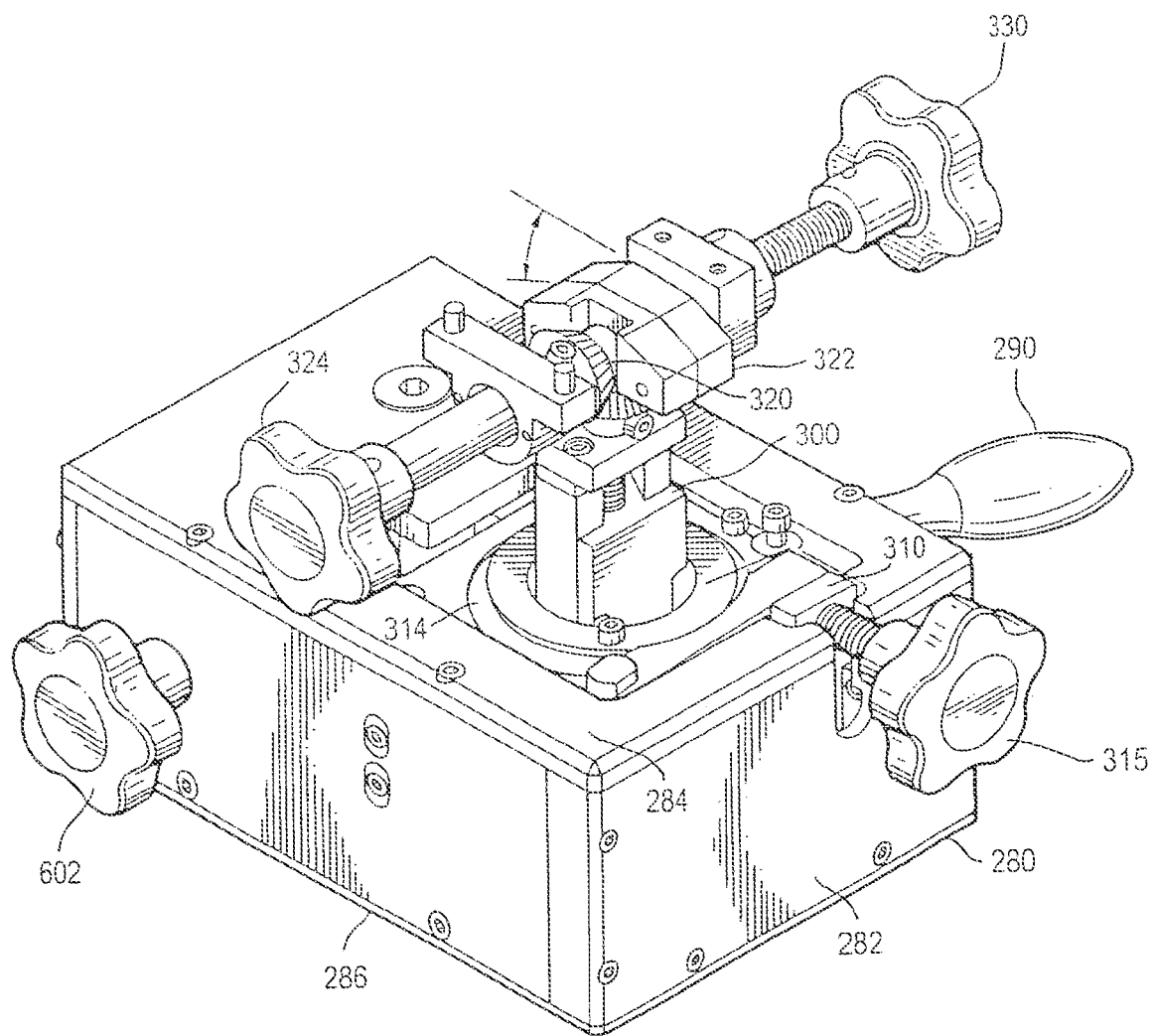
FIG. 22 is a perspective view of a housing of an orientation control mechanism of the small-animal mount assembly, showing a portion of the orientation control mechanism.
Figure 23:
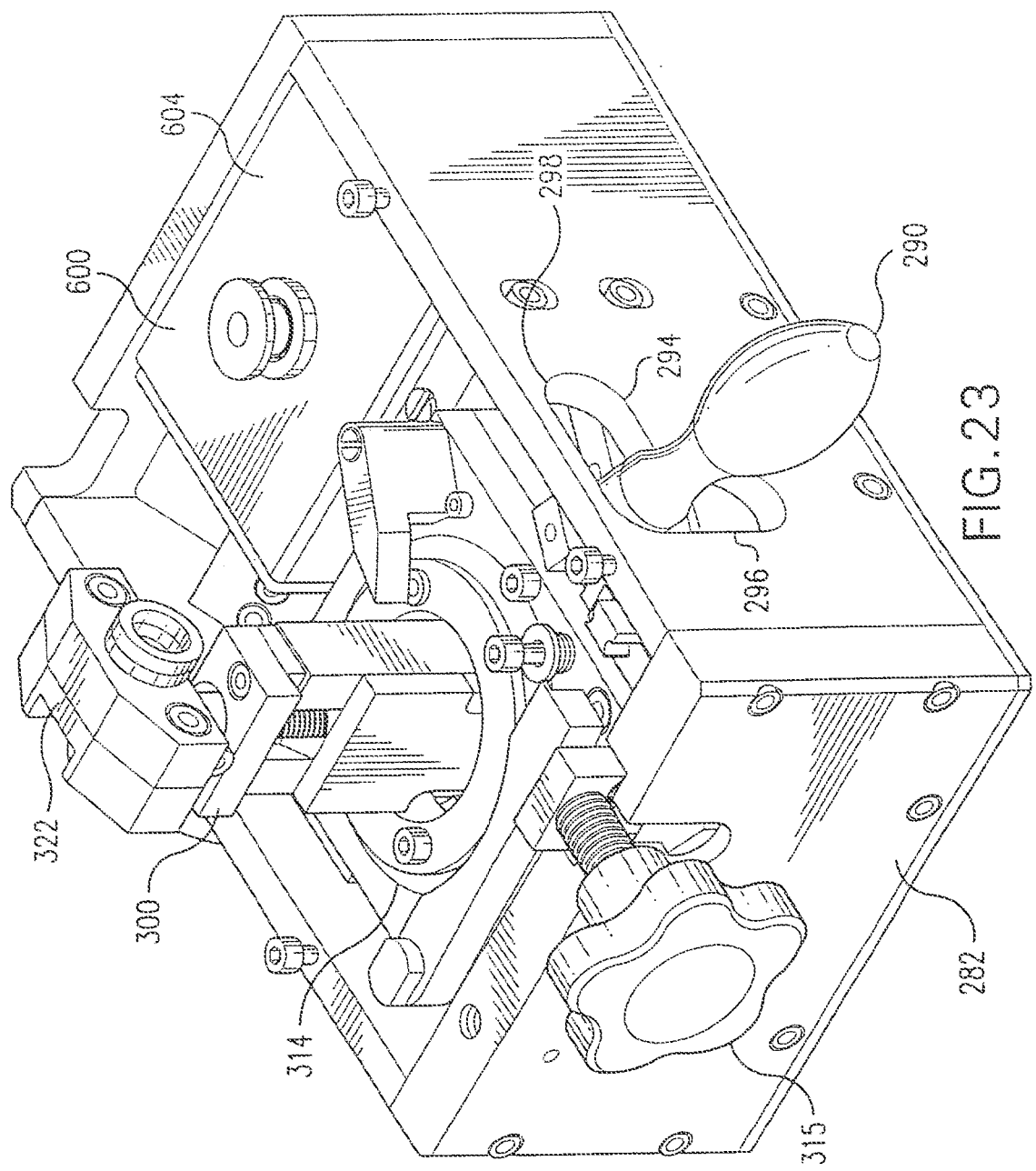
FIG. 23 is a perspective view of a housing of an orientation control mechanism of the small-animal mount assembly, showing a portion of the orientation control mechanism.
Figure 24:
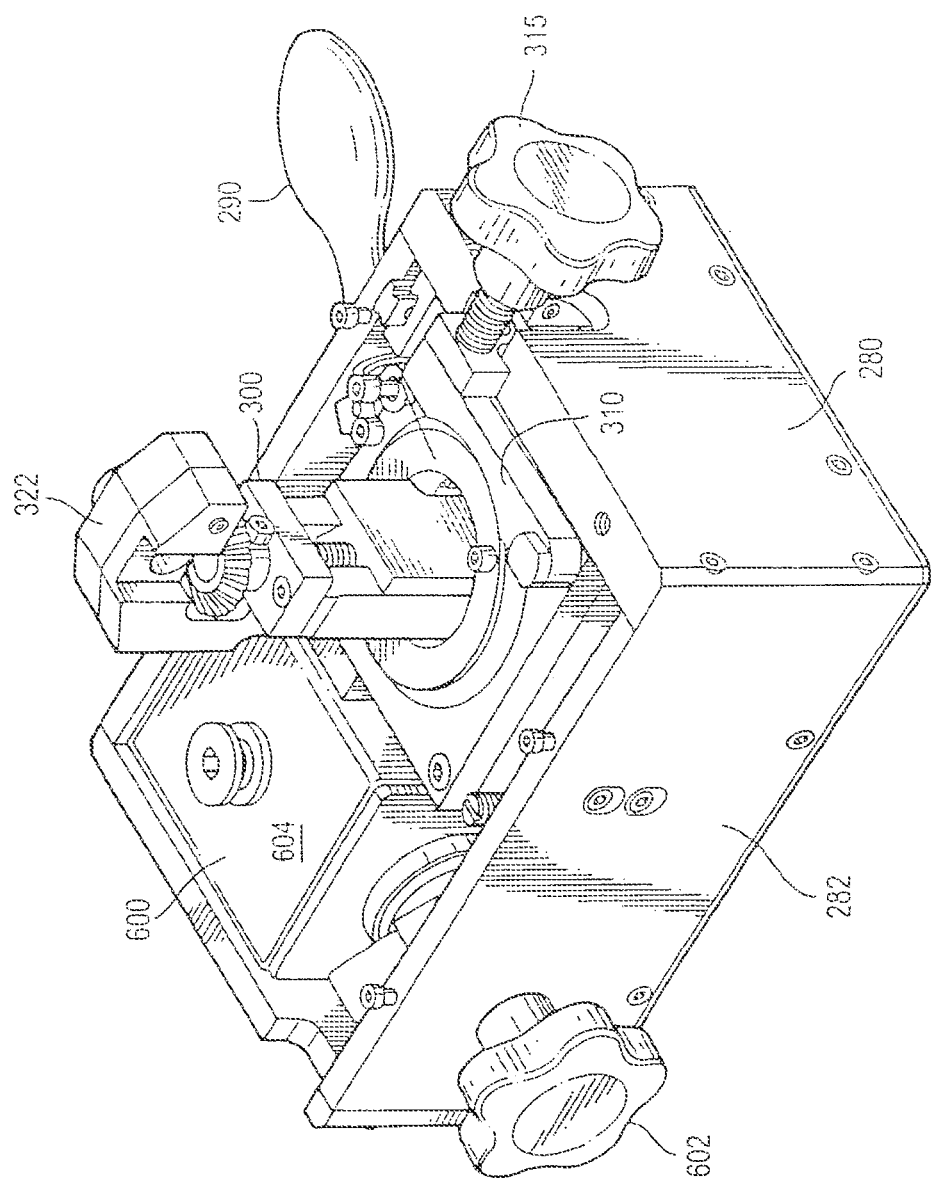
FIG. 24 is a perspective view of a housing of an orientation control mechanism of the small-animal mount assembly, showing a portion of the orientation control mechanism.
Figure 25:
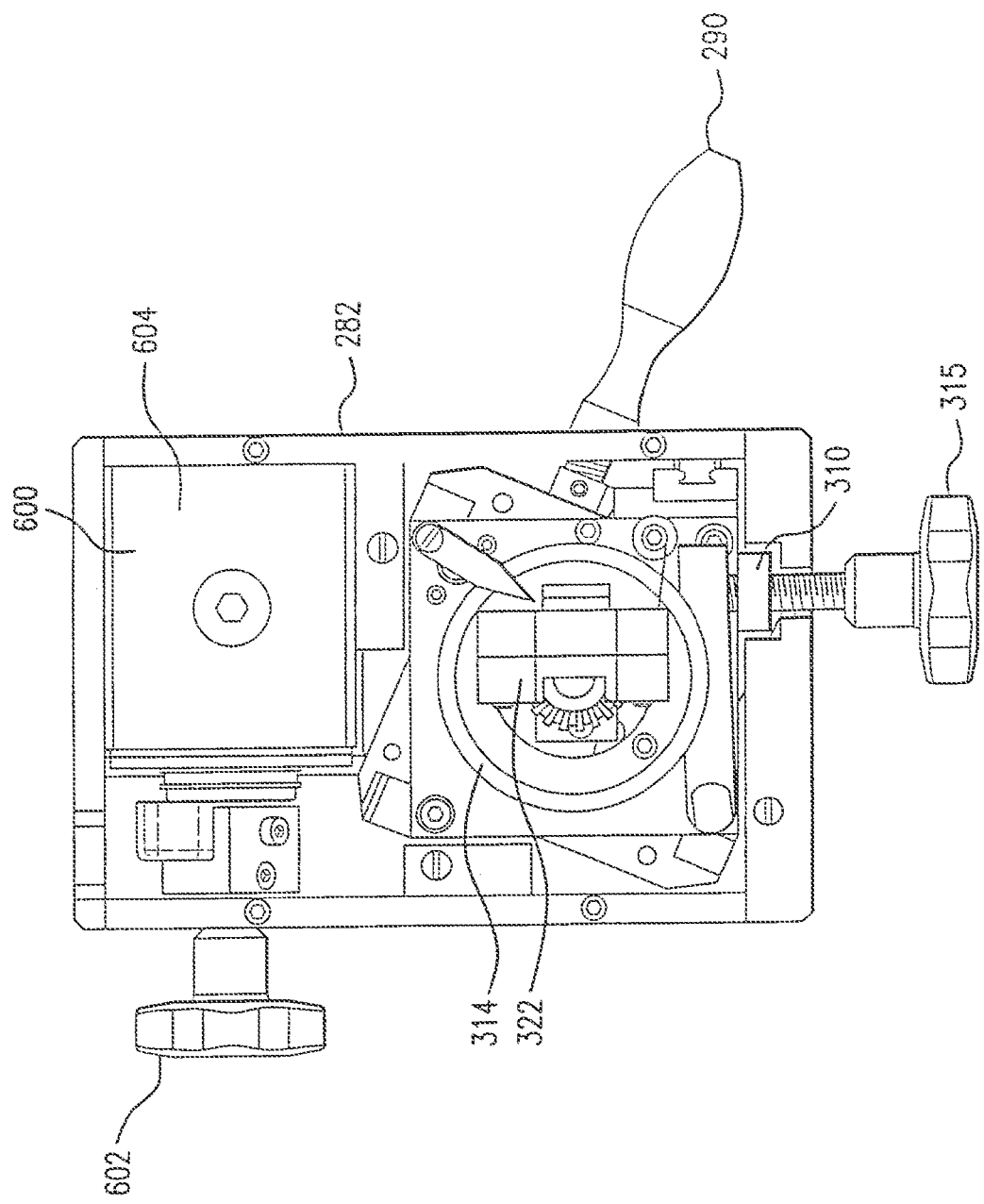
FIG. 25 is a top view of the housing of the orientation control mechanism of FIG. 24.
Figure 26:
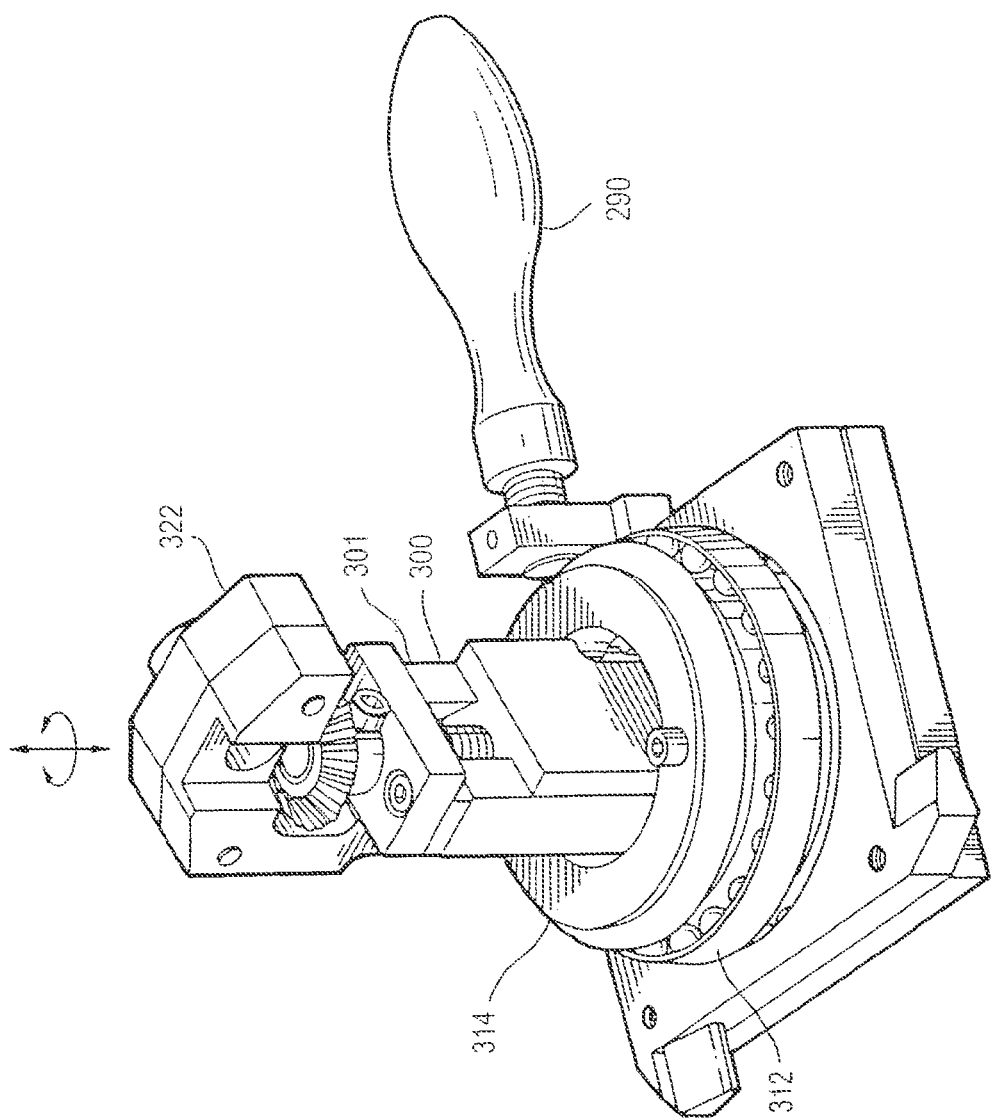
FIG. 26 is a perspective view of a portion of the orientation control mechanism.
Figure 27:
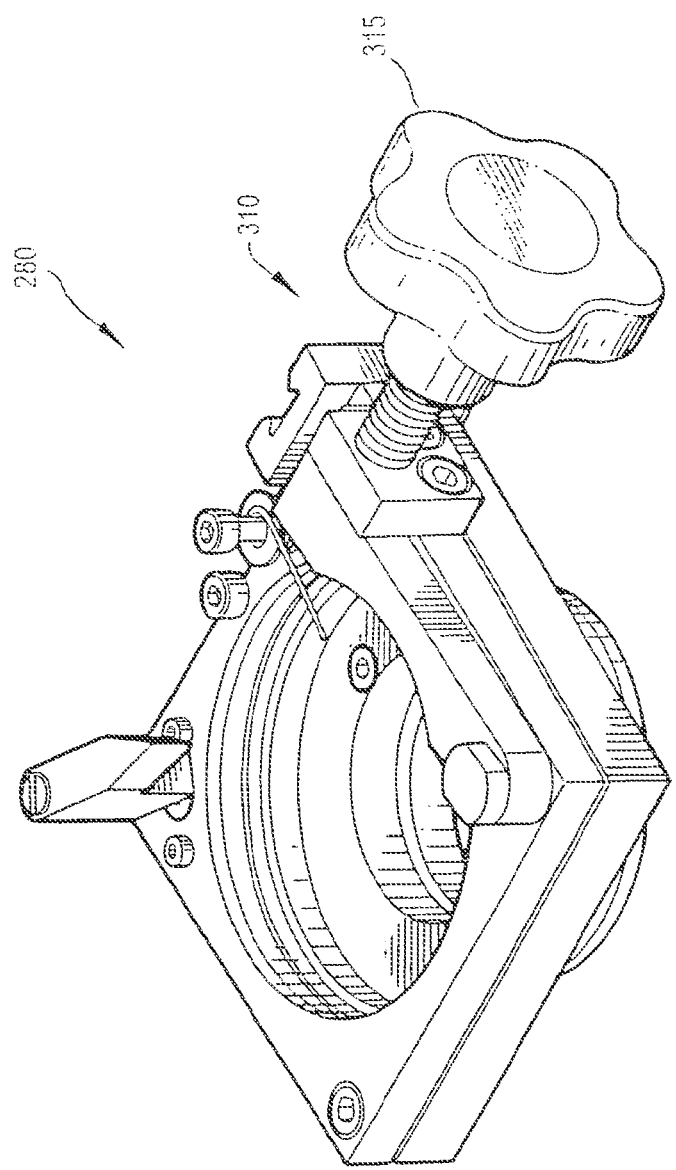
FIG. 27 is a perspective view of a portion of the orientation control mechanism.
Figure 28:
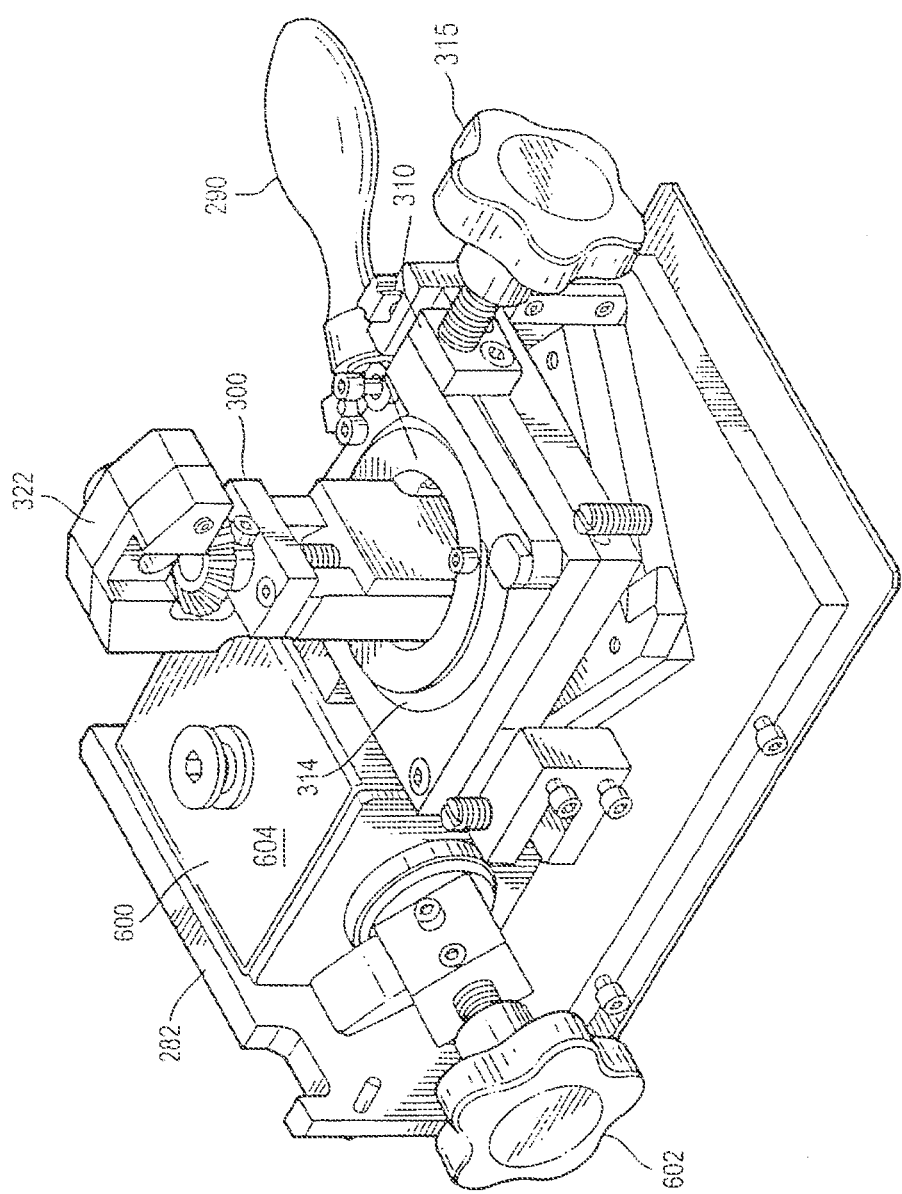
FIG. 28 is a perspective view of a portion of the orientation control mechanism showing portions of the housing removed.
Figure 29:
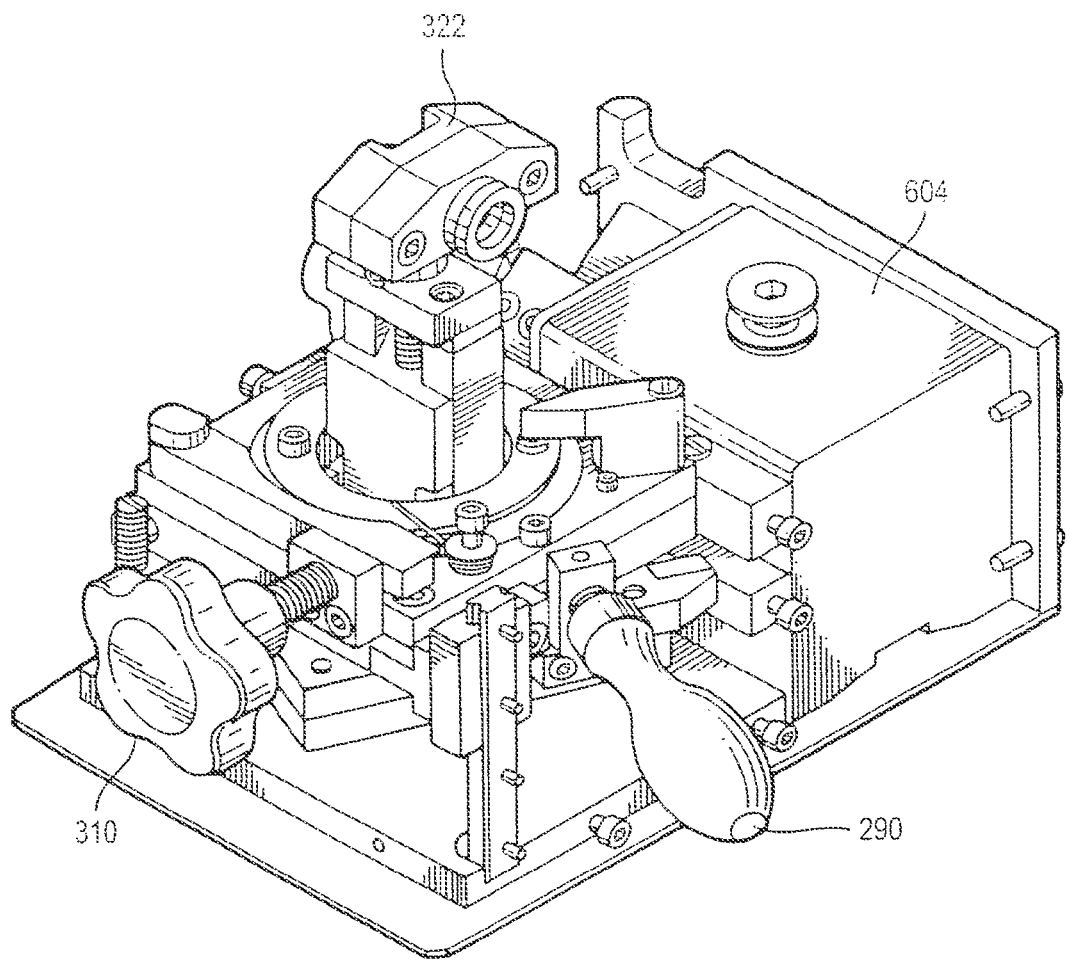
FIG. 29 is a perspective view of a portion of the orientation control mechanism showing portions of the housing removed.
Figure 30:
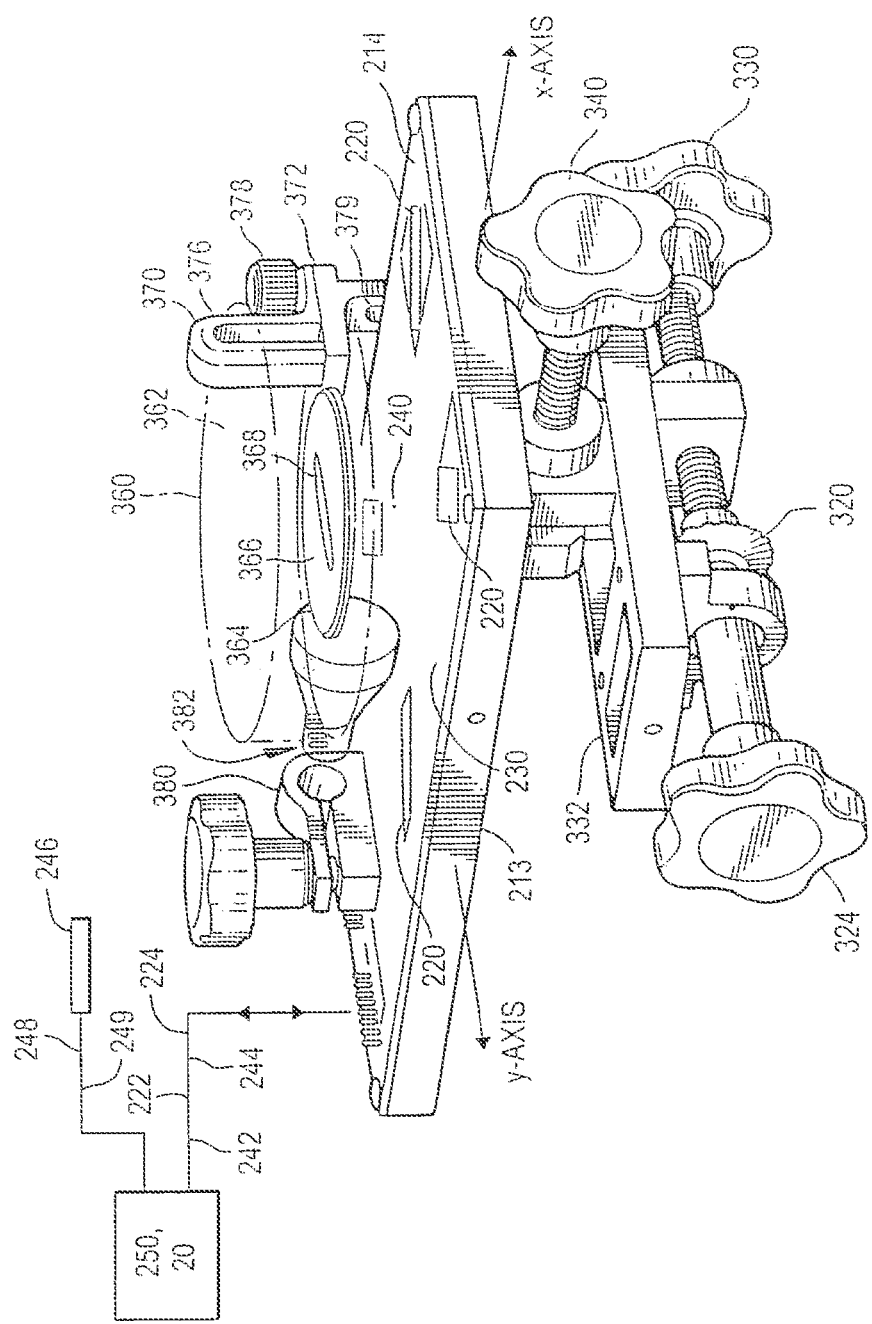
FIG. 30 is a perspective view of a portion of the orientation control mechanism operatively connected to a table member.
Figure 31:
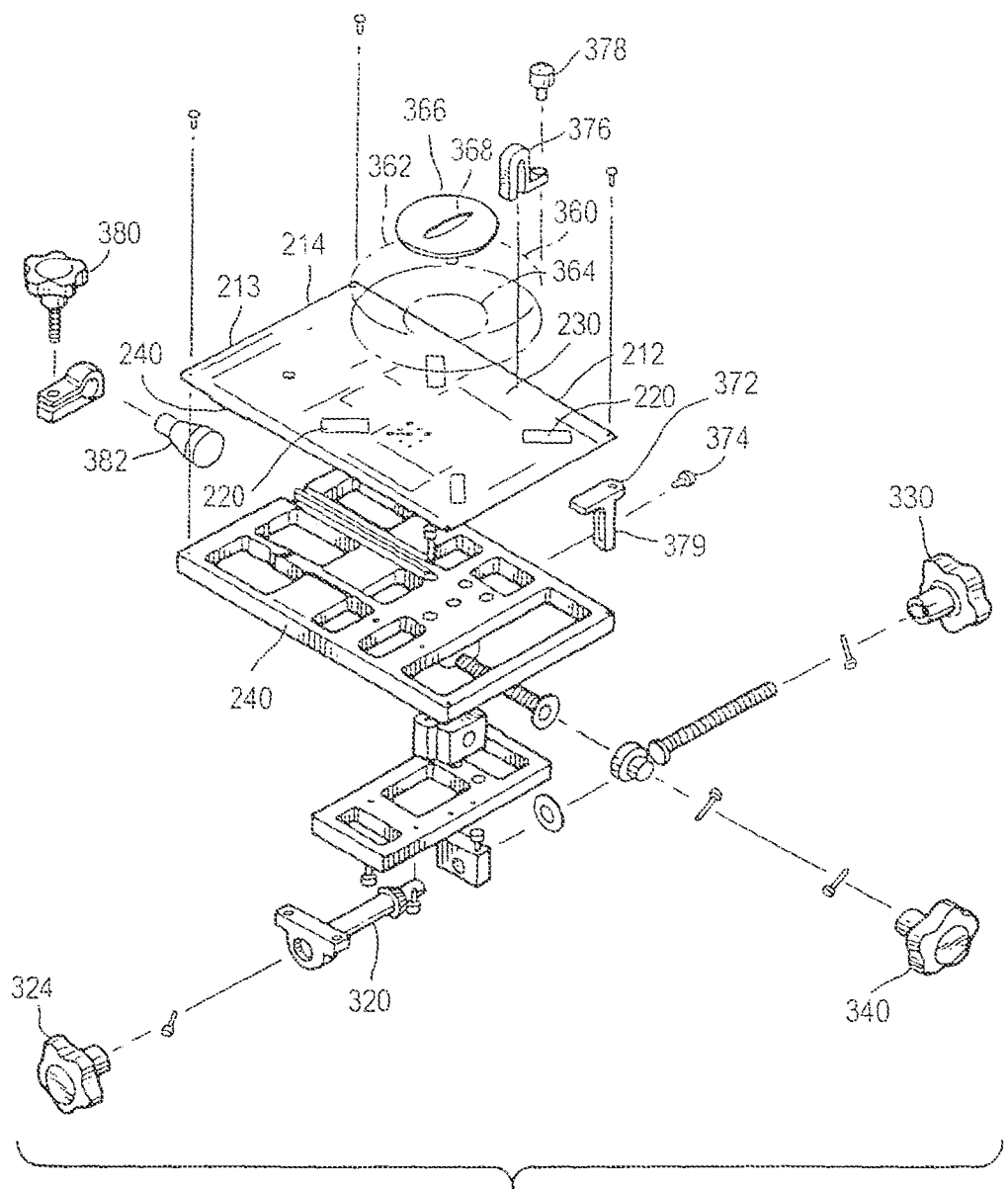
FIG. 31 is an exploded view of FIG. 6.
Figure 32:
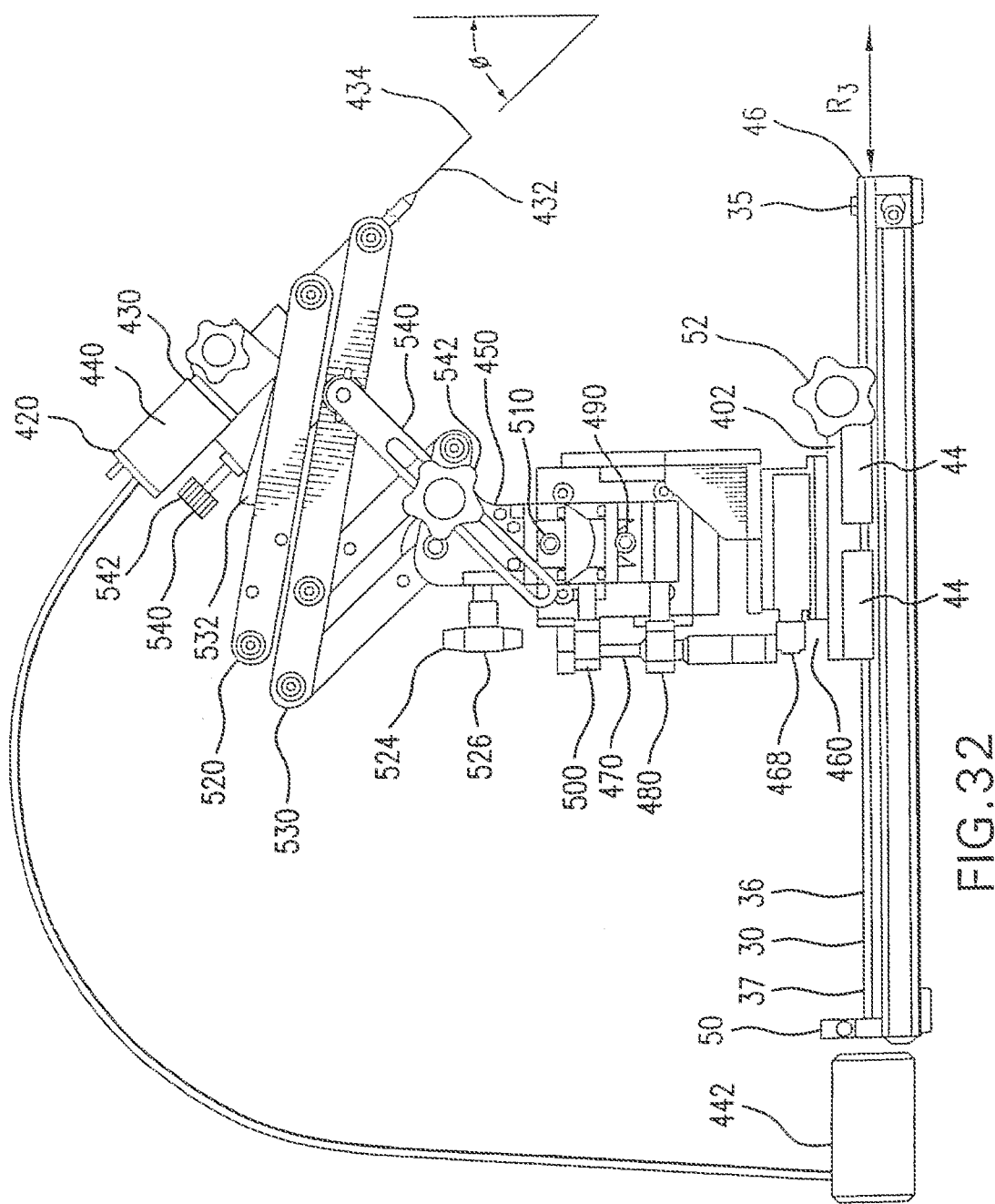
FIG. 32 is a side view of one embodiment of the needle injection assembly mounted onto the third rail, showing an injector subassembly and a carriage subassembly.
Figure 33:
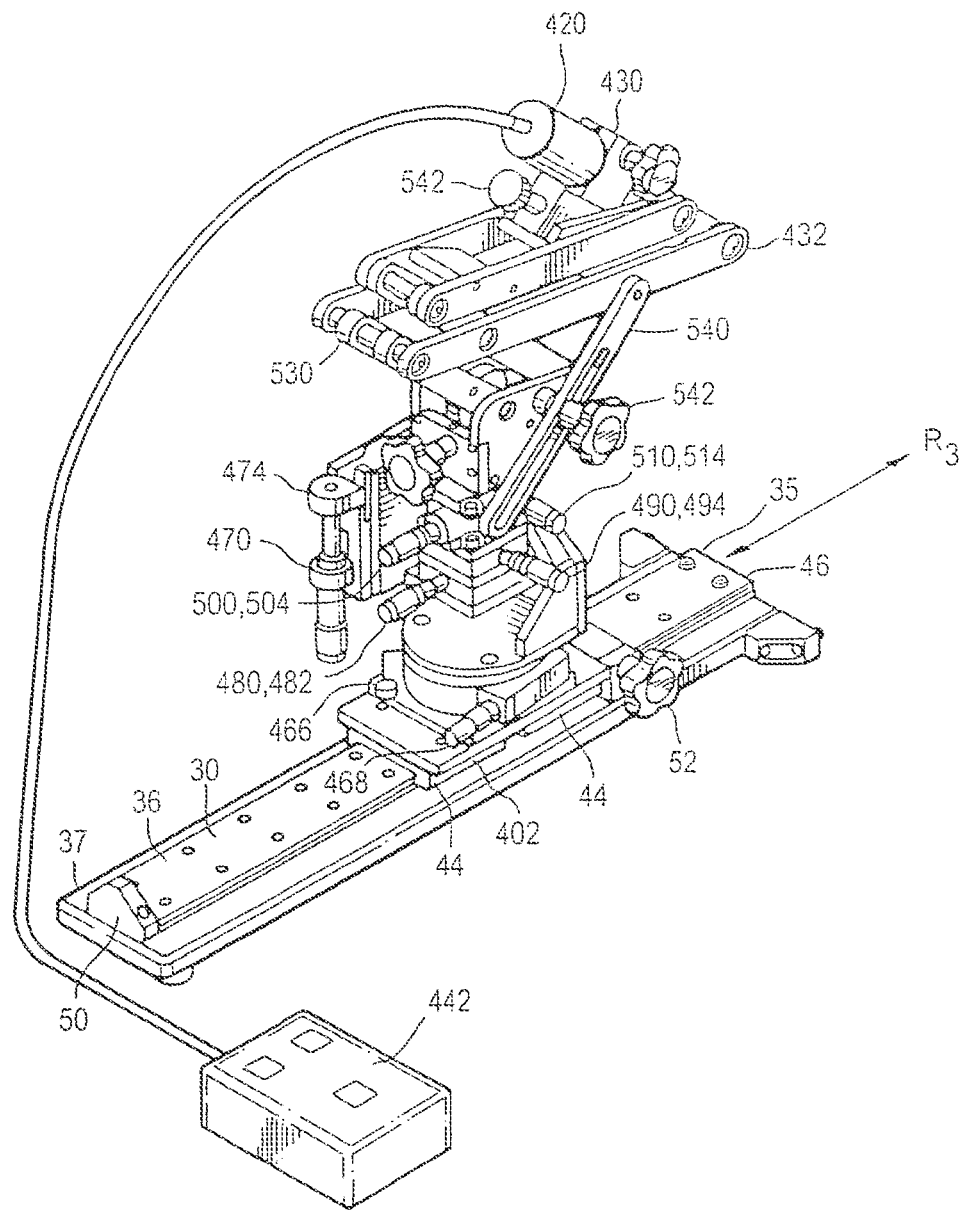
FIG. 33 is a perspective view of the needle injection assembly of FIG. 28.
Figure 34:
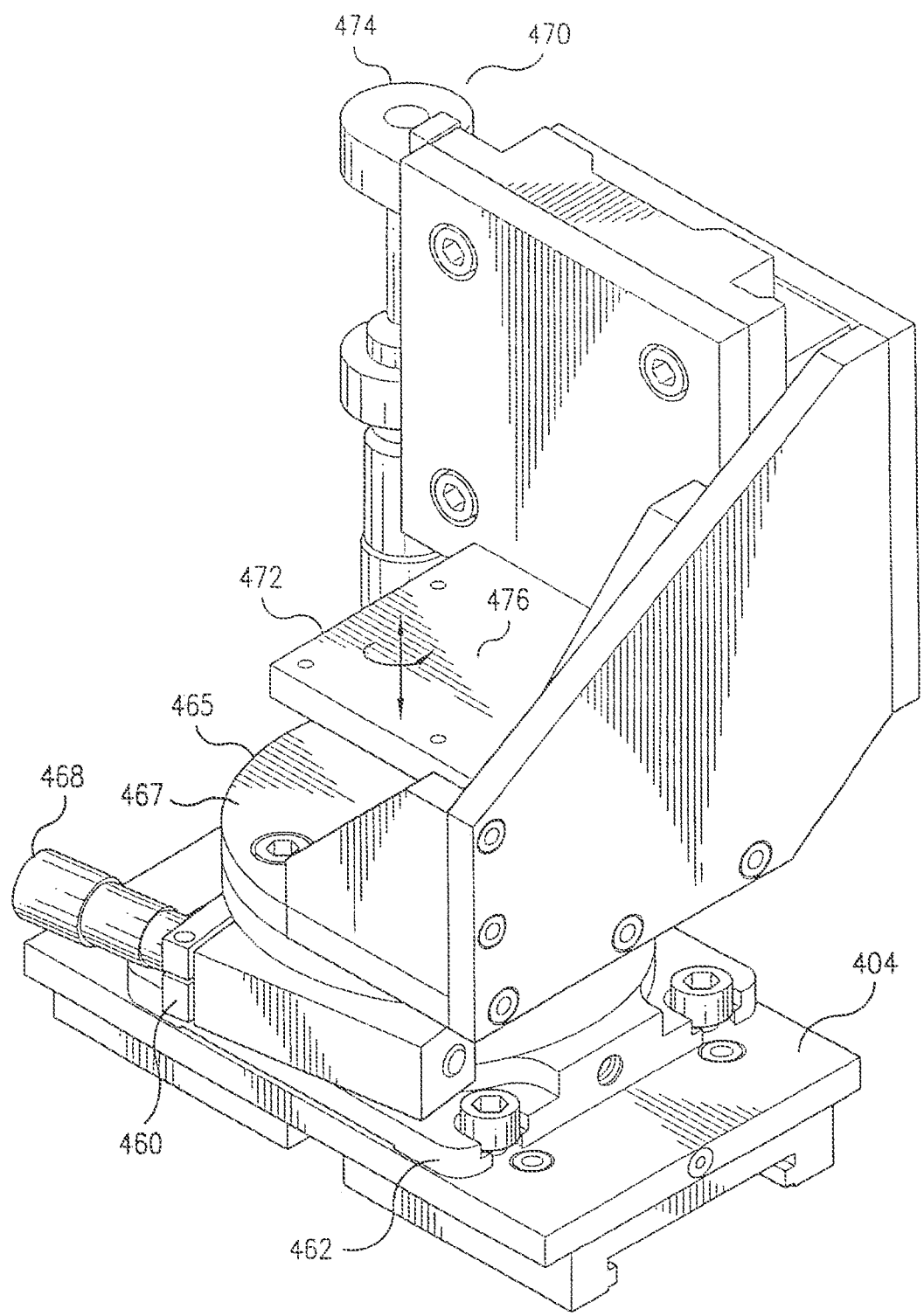
FIG. 34 is a perspective view of a rotation adjustment mechanism and a height adjustment mechanism of the carriage subassembly.
Figure 35:
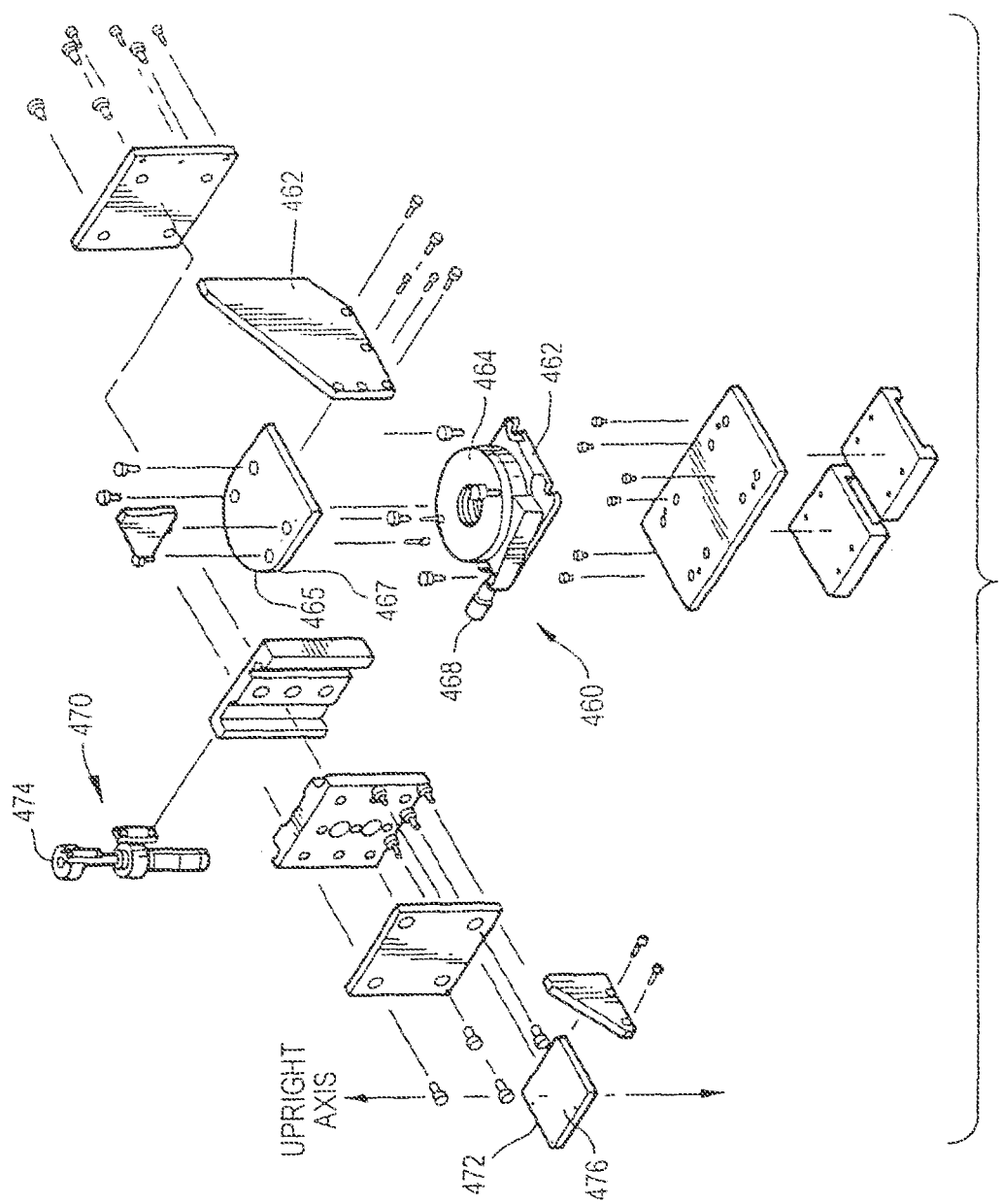
FIG. 35 is an exploded view of the rotation adjustment mechanism and the height adjustment mechanism of FIG. 34.
Figure 36:
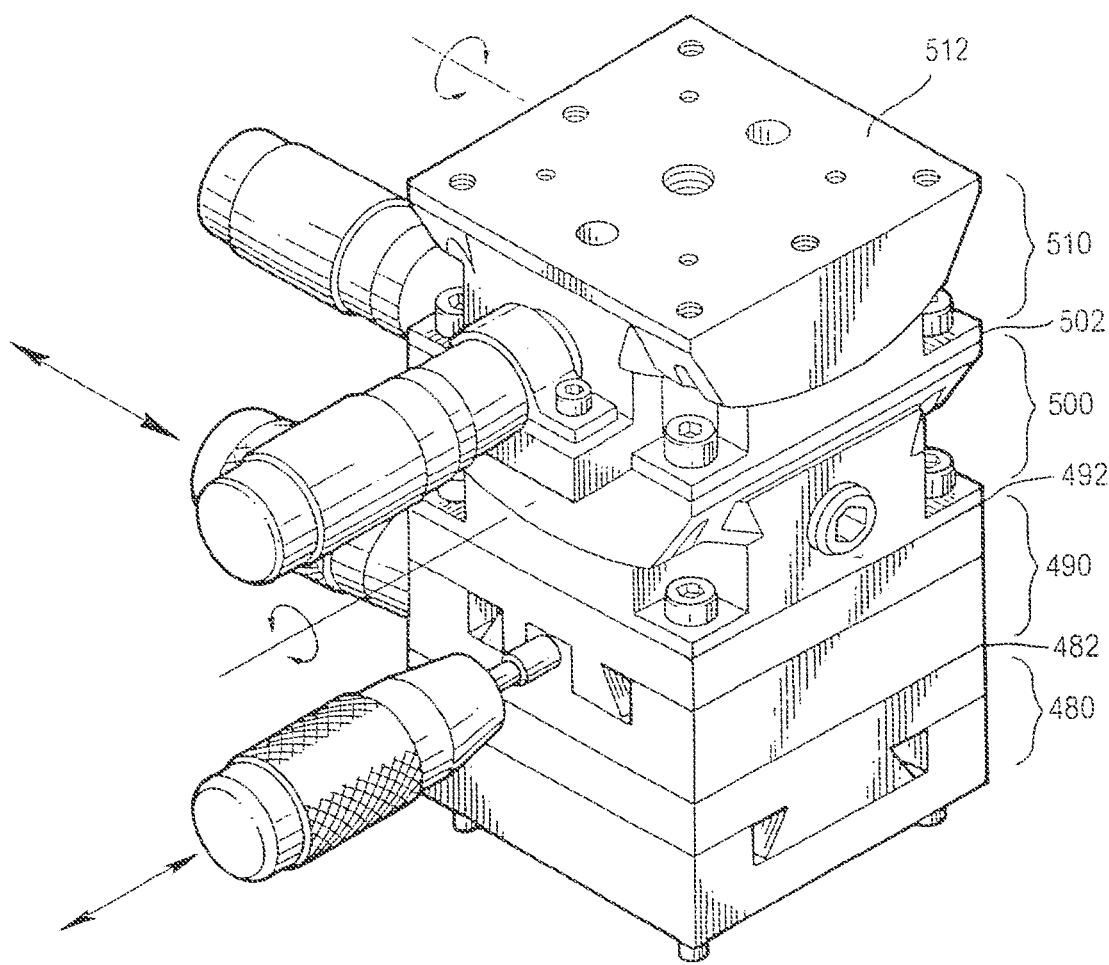
FIG. 36 is a perspective view of a first lateral adjustment mechanism, a second lateral adjustment mechanism, a first tilt adjustment mechanism, and a second tilt adjustment of the carriage subassembly.
Figure 37:
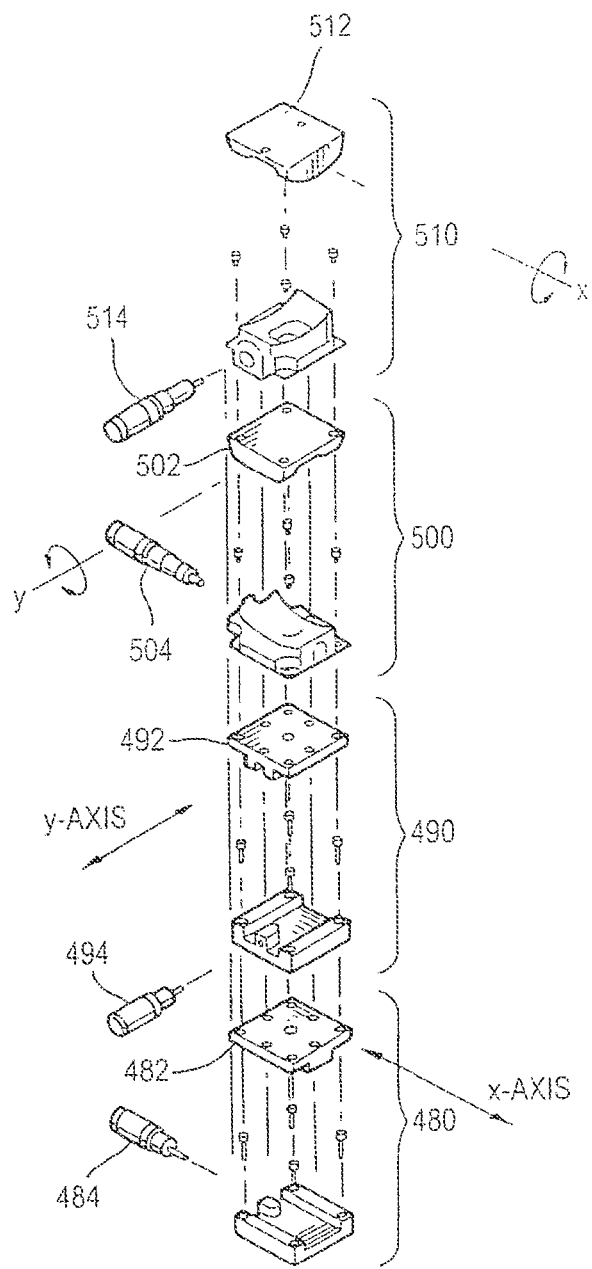
FIG. 37 is an exploded view of the first lateral adjustment mechanism, the second lateral adjustment mechanism, the first tilt adjustment mechanism, and the second tilt adjustment mechanism of FIG. 36.
Figure 38:
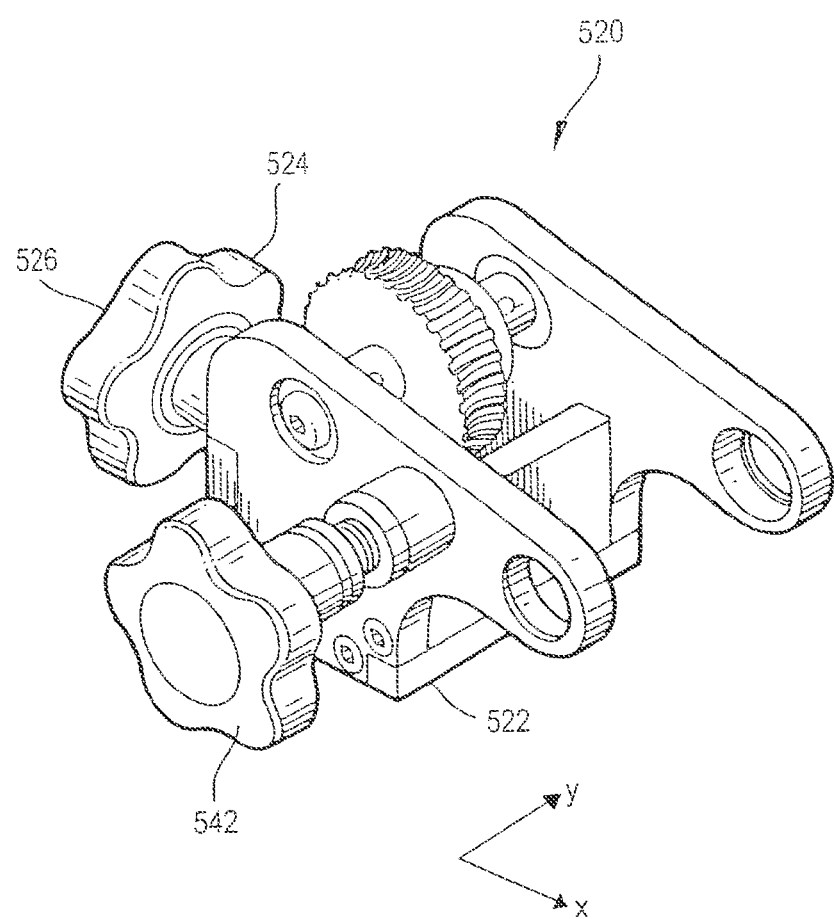
FIG. 38 is a perspective view of a portion of the articulating armature subassembly showing the mount member.
Figure 39:
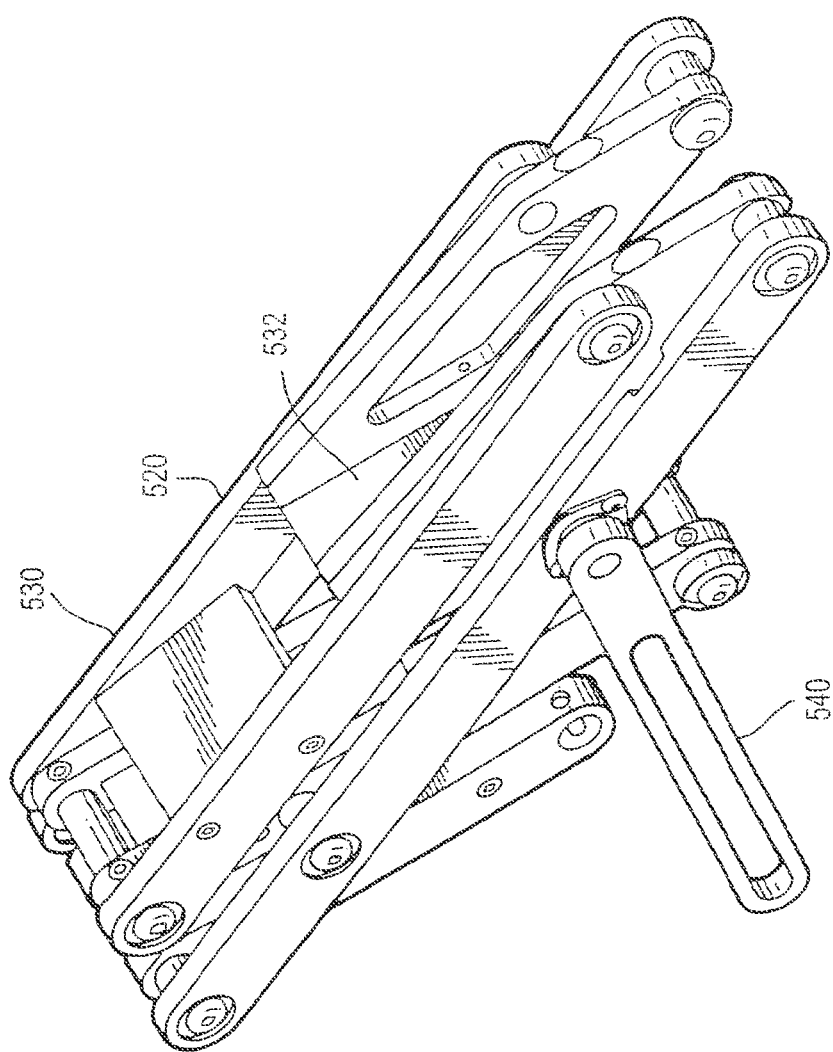
FIG. 39 is a perspective view of a plurality of cooperative aim members of the articulating armature subassembly.
Figure 40:
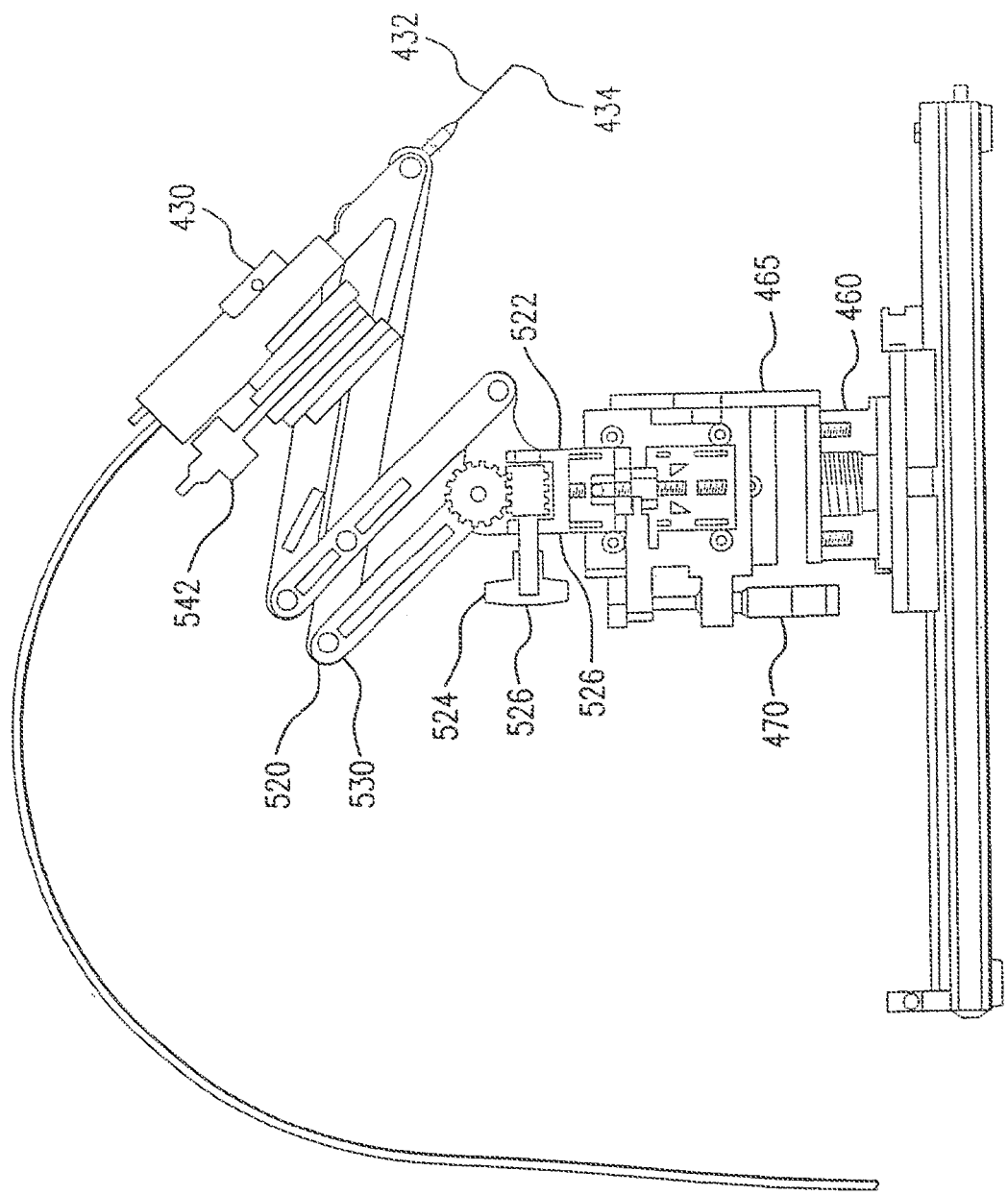
FIG. 40 is a partial cross-sectional view of needle injection assembly.
Figure 41:
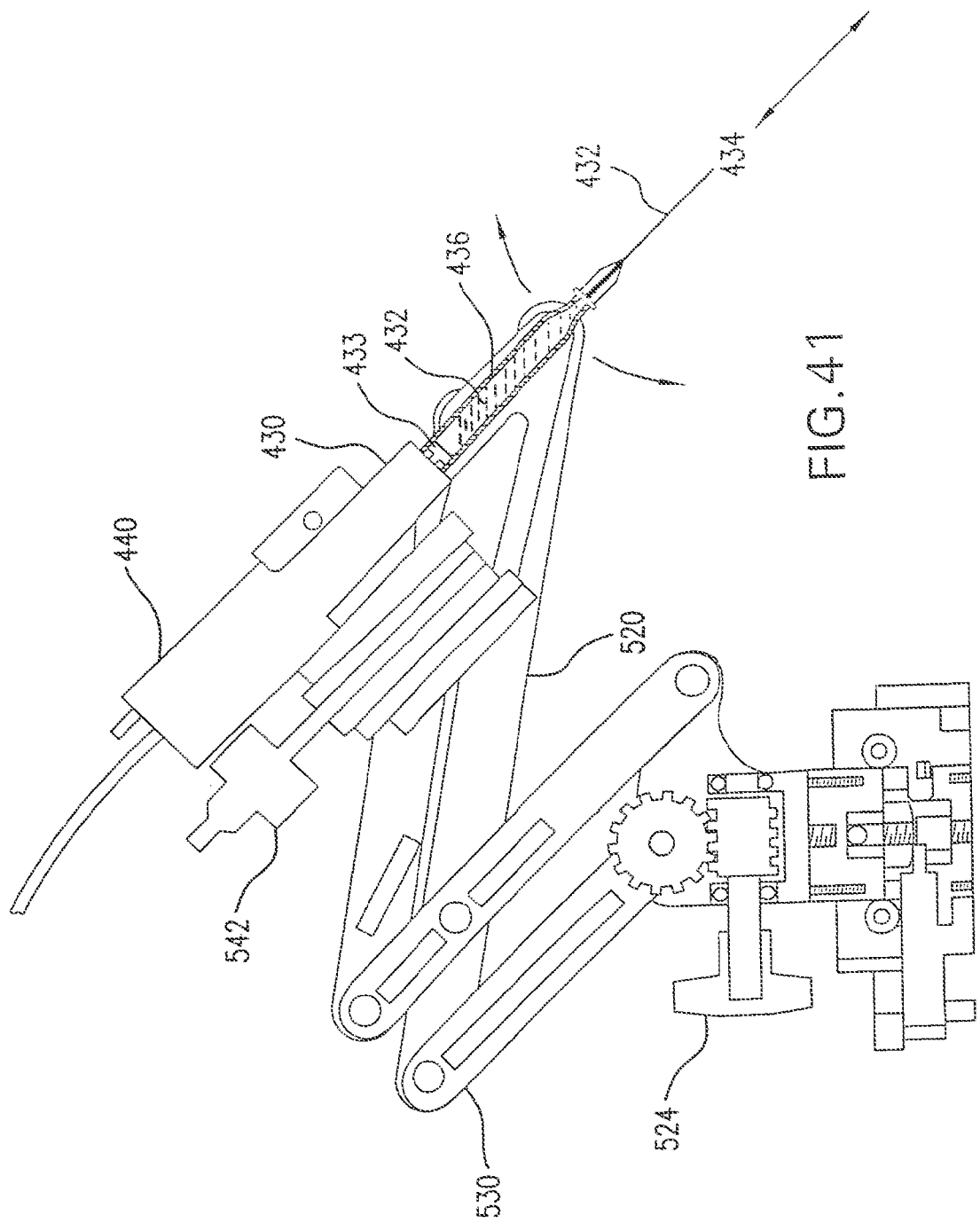
FIG. 41 is a partial cross-sectional view of a portion of the injector unit.
Figure 42:
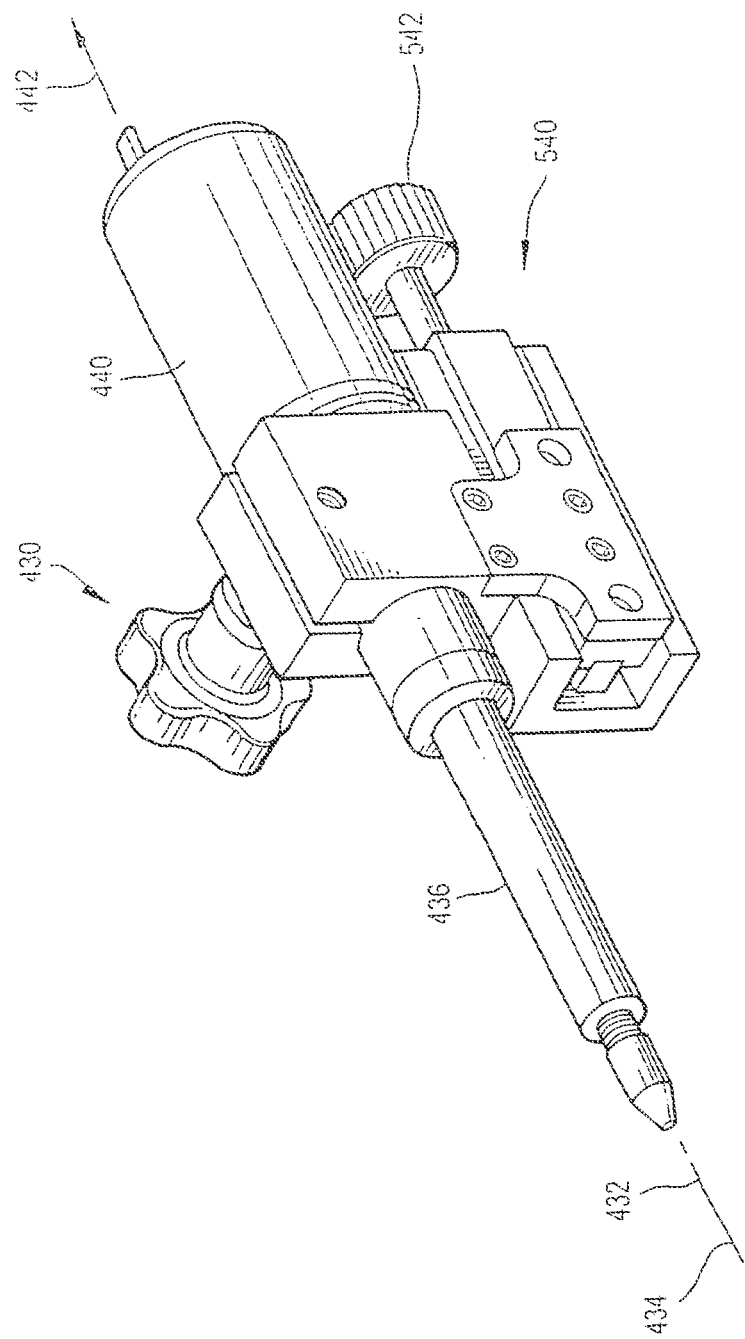
FIG. 42 is a perspective view of an injector unit of the injector subassembly.
Figure 43:
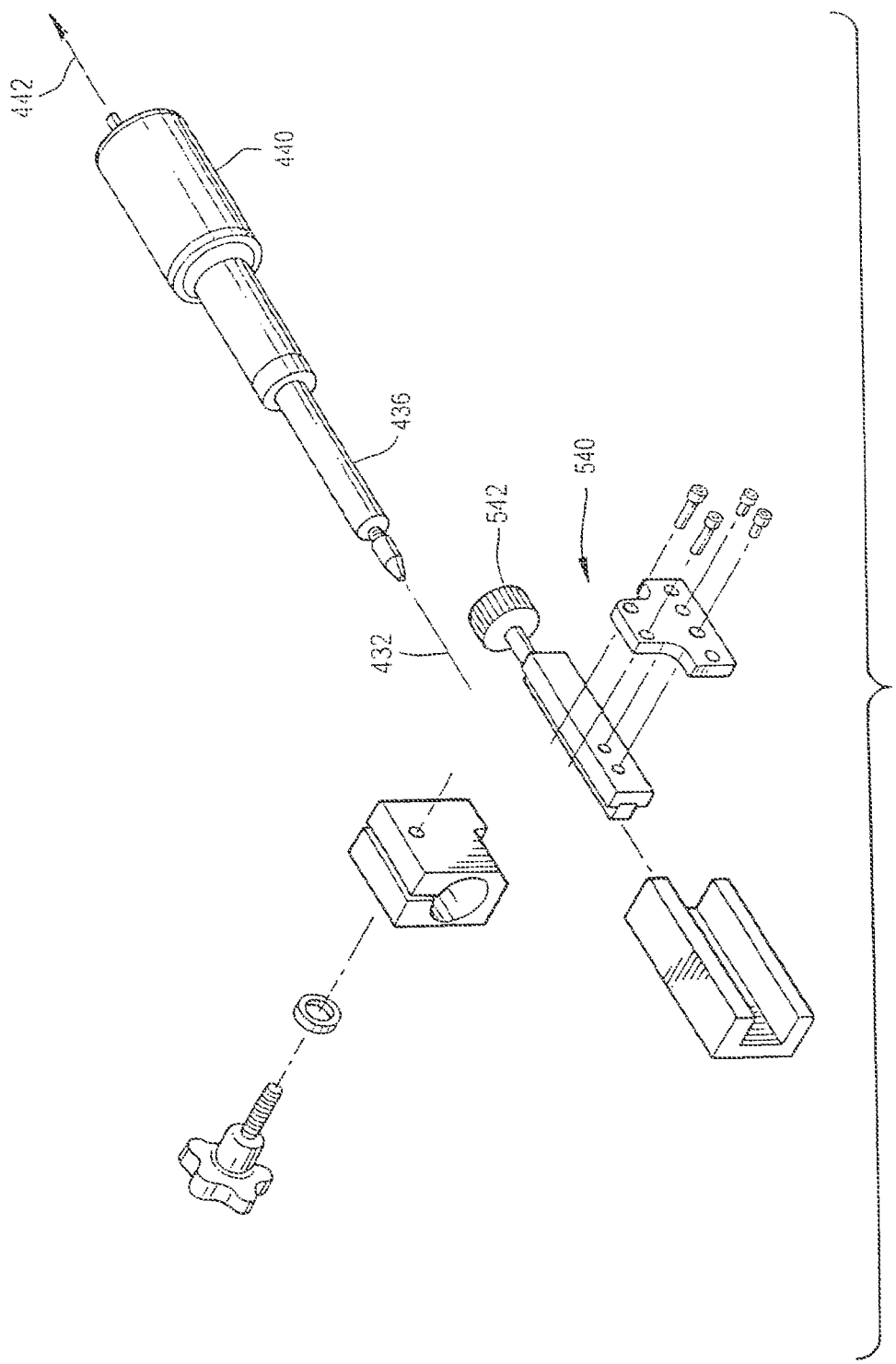
FIG. 43 is an exploded view of the injector unit of FIG. 42.
Figure 44:
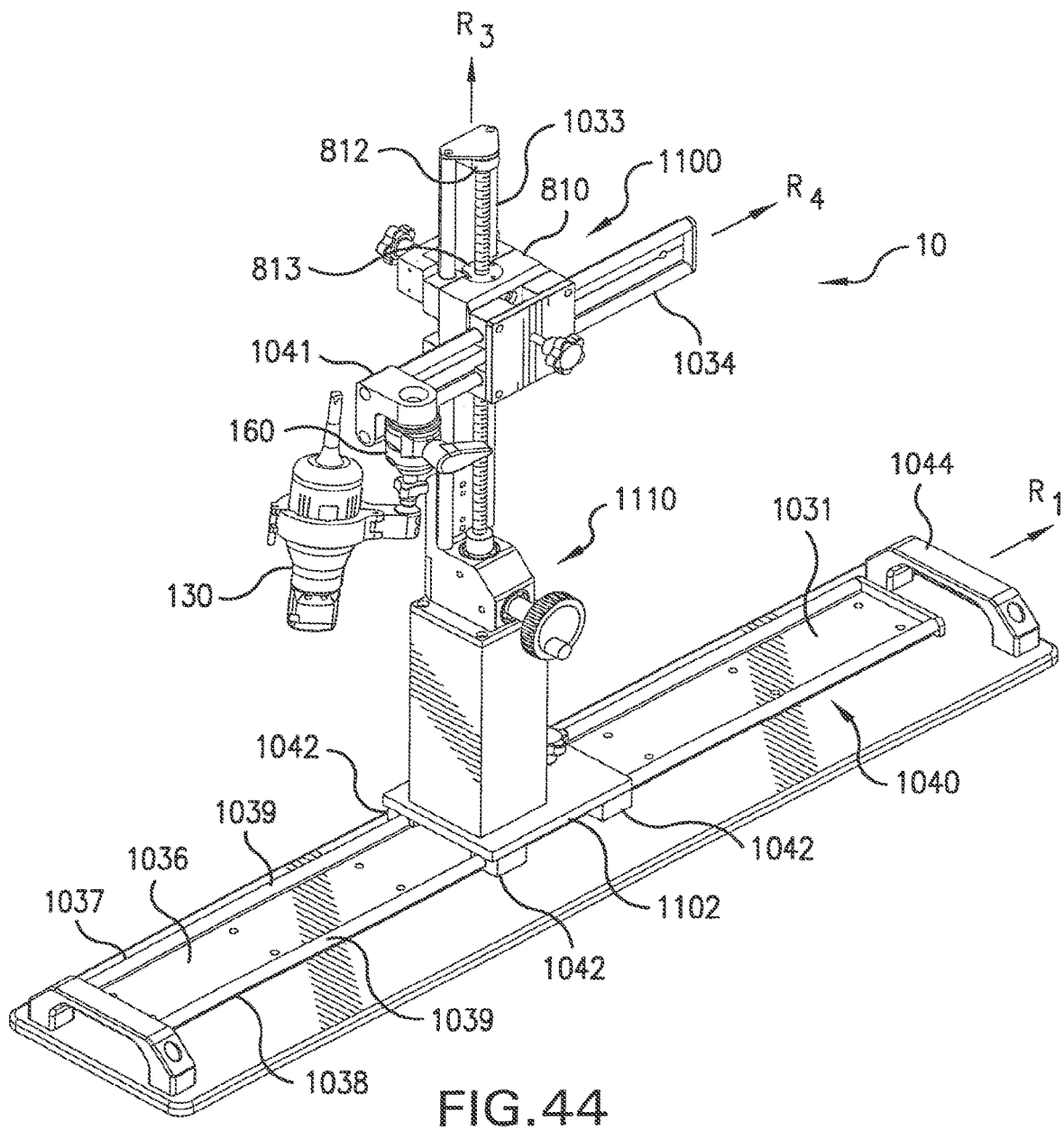
FIG. 44 is a perspective view of one embodiment of a small-animal imaging system of the present invention, showing a scanhead assembly mounted onto a first rail
Figure 45:
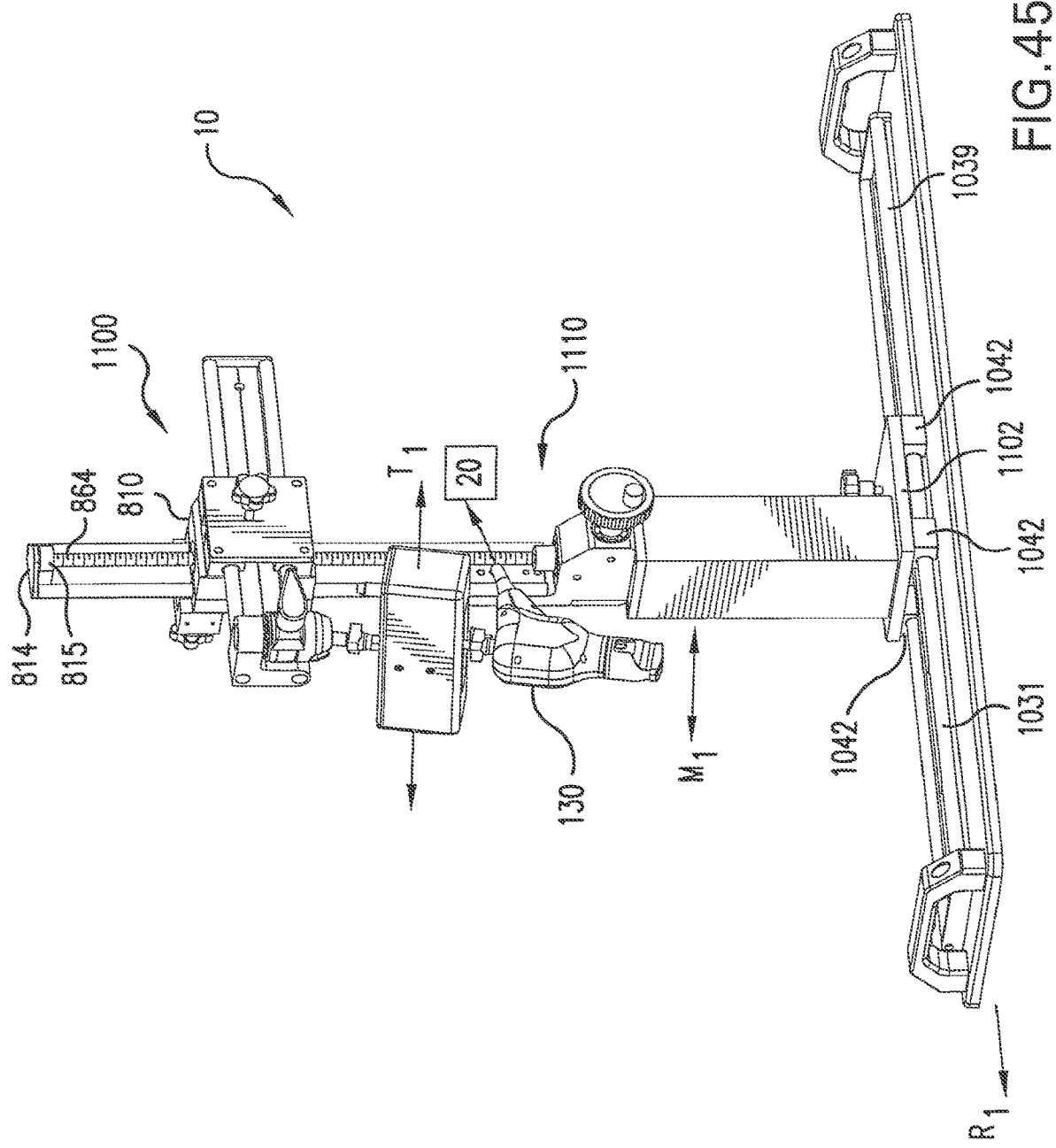
FIG. 45, is a perspective view of the scanhead assembly of FIG. 40 showing a scanhead articulation unit attached to a scanhead unit.
Figure 46:
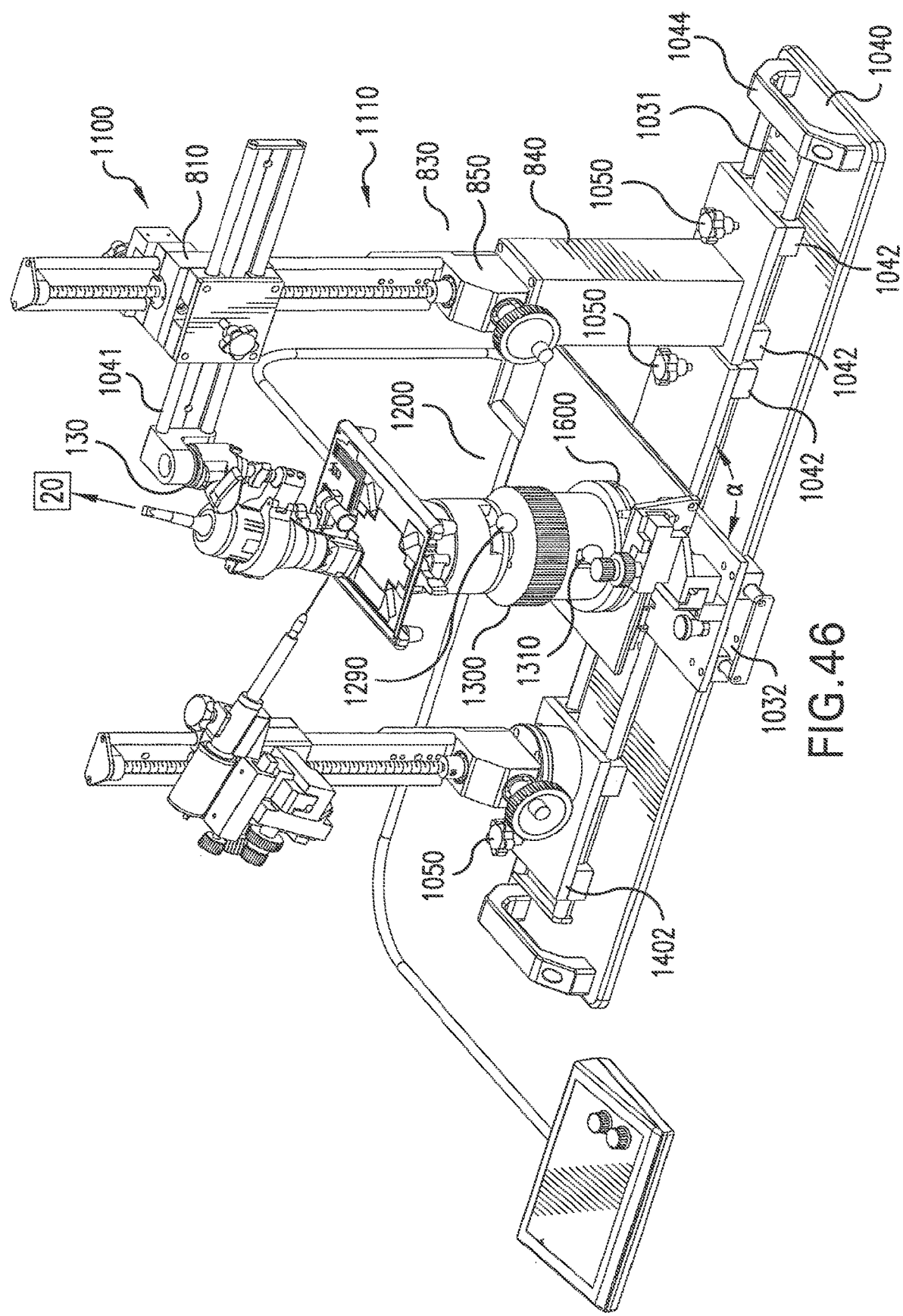
FIG. 46 is a perspective view of an alternative embodiment of a small-animal imaging system of the present invention, showing a scanhead assembly mounted onto a first rail, a small-animal mount assembly mounted onto a second rail, and a needle injection assembly mounted onto the first rail.
Figure 47:
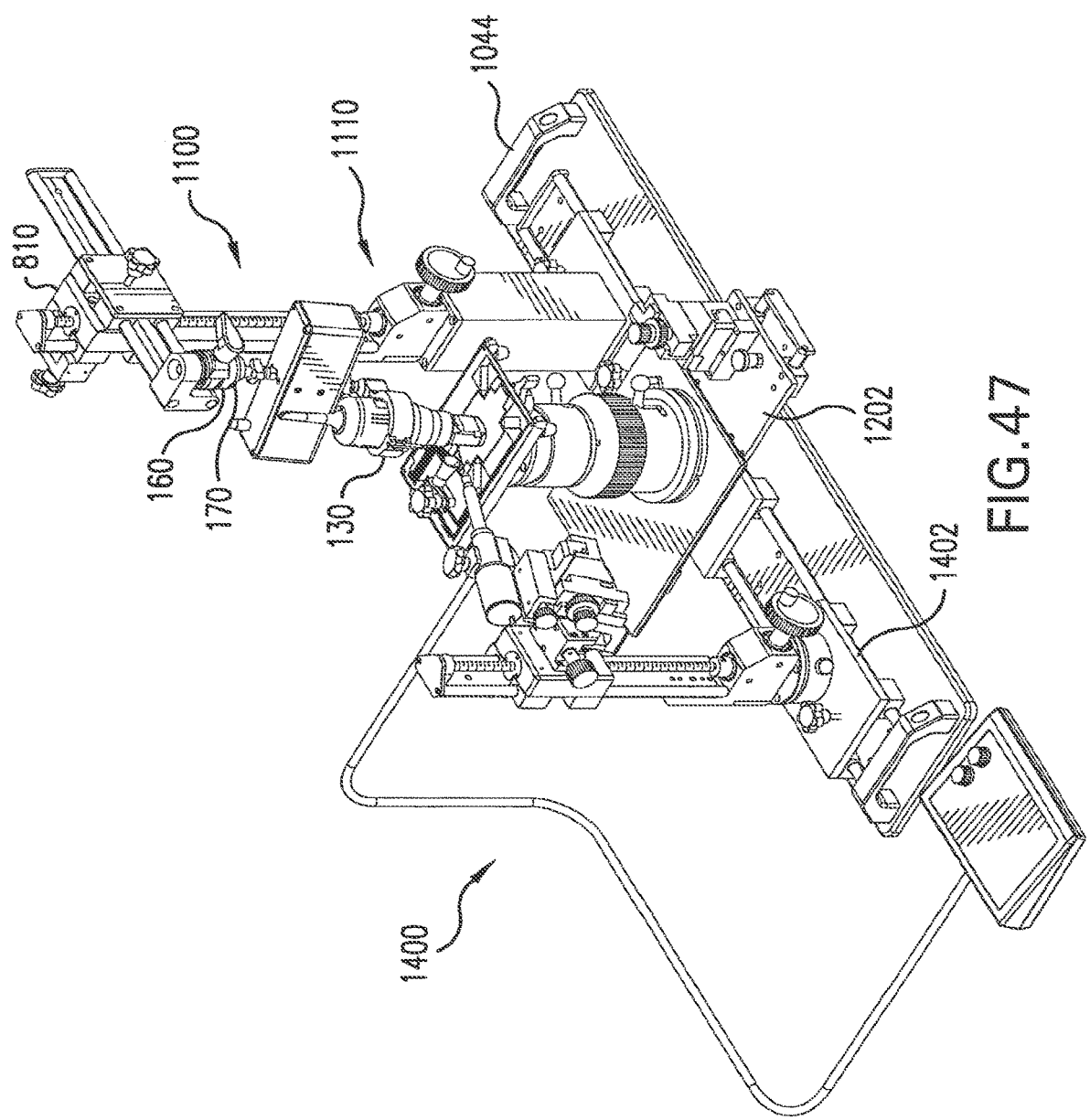
FIG. 47 is a perspective schematic view of the small-animal imaging system of FIG. 46 showing a scanhead articulation unit attached to a scanhead unit.
Figure 48:
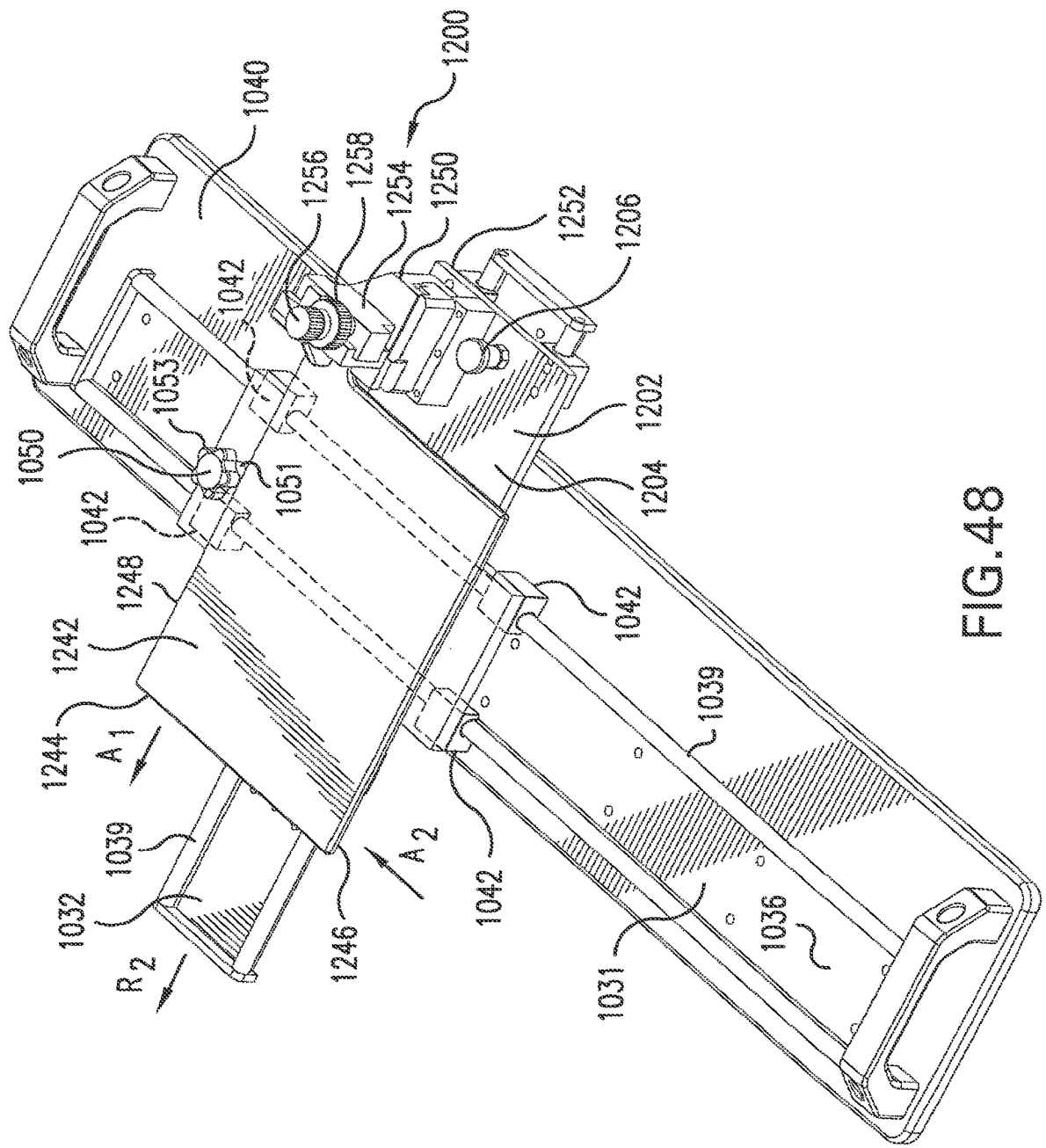
FIG. 48 is a semi-transparent layered perspective view of the second rail movable mounted to the first rail and the planar platform of the mount subassembly.
Figure 49:
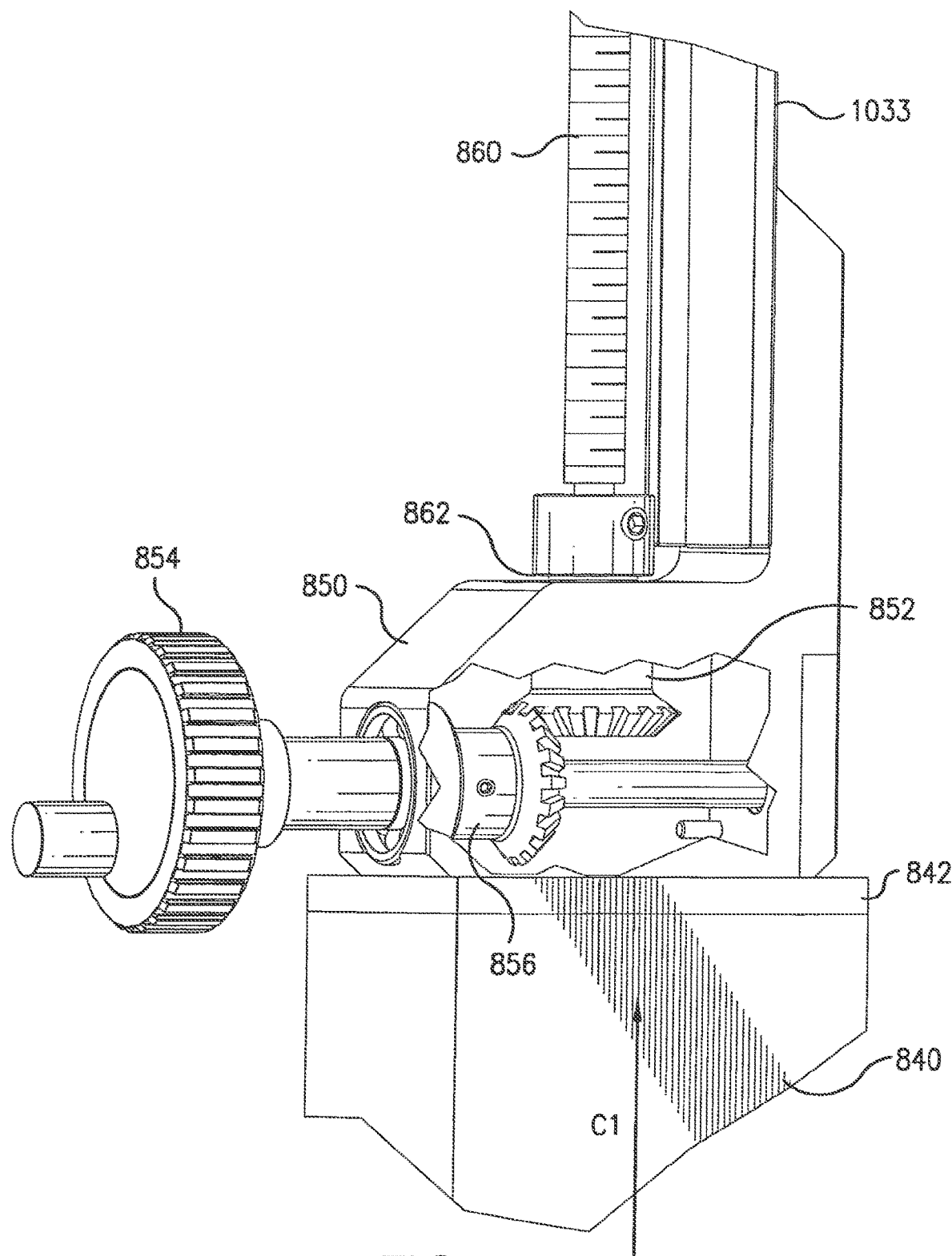
FIG. 49 is a partial semi-transparent layered perspective view of the height adjustment mechanism of the scanhead assembly.
Figure 50:
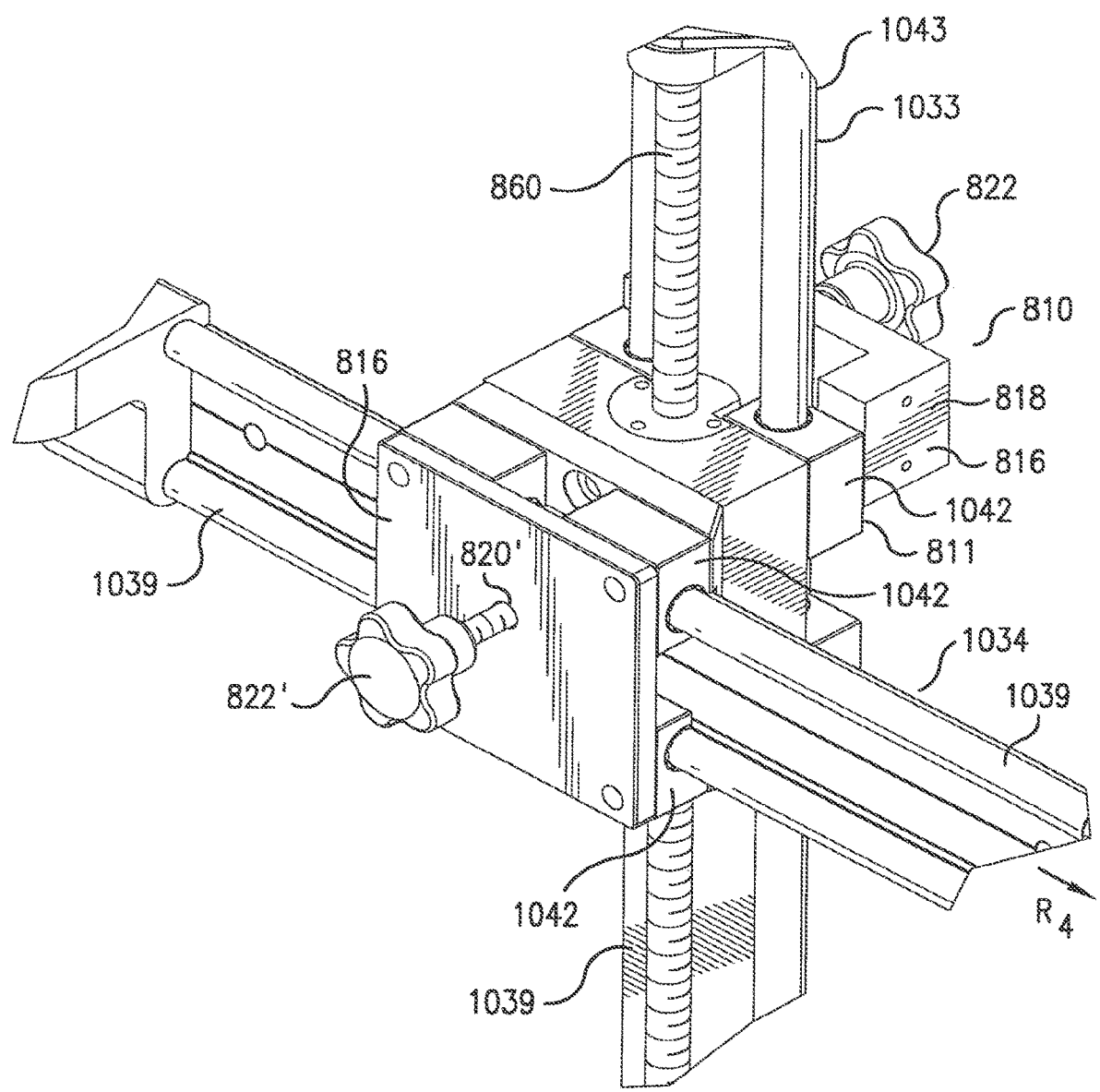
FIG. 50 is a partial semi-transparent layered perspective view of the cantilever mount member of the scanhead assembly.
Figure 51:
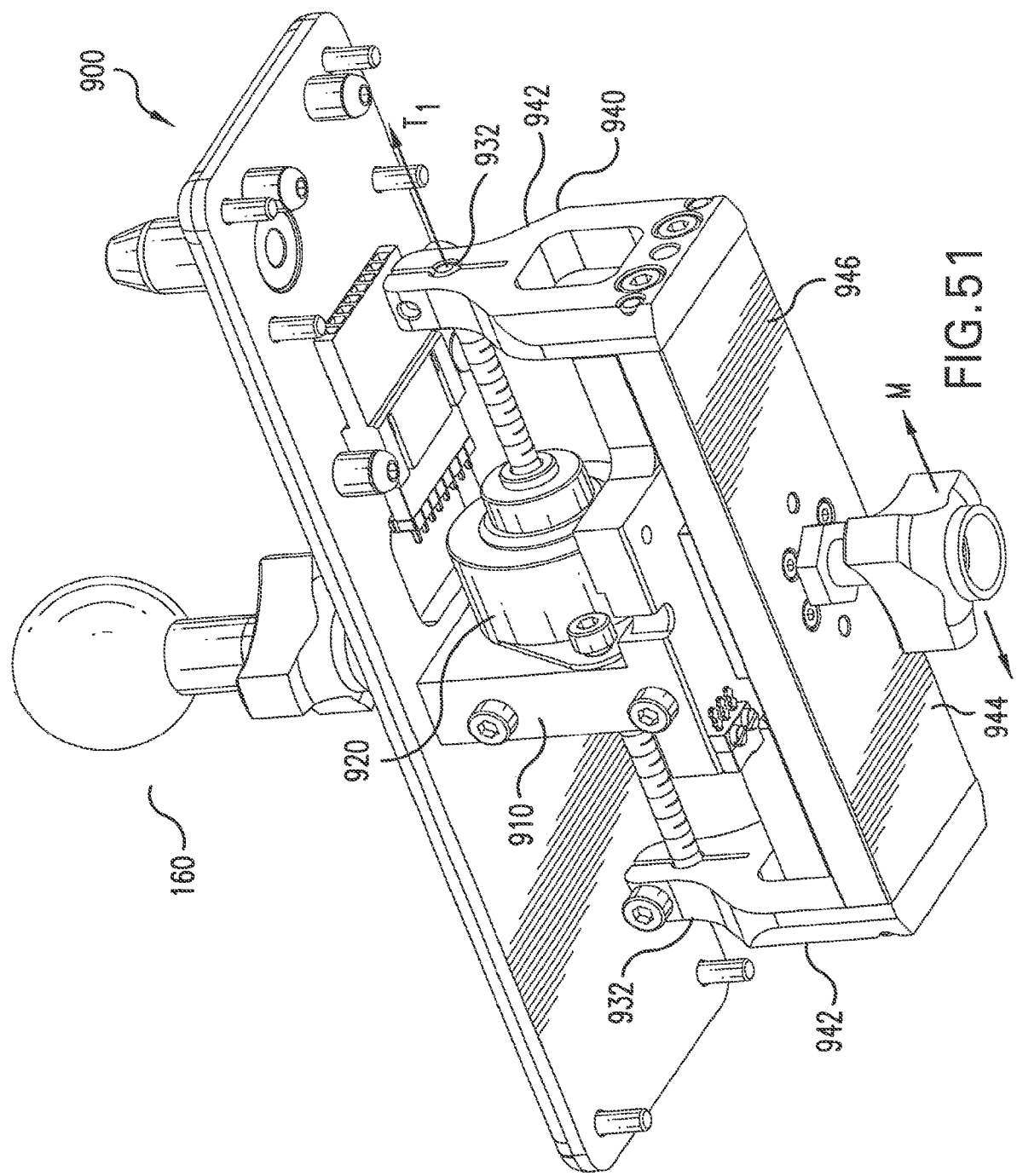
FIG. 51 is a partial bottom perspective view of the scanhead articulation unit of the present invention.
Figure 52:
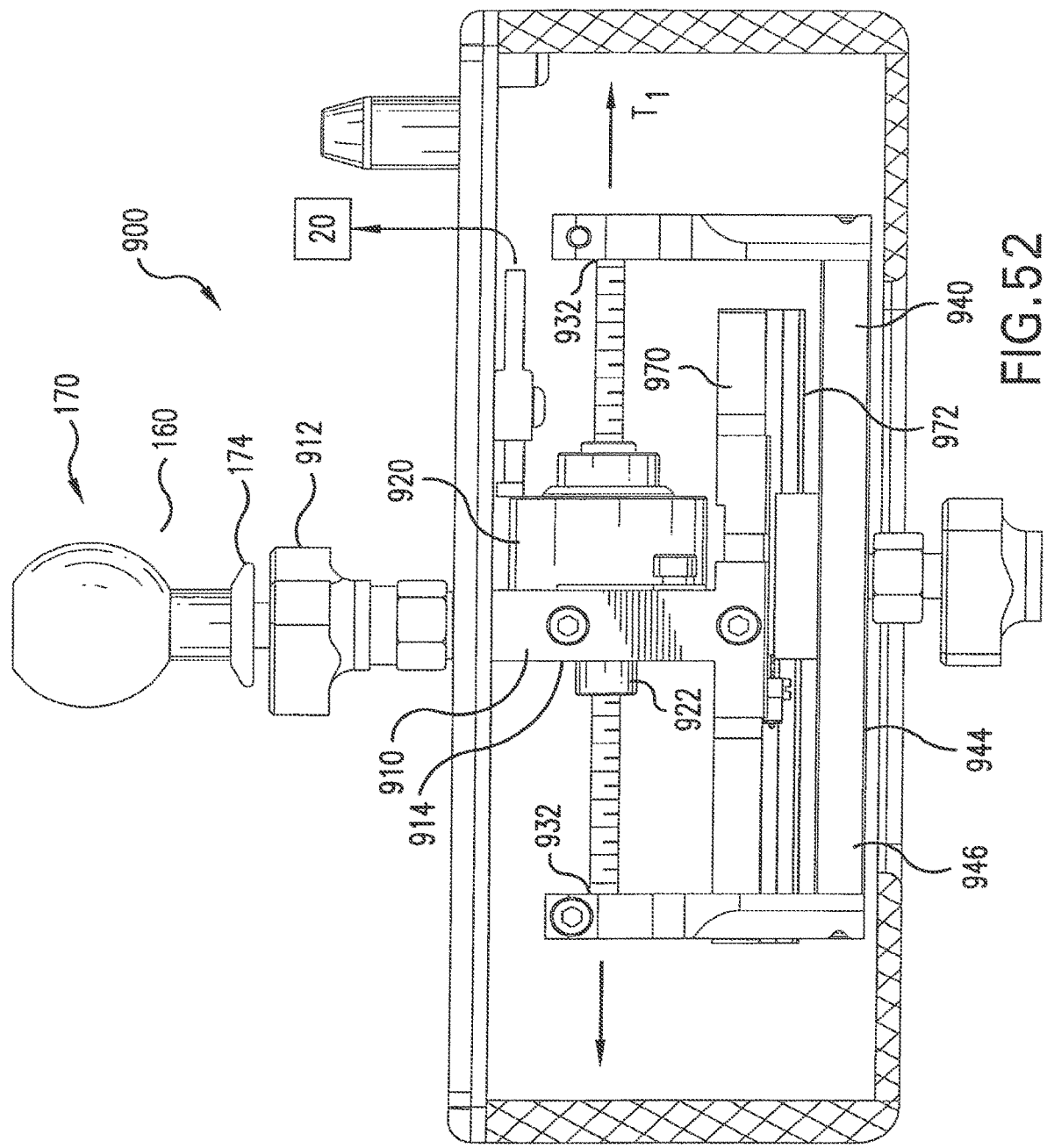
FIG. 52 is a partial cross-sectional view of the scanhead articulation unit.
Figure 53:
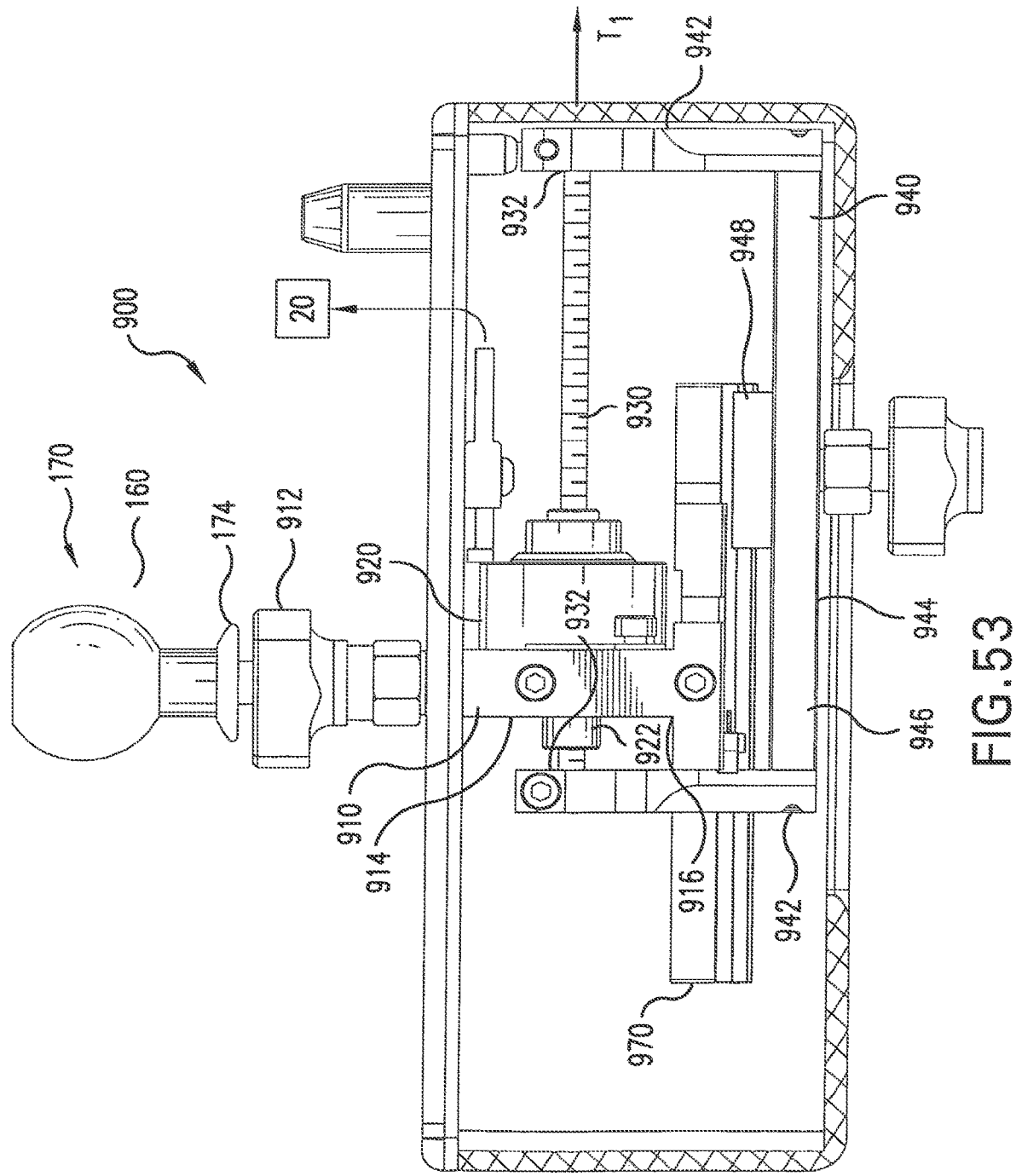
FIG. 53 is a partial cross-sectional view of the scanhead articulation unit.
Figure 54:
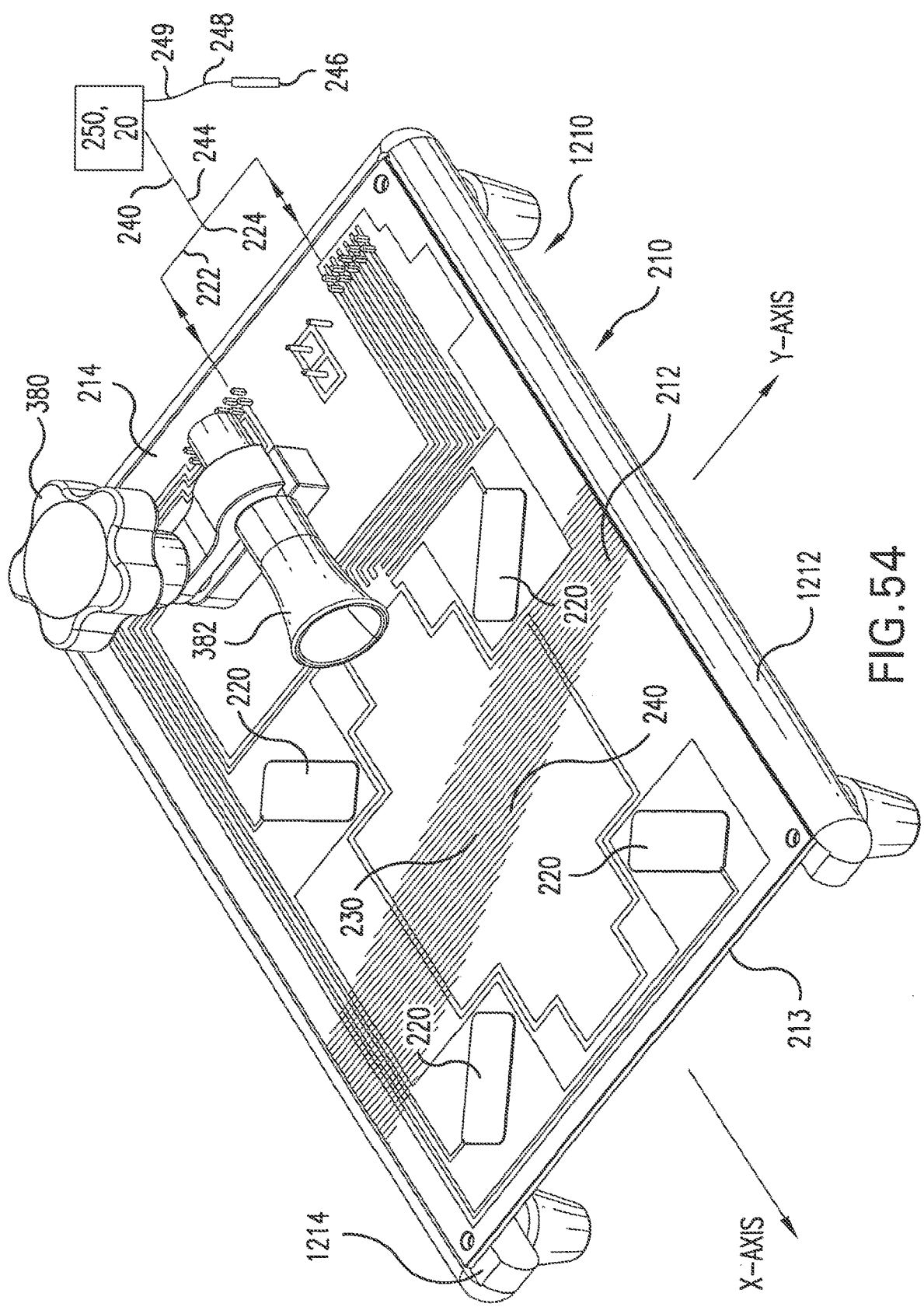
FIG. 54 is a top perspective view of a table member mounted onto a platform member.
Figure 55:
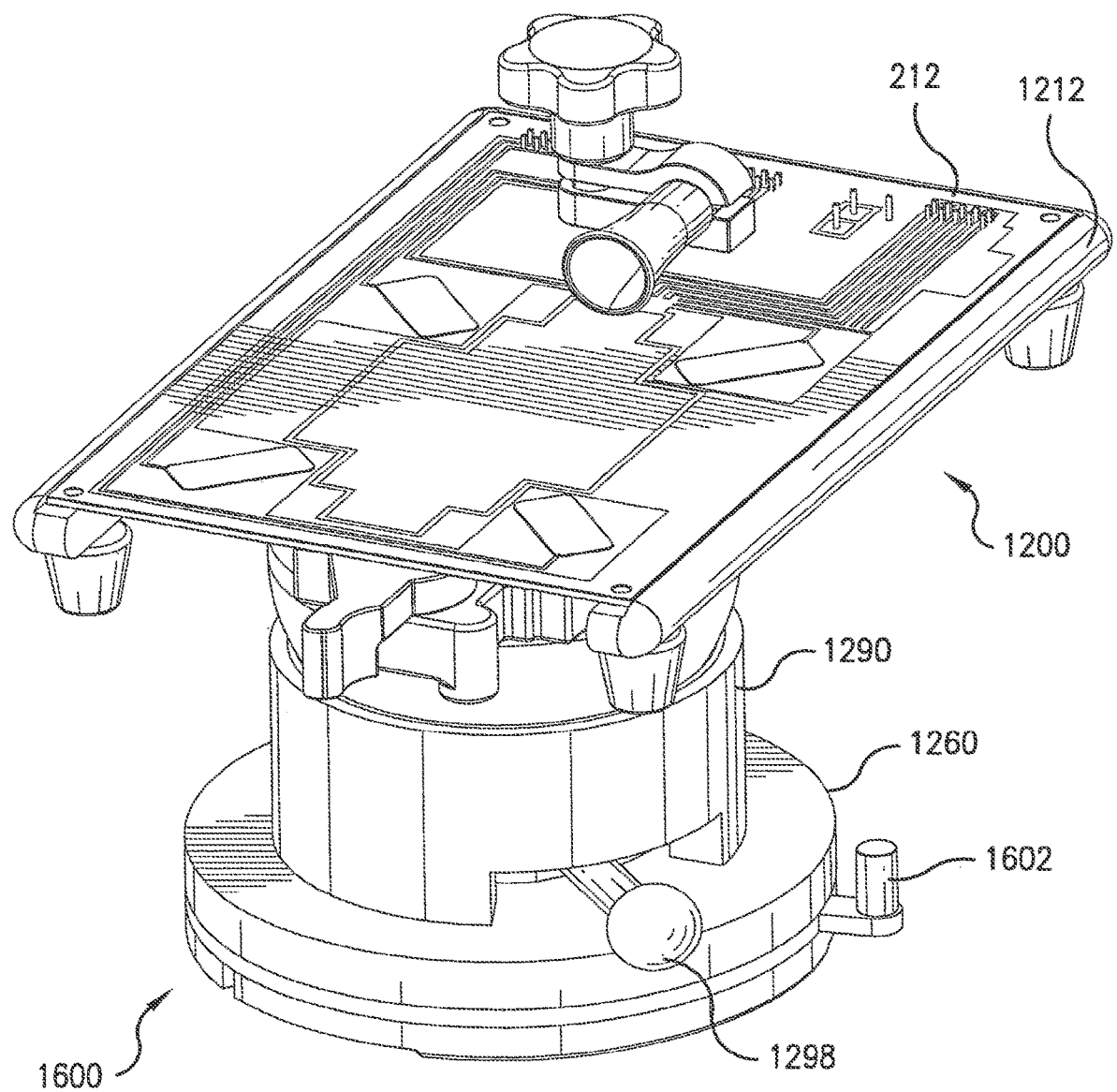
FIG. 55 is a perspective view of the platform member mounted thereon a ball-joint lock assembly that is, in turn, mounted onto a housing containing a magnetic lock.
Figure 56:
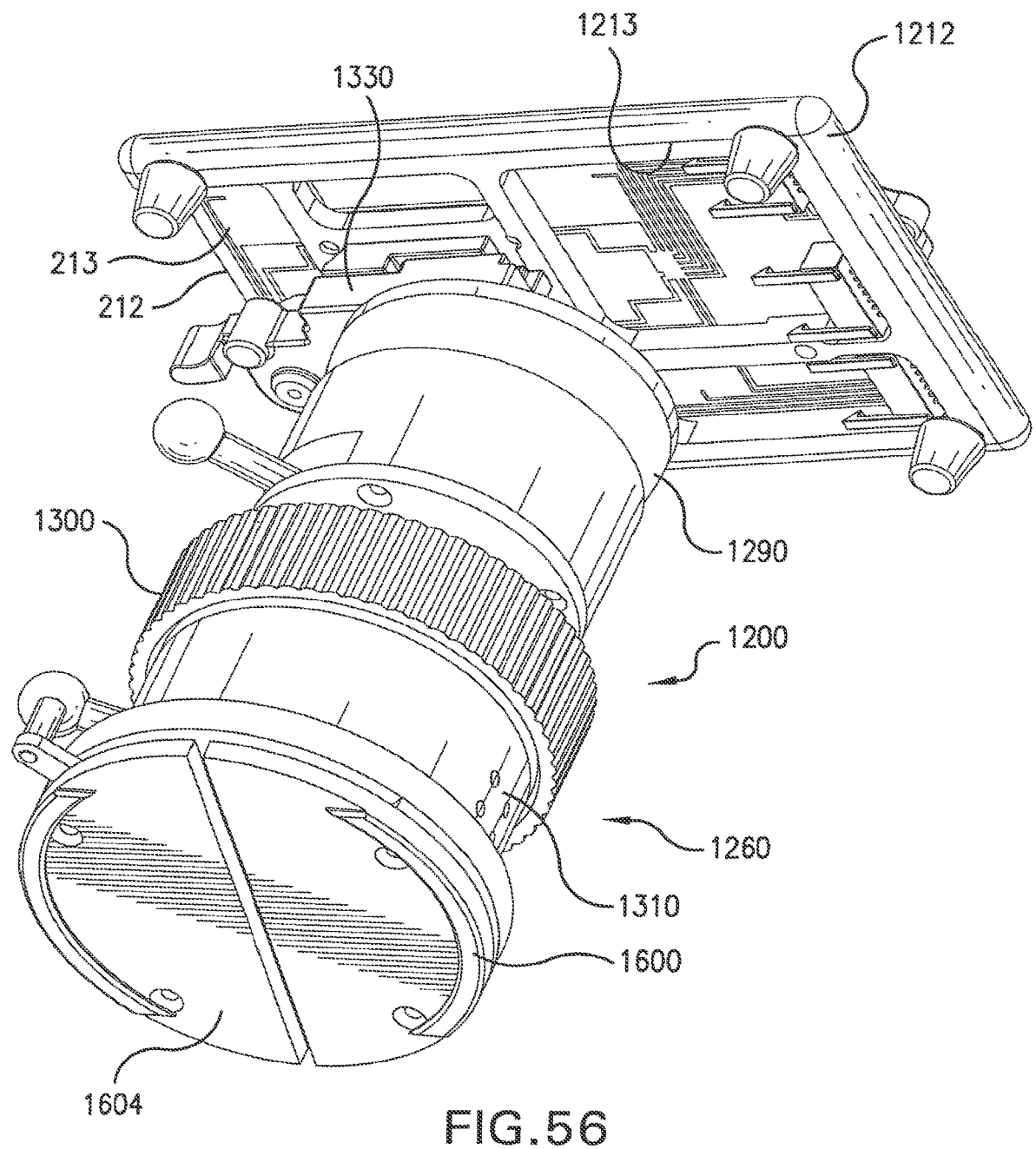
FIG. 56 is a semi-transparent layered bottom perspective view of the orientation control mechanism releasably mounted to the platform member of the present invention.
Figure 57:
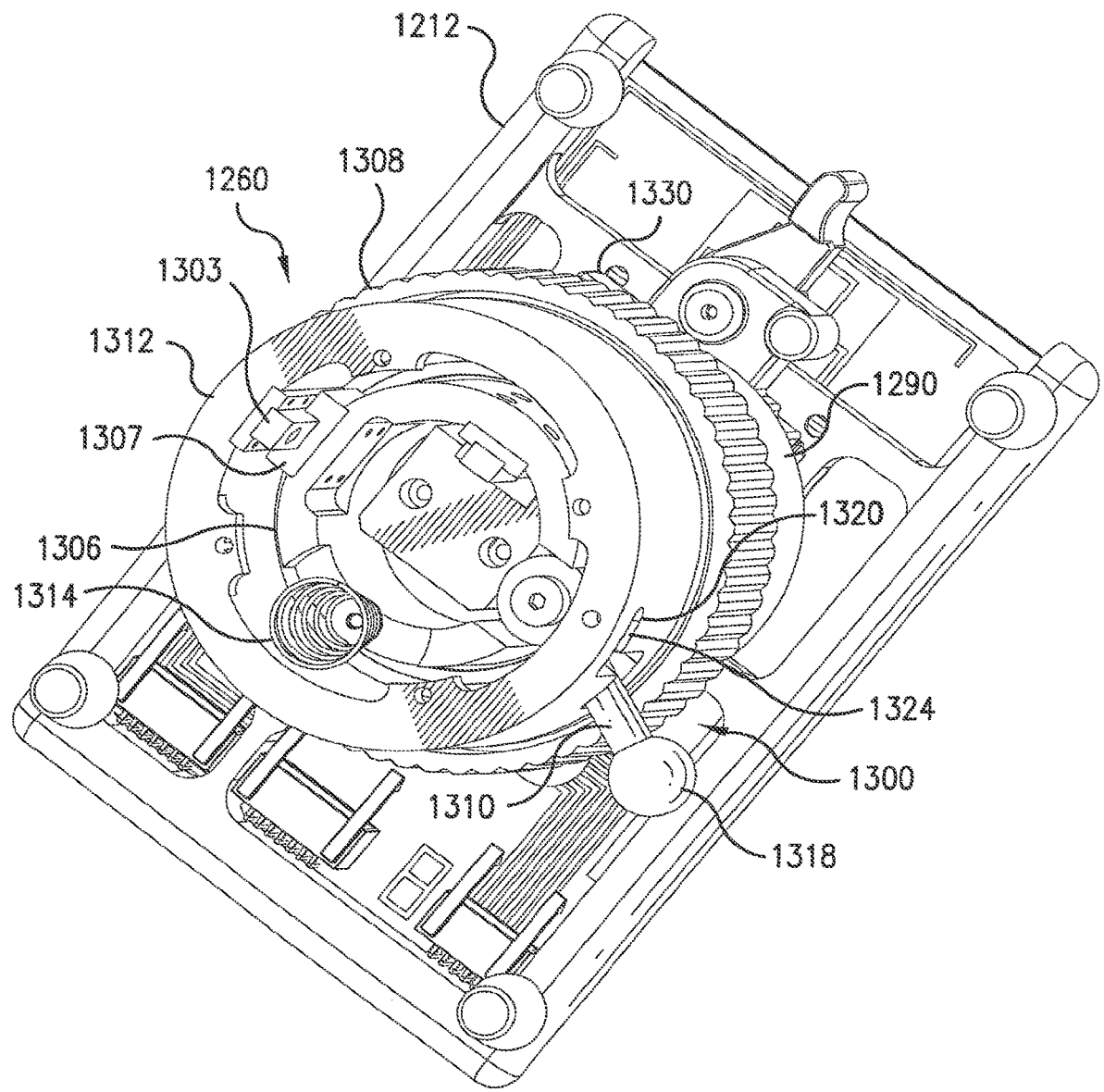
FIG. 57 is a partial bottom perspective view of the orientation control mechanism showing a bias element of the coarse height mechanism acting on the first housing that is partially housed within the second housing.
Figure 58:
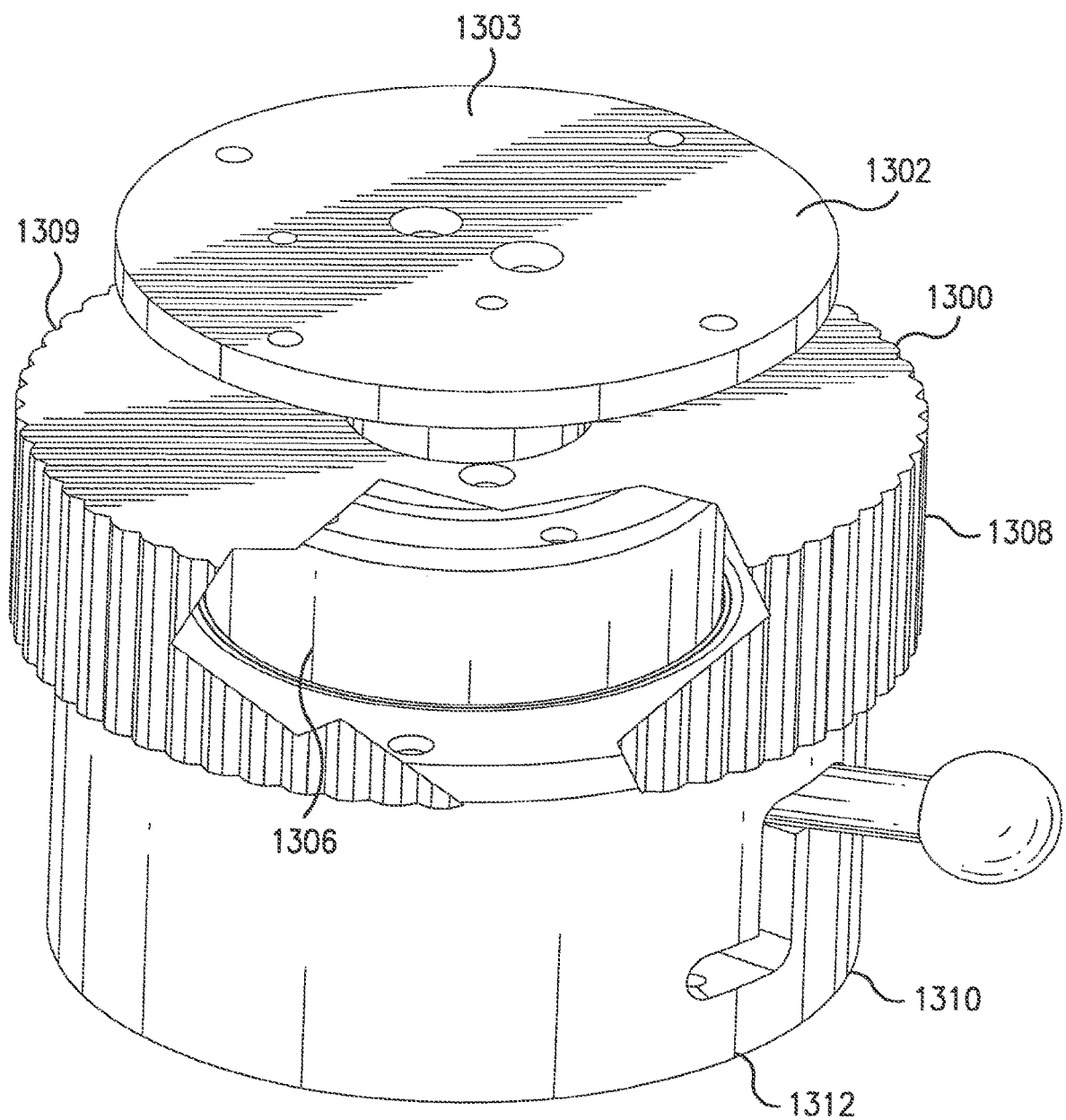
FIG. 58 is a partial semi-transparent top perspective view of the fine height mechanism of the orientation control mechanism.
Figure 59:
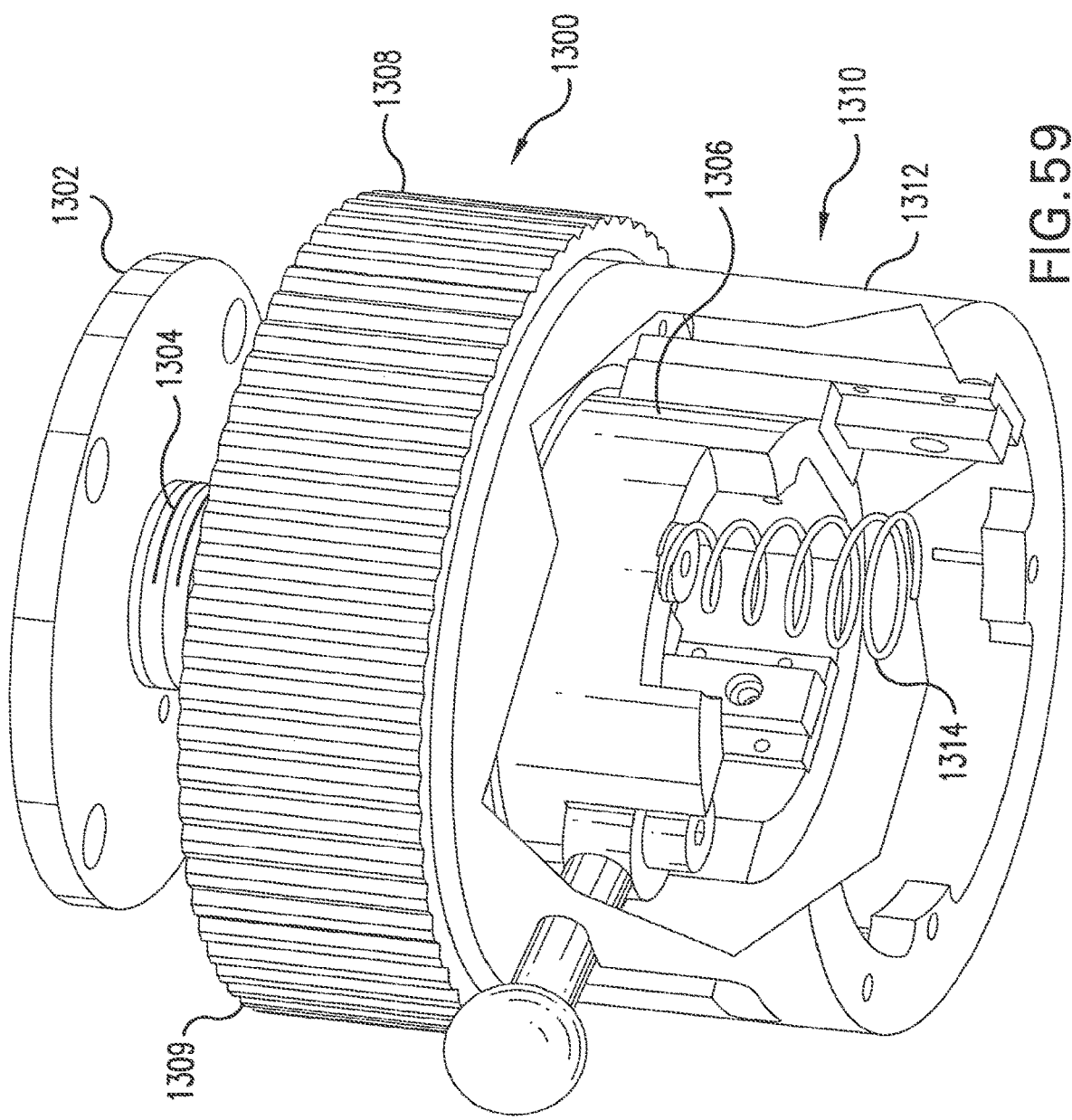
FIG. 59 is a partial semi-transparent perspective view of the fine and coarse height mechanisms of the orientation control mechanism.
Figure 60:
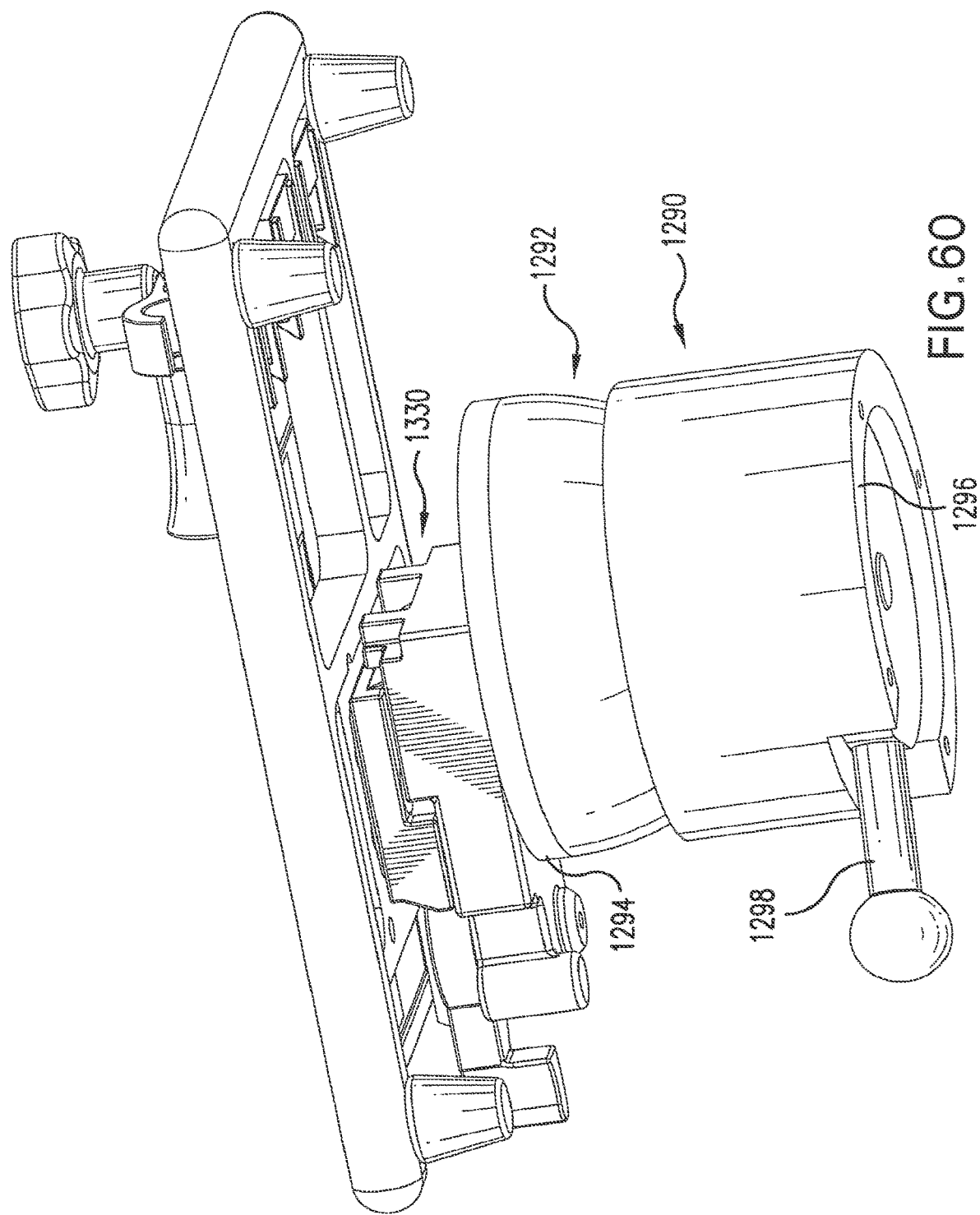
FIG. 60 is a partial semi-transparent perspective view of the ball-joint lock assembly of the orientation control mechanism mounted to a shoe member of a release mount assembly.

Referring to FIG. 1, one embodiment of an integrated multi-rail imaging system 10 of the present invention is shown. The imaging system includes a plurality of elongated rails 30, a scanhead assembly 100 selectively mounted onto a first rail 32 of the plurality of elongated rails, and a small-animal mount assembly 200 selectively mounted onto a second rail 34 of the plurality of elongated rails. In an alternative embodiment shown in FIGS. 2-4, the imaging system 10 can also include a needle injection assembly 400 that is selectively mounted onto a third rail 36 of the plurality of elongated rails.

As noted above, and as shown in the figures, the plurality of elongated rails 30 includes the first rail 32, the second rail 34, and, if the needle injection assembly 400 is used, the third rail 36. Each rail has a proximal end 35, a spaced distal end 37, and has a longitudinal axis R1, R2, and R3. Each rail 30 can be connected to an elongate support plate 40 by welding or by conventional fasteners, such as, for example, screws, bolts, or the like. Each support plate can have at least one damper member 42, such as, for example, rubber feet, connected to and extending from the bottom of the support plates to help reduce vibrations. The scanhead assembly 100, the small-animal mount assembly 200 and the needle injection assembly 400 each has a base member 102, 202, 402 that is constructed and arranged for movement in a reciprocal or otherwise gliding fashion upon their respective rails in a linear bi-directional manner, i.e., along the respective rail's longitudinal axis. As one will appreciate, each base member has at least one carriage 44 connected to the bottom of the base member that is adapted to slide on the respective rail. In one embodiment, each rail can also have a fixed stop 50 connected to the distal end of the rail to limit the movement of the base member mounted thereto. In an alternative embodiment, the second rail can have a pair of fixed stops 51 connected to the second rail and defining two fixed end points for bi-directional travel of the base member 202.

In use, an end edge 46 of the support plate 40 that is connected to the first rail 32 is connected to a side edge 48' of the support plate that is connected to the second rail 34. The proximal end 35 of the first rail 32 being positioned adjacent the second rail 34 and between the proximal and distal ends 35, 37 of the second rail. In this configuration, the longitudinal axis of the first rail is at an angle with respect to the longitudinal axis of the second rail. In one embodiment, the angle γ is about and between 150 to 30 degrees. In another embodiment, the angle γ is about and between 130 to 60 degrees. In yet another embodiment, the angle γ is about and between 110 to 70 degrees. In another embodiment, the angle γ is about and between 95 to 85 degrees.

If used, an end edge 46 of the base plate 40 that is connected the third rail 36 is connected to a side edge 48" of the base plate of the second rail 34 (opposite to the side edge to which the first rail 32 is connected). The proximal end 35 of the third rail 36 being positioned adjacent the second rail and between the proximal end and distal end of the second rail such that the third rail 36 opposes the first rail 32. In this example, the distal ends of the respective first and third rails extend away from each other and the longitudinal axis of the first and the third rails are substantially co-axial. Thus, the respective longitudinal axis R1, R2, and R3 are fixed in a relative orientation with respect to one another to provide a common coordinate system.

The imaging system 10 of the present invention can also include at least one movable stop 52. Each movable stop 52 is constructed and arranged for movement in a reciprocal or otherwise gliding fashion upon their respective rails in the linear bi-directional manner, i.e., along the respective rail's longitudinal axis. In one example, one movable stop 52 is mounted to each respective rail intermediate the respective base member 102, 202, 402 and the proximal end of the rail. In another example, one movable stop is mounted to each of the first and third rails.

Each movable stop 52 also has a stop clamping mechanism 54 that can selectively fix the position of the movable stop relative to the rail member. As one will appreciate, the operator of the system can readily adjust the position of the movable stops by releasing the stop clamping mechanism, moving the movable stop to the desired position, and clamping the movable stop to the rail at a desired position with the stop clamping mechanism. A portion of the base member 102, 202, 402 can be selectively and releasable secured to a portion of one respective movable stop.

In one example, the portion of the base member and the portion of the movable stop are magnetized with an attractive polarity such that, when brought into proximity to each other, the respective portions of the base member and the movable stop are attracted to each other. In another example, a second portion of each base member and a portion of the fixed stop are also magnetized with an attractive polarity such that, when brought into proximity to each other, the second portion of the base member and the portion of the fixed stop are attracted to each other. Thus, in use, the base members can be selectively moved between the fixed stop and the movable stop and can be releasably secured to the movable stop in the desired position. This allows one of the end points of travel of the base members to be selectively adjusted and allows the base members to be quickly moved away and brought back to the selected desired position, i.e., back to the selectable end point of travel.

In another embodiment, as shown in FIGS. 44-67, the imaging system 10 has a plurality of elongated rails 1030, comprising a first rail 1031 and a second rail 1032. In this embodiment, the second rail is selectively mountable to the first rail and is selectively movable in a linear bi-directional manner along the longitudinal axis RI of the first rail 1031. The longitudinal axis R2 of the second rail is positioned such that it is at an angle α relative to the longitudinal axis of the first rail. In fact, in one aspect, the longitudinal axis of the second rail is substantially perpendicular to the longitudinal axis of the first rail. The second rail 1032 may have a base member 1002 which enables the second rail to be selectively mounted to the first rail.

In one aspect of this embodiment, the scanhead assembly 1100 has a mount 1110 having a scanhead assembly base member 1102. The scanhead assembly base member is selectively mountable to the first rail 1031 and is selectively movable in a hi-directional manner along the longitudinal axis RI of the first rail.

Additionally, in one aspect, the imaging system comprises a small-animal mount assembly 1200. The small-animal mount assembly 1200 has a mount subassembly with a base member 1202 that is selectively mountable to the second rail. The mount subassembly base member 1202 is also selectively movable in a bi-directional manner along the longitudinal axis of the second rail, thereby positioning the small-animal mount assembly 1200 in a desired position along the second rail 1032.

As discussed in the previous embodiment, this embodiment of the imaging system 10 may also comprise a needle injection assembly 1400. In this aspect, the needle injection assembly has a base member 1402 that is selectively mountable to the first rail 1031 such that the second rail 1032 is positioned between the scanhead assembly 1100 and the injection assembly base member 1402. As with the scanhead assembly base member, the injection assembly base member is selectively movable in a bi-directional manner along the longitudinal axis RI of the first rail.

For ease of construction and manipulation, the rails 1030 of the imaging system can be of similar construction. In this aspect, the rails comprise a top surface 1036, a first edge 1037 and an opposed second edge 1038, where each edge is substantially parallel to the longitudinal axis of the rail, and a raised lip 1039. In one aspect, the raised lip 1039 extends therefrom each edge of the rail, substantially perpendicular to the top surface 1036 of the rail.

The respective base members of the scanhead unit, the needle injection unit, and the second rail may also comprise a plurality of bearing members 1042 mounted along their bottom portion. These bearing members may be positioned such that they engage each of the raised lips 1039 of the first rail, thereby enabling the respective base member to slide thereon the first rail along its longitudinal axis R1. As one in the art can appreciate, at least one hearing member 1042 should engage the raised lip of the first edge 1037 of the rail and at least one should engage the second edge 1038 of the rail. However, multiple bearing members may engage each of the raised lips. In this aspect, each of the respective base members may also have a locking mechanism 1050. One example of the locking mechanism 1050 comprises a threaded bore 1051 therethrough the base member. As one skilled in the art can appreciate, a complimentarily threaded knob 1053 may be inserted into the bore 1051, such that when the knob 1053 is rotated and the threaded portion of the knob is sufficiently inserted into the bore 1051, the distal end of the threaded knob frictionally engages the underlying first rail.

In yet another aspect, the first rail may be selectively mountable to a planar member 1040, which would substantially underlie at least a portion of the bottom of the first rail. The planar member 1040 may be equipped with at least one handle 1044, whereby, in use, an operator could transport the imaging system merely by lifting the handle(s) 1044. In this aspect, the imaging system becomes increasingly portable.

Scanhead Assembly

Referring to the figures, the scanhead assembly 100 includes a mount 110 and a scanhead unit 130. The mount 110 includes the base member 102, an elongate upright member 112, a cantilever beam 114, and a scanhead unit orientation control mechanism 160. The upright member 112 is connected to and extends substantially normal to the base member 102 (which is mounted as described above to the first rail). The cantilever beam 114 has a first end 116 and a spaced second end 118. The second end 118 of the beam has a sleeve member 120 constructed and arranged for movement in a reciprocal or otherwise gliding fashion upon the exterior surface 113 of the upright member 112 in a linear bi-directional manner, i.e., along a longitudinal axis of the upright member. The longitudinal axis of the beam 114 is co-planar to the longitudinal axis of the first rail 32.

The sleeve member 120 of the beam also has a beam lock mechanism 122 for selectively mounting the sleeve member at a desired position. For example, in use, a handle 124 of the beam lock mechanism can be rotated to loosen the beam lock mechanism, the beam can be raised or lowered into the desired position, and the handle 124 of the beam lock mechanism 122 is rotated to selectively lock the beam into the desired position relative to the upright member 122. In one example, the exterior surface 113 of the upright member 112 defines at least one longitudinally extending groove 115 and the interior surface 121 of the sleeve member 120 has at least one male protrusion 123. The male protrusion is sized and shaped for complementary receipt within one groove 115 of the upright member. In one example, the male protrusion 123 extends at least partially along the length of the interior surface 121 of the sleeve member.

In one example, the scanhead unit 130 is an ultrasonic scan head. As one will appreciate however, other scanhead units can be used, such as, for example, an MRI scanhead, a CT scanhead, and the like. The scanhead unit 130 is electrically coupled to an external computer 20 for processing of the images. The scanhead unit 130 is operatively connected to the beam 112 of the scanhead assembly 100 in selective orientation by the scanhead unit orientation control mechanism 160. In one example, the scanhead unit orientation control mechanism comprises an angle control lock mechanism 162 and a ball joint lock mechanism 170. A proximal end 164 of the angle control lock mechanism 162 is connected to the beam proximate the first end 116 of the beam. A fixed portion of the angle control lock mechanism extends downwardly away from the beam along a substantially vertical axis. A distal end 166 of the angle control lock mechanism is connected to a proximal end 172 of the ball joint lock mechanism 170 and is constructed and arranged for pivotal movement of the ball joint lock mechanism along an angle control lock plane defined by the co-planar longitudinal axis of the first rail and the beam. As one will appreciate, the angle control lock mechanism 160 can be moved between a locked position and an unlocked position.

A distal end 174 of the ball joint lock mechanism 170 is connected to the scanhead unit and is constructed and arranged for pivotal movement of the scanhead unit. As one will appreciate, the ball joint lock mechanism 170 allows the operative end 132 of the scanhead unit to be positioned at an angle with respect to the vertical axis of the angle control lock mechanism and with respect to the angle control lock plane. The ball joint lock mechanism 170 is movable between a locked position and an unlocked position. When the ball joint lock mechanism 170 is locked at the desired angle, it will be appreciated that the operative end 132 of the scanhead unit 130 can be moved through an arc in a desired image plane by selectively unlocking the angle control lock mechanism 160 and moving the angle control lock mechanism along its fixed range of movement.

In another embodiment, as depicted in FIGS. 44-53 of the imaging system of the present invention, wherein the second rail 1032 is mounted thereon the first rail 1031 and all of the rails are of similar construction, the mount 1110 of the scanhead assembly 1100 has a base member 1102 that is selectively mountable onto the first rail 1031. As discussed herein above, the base member 1102 may have a plurality of bearing members 1042 that slidably engage the raised lips of the first rail 1031.

In this embodiment, the scanhead assembly comprises a third rail 1033 and a fourth rail 1034. The third rail extends upwardly away from the scanhead assembly base member 1102, while the fourth rail 1034 is selectively mounted thereon the third rail 1033 and is substantially perpendicular to it. The scanhead unit orientation control mechanism 160 is connected to a first end 1041 of the fourth rail.

In this aspect, a cantilever mount member 810 is mounted thereon the third rail such that it can move in a bi-directional manner along the longitudinal axis of the third rail. The fourth rail 1034 is slidably attached to the cantilever mount member 810 such that the fourth rail can move in a linear, bi-directional manner along its longitudinal axis R4 with respect to the cantilever mount member and, thus, with respect to the longitudinal axis of the third rail 1033.

In one aspect, the scanhead assembly 1100 has a height adjustment mechanism 830 that comprises an upright column 840, a gear housing 850, a threaded rod member 860, and the cantilever mount member 810. The upright column 840 is mounted thereon the scanhead assembly base member 1102 such that it extends upwardly away from the base member and has an upright axis C1. It acts to raise the entire third rail 1033 a fixed distance from the scanhead assembly base member. The gear housing 850 is mounted thereon a distal end 842 of the upright column and one end of the third rail is mounted to the top of the gear housing such that it extends upwardly parallel to the upright axis The third rail also comprises an end member 812 mounted at the distal end 814 of the third rail. The end member defines a cavity 815 for operative receipt of a bearing. The proximal end 862 of the threaded rod member is rotatably mounted to the gear housing and the distal end 864 of the threaded rod member 860 is rotatably mounted in the hearing in the end member such that the threaded rod is positioned substantially parallel to the longitudinal axis R3 of the third rail. As is depicted in the figures, the proximal end of the rod member is housed within the gear housing and has a beveled gear 852 mounted thereto. A crank member 854 is provided having an end disposed therein the gear housing that has a complimentary beveled gear 856 mounted thereon. In use, rotation of the crank member 854 results in rotation of the threaded rod member 860 about its axis. As one will appreciate, the gear housing 850 may be mounted thereon the top of the scanhead assembly base member 1102, omitting the upright column.

The cantilever mount member 810 is mounted to the third rail and defines a threaded bore 813 that is sized and shaped for complimentary engagement with the threaded surface of the rod member 860. In use, when the crank member is rotated and the threaded rod member rotates, the cantilever mount member selectively moves in a bi-directional manner along the third rail. As may be seen in the figures, the cantilever mount member 810 may also comprise a plurality of bearing members 1042 disposed thereon the cantilever mount member which may slidably engage a portion of the raised lips 1039 extending from the edges of the third rail. To selectively secure the cantilever mount member, and thus the fourth rail, in position along the third rail, a rail lock assembly 816 is provided. In this aspect, a body member 818 is mounted to portions of the back face 811 of the cantilever mount member such that a portion of the body member overlies the back face 1043 of the third rail. The portion of the body member defines a threaded bore 820 sized and shaped for complementary receipt of a threaded knob 822. In use, the cantilever mount member 810 is raised/lowered to the desired position and the knob is rotated such that the distal end 824 of the knob engages the back face 1043 of the third rail to frictionally lock the cantilever mount member into position relative to the third rail. Additionally, as mentioned herein above, the fourth rail 1034 is slidably mounted thereon the cantilever mount member. As can be seen in the figures, the cantilever mount member comprises a second set of bearing members 1042 disposed thereon the cantilever mount member which may slidably engage a portion of the raised lips extending from the edges of the fourth rail, the fourth rail being substantially perpendicular to the third rail. To selectively secure the fourth rail in position with respect to the cantilever mount member, and thus the third rail, another rail lock assembly 815 is provided. In this aspect, a body member 817 is mounted to portions of the top surface of the cantilever mount member, opposite the other body member 818, such that a portion of the body member 817 overlies the top surface 1036 of the fourth rail. Similarly, a portion of the body member defines a threaded bore 820' sized and shaped for complementary receipt of a threaded knob 822'. In use, the third rail is moved to the desired position and the knob 822' is rotated such that the distal end of the knob engages the top surface 1036 of the fourth rail to frictionally lock the fourth rail into position relative to the cantilever member.

The scanhead unit orientation control mechanism 160 is connected to a portion of the first end 1041 of the fourth rail and a portion of the scanhead unit 1130. As described herein above, the scanhead unit orientation control mechanism 160 is constructed and arranged to position the emitting end of the scanhead unit 130 in a desired image plane. In use, the scanhead unit 130 has transducer that travels within the scanhead in order to enable the scanhead unit to take an image slice in the image plane.

In one aspect, the scanhead assembly 1100 further comprises a scanhead articulation unit 900 selectively mounted therebetween the scanhead unit orientation control mechanism 160 and the scanhead unit 1130. The scanhead articulation unit 900 is designed to articulate the scanhead unit 130 in a direction normal to the desired image plane, thereby enabling the scanhead unit to take multiple image slices in multiple image planes. When the multiple images are electronically combined, the resulting image has an apparent three-dimensional quality.

The scanhead articulation unit 900 comprises a motor mount 910, a motor assembly 920, a threaded rod 930, and a saddle member 940. The motor mount has a proximal end 912 that is mounted to the distal end 174 of the ball joint lock mechanism 170 of the scanhead unit orientation control mechanism 160. A portion of the motor mount defines a bore 914. Additionally, the motor assembly 920 is mounted thereon a portion of the motor mount. In one aspect, the motor assembly has a driven tube 922 which is co-axial with the bore 914 of the motor mount and has a threaded interior surface. As one can appreciate, the motor assembly can be a stepper motor or any other conventional motor, wherein the driven tube is the shaft of the motor. The threaded rod 930 is constructed and arranged to operatively engage the inner surface of the driven tube such that its longitudinal axis T1 is substantially transverse to the desired image plane. In use, when the driven tube is rotated by the motor assembly, the threaded rod is driven in a bi-directional manner along its longitudinal axis.

The saddle member 940, which has two opposed sides 942 and a floor 944 extending therebetween, is mounted thereon the threaded rod such that the ends 932 of the threaded rod rotatably engage the two opposed sides 942 of the saddle member. As one can appreciate, the sides of the saddle member may comprise conventional bearings for receipt of the ends of the threaded rod. The scanhead unit is mounted to and extending therefrom the bottom portion 946 of the floor 944 of the saddle such that movement of the threaded rod moves the saddle member that, in turn, moves the scanhead unit 130 about an axis that is parallel to the longitudinal axis T1 of the threaded rod. Thus, movement of the threaded rod along its axis moves the image plane along a movement axis M1 substantially parallel to the longitudinal axis of the threaded rod.

In one aspect, the distal end 174 of the ball joint lock mechanism 170 defines a quick release post (not shown) that comprises a longitudinal slot (not shown). In this aspect, the proximal end of the motor mount comprises a female quick release mount. The quick release mount comprises a pin disposed on its interior portion sized and shaped for complimentary engagement with the longitudinal slot of the quick release post. In other words, the two components form a key-way relationship. This relationship ensures that the scanhead articulation unit 900 is mounted in a position such that the movement of the scanhead unit 130 is substantially normal to the desired image plane. In this aspect, the bottom portion 946 of the floor 944 of the saddle is similarly equipped with a quick release mount, while the scanhead unit 130 is equipped with a quick release post.

In another aspect, the motor mount 910 further comprises an elongate beam member 970 attached to the distal end 916 of the motor mount. As depicted in the figures, the beam member 970 is positioned substantially transverse to the longitudinal axis of the motor mount and substantially parallel to the longitudinal axis T1 of the threaded rod. The beam member 970 comprises a bearing surface 972 along its longitudinal axis. In one aspect, the saddle member 940 comprises a bearing member 948 attached to and extending therefrom atop portion 947 of the floor 944 of the saddle member. The bearing member 948 would operatively engages the bearing surface 972 of the beam member 970, such that, in this aspect, the beam member and the bearing system acts to stabilize the movement of the scanhead unit 130 along the movement axis M1.

Small-Animal Mount Assembly

The small-animal mount assembly 200 of the present invention comprises a table subassembly 210 and a mount subassembly 260. The table subassembly 210 comprises a table member 212. The mount subassembly 260 comprises a base member 202, which is mounted to the second rail 34 as described above, a planer platform 262, and a table orientation control mechanism 280 selectively positioned onto a portion of an upper surface 264 of the platform 262. The table orientation control mechanism 280 is constructed and arranged for adjusting the height, tilt and rotation of the operatively connected table member 212 relative to the upper surface 264 of the platform 262.

In one example, an operator selectable plunger lock mechanism 206 is connected to the edge of the base member 202. A portion of the plunger lock mechanism is constructed and arranged for selectively engaging a portion of a fixed stop 51 connected to the second rail. The plunger lock mechanism can comprise a spring mechanism for "locking" the plunger lock mechanism to the respective fixed stop until operator force is applied to the plunger lock mechanism 206. In use, the operator draws the plunger lock mechanism upward to separate the plunger lock mechanism from the respective fixed stop. The base member 202 can then be moved along the longitudinal axis of the second rail until it is selectively lock to the other fixed stop. In this example, one fixed stop Si is positioned proximate the distal end of the second rail and the other fixed stop 51 is positioned intermediate the proximal and distal ends of the second rail.

In one example, the platform 262 is movably connected to the base member 202 by a platform adjustment mechanism 270. The platform 262 has a lower surface 266 that is opposed to the upper surface and defines a first axis A1 parallel to the longitudinal axis of the second rail and a second axis A2 normal to first axis. The platform can also have a raised edge 268 extending substantially about the periphery of the platform to help prevent the orientation control mechanism from falling from the upper surface 264 of the platform.

The platform adjustment mechanism 270 is constructed and arranged for moving the platform in a platform plane defined by the respective first-axis and second-axis of the platform. A platform base 272 of the platform adjustment mechanism is connected to a portion of the top surface 204 of the base member and an adjustable armature 274 of the platform adjustment mechanism is connected to a portion of an edge of the platform 262. In use, rotational movement of a first control knob 276 of the platform adjustment mechanism moves the platform bi-directionally relative to the base member along the first axis of the platform. In the same manner, rotational movement of a second control knob 278 of the platform adjustment mechanism moves the platform bi-directionally relative to the base member along the second axis of the platform. As one will appreciate movement of the platform 262 relative to the base member forward or rearward along the respective first or second axis depends upon the direction the first or second control knob is moved. In one aspect, the platform can be moved relative to the base member 202 between end points along each of its respective first and second axis less than and including about 100 mm. In another aspect, less than and including about 80 mm. In yet another aspect, less than and including about 60 mm. In another aspect, less than and including about 50 mm.

In this example, the lower surface 266 of the platform can rest on the top surface 204 of the base member 202. Further, the upper and lower surfaces 264, 266 of the platform and the top surface 204 of the base member are positioned in parallel planes. A coating or sheet of low-friction material such as, for example, Teflon™, can cover the lower surface 266 of the platform or the top surface 204 of the base member 202. One skilled in the art will appreciate that other low-friction materials are contemplated. Thus, in use, the platform can be selectively moved in the first and second axis within the platform plane under the control of the platform adjustment mechanism 270. The low-friction coating allows this motion to take place with minimal friction.

The orientation control mechanism 280 comprises a housing 282 having a top 284 and a bottom 286. In use, the bottom of the housing is disposed onto and can be selectively slid along the upper surface 264 of the platform 262. The upper surface of the platform can also be coated with low-friction material. This low-friction coating allows the operator to readily position the housing 282 of the orientation control mechanism onto a desired portion of the upper surface of the platform. The orientation control mechanism comprises a magnetic lock 600 that is housed within the housing. Upon movement of a magnet control knob 602, which extends beyond the exterior of the housing, the magnetic lock 600 is movable from a retracted, non-engaged position, to an engaged position in which a magnet 604 is brought into attractive contact with the upper surface of the platform. As one will appreciate, when the magnetic lock is in the engaged position, the housing of the orientation control mechanism is fixed relative to the platform due to the attraction of the magnet and the platform. However, even if the magnetic lock 600 is in the engaged position, the housing can slide on the upper surface of the platform if sufficient force is exerted onto the housing or the connected table assembly.

The orientation control mechanism 280 can further comprise a coarse height mechanism 290, a rotation control mechanism 310, a fine height control mechanism 320, a first tilt control mechanism 330, and a second tilt control mechanism 340. The coarse height mechanism is housed within the housing and is constructed and arranged for selective bi-directional movement of an upright shaft member 300 along an upright axis of the orientation control mechanism 280. The upright axis is substantially normal to the longitudinal axis of the second rail 34. Thus, upon movement of a lever control 290 of the coarse height mechanism, the shaft member 300 can be raised or lowered as desired between a top, extended, position and a lowered, contracted, position. To accommodate the movement of the lever control, the housing defines an "L" shaped slot 294 in one side having an upright portion 296 and a longitudinally extending portion 298 proximate the top of the housing. In the lowered position, the lever control is in lower portion of the upright portion of the slot. In order to raise the top 301 of the shaft member 300 to its top position, the lever control 292 is lifted upward the extent of the upright portion of the slot 294 and is then slid into and seated within the longitudinally extending portion of the slot.

The shaft member 300 of the orientation control mechanism can be rotated about the upright axis about a bearing 312 positioned within the housing 282. The rotation brake mechanism 310 is housed within the housing and is constructed and arranged for selectively engaging a brake surface 314 connected to the shaft member so that the shaft member can be fixed in a desired position about the upright axis. Thus, the shaft member can be rotated by applying a rotational force to the shaft such that the table member, which is operatively engaged to the shaft member, can be rotated about the upright axis until the table member is in the desired orientation. When the shaft member is positioned in the desired position, a brake knob 314, which extends beyond the exterior of the housing, of the rotation brake mechanism 310 can be selectively activated to selectively fix the shaft member in the desired position relative to the upright axis.

A movable cap 322 is operatively connected to the shaft member and can be selectively moved by the fine height control mechanism 320. The fine height control mechanism is constructed and arranged for selective bi-directional movement of the movable cap relative to the top 301 of the shaft member 300 along the upright axis of the orientation control mechanism 280. Thus, upon movement of a height control knob 324 of the fine height mechanism, the cap 322 can be raised or lowered as desired. In one aspect, the cap 322 can be moved relative to the top 301 of the shaft member between end points along the upright axis less than and including about 50 mm. In another aspect, less than and including about 30 mm In yet another aspect, less than and including about 20 mm. In another aspect, less than and including about 10 mm.

The table member 212 defines a table plane that further defines an x-axis and an y-axis. One will appreciate that the x and y-axis of the table plane form a common coordinate system. The first tilt control mechanism 330 is operatively connected to the cap 322 and is constructed and arranged for selectively adjusting and securing the tilt of the table member 212 relative to the y-axis of the table plane. The second tilt control mechanism 340 is operatively connected to a bottom surface 213 of the table member 212 and is constructed and arranged for selectively adjusting and securing the tilt of the table member relative to the x-axis of the table plane. A portion of the second tilt control mechanism 340 is mounted onto a top surface 332 of the first tilt control mechanism 330.

In this configuration, the first and the second tilt control mechanisms 330, 340 allow the table member 212 to be angled with respect to the respective y-axis and x-axis of the table plane. In one aspect, the angle is less than and including about 60 degrees (i.e., +/−30 degrees). In another aspect, the angle is less than and including about 45 degrees i.e., +/−22.5 degrees). In yet another aspect, the angle is less than and including about 30 degrees (i.e., +/−15 degrees). Thus, in operation, selective manipulation of the controls of the mount subassembly 260 by the operator allows the table member 212 to be oriented in a desired table surface plane.

The table member 212 has a top surface 214 that is disposed in the table surface plane. The table subassembly 210 can also comprise a plurality of ECG electrode contact pads 220, at least one grid of electronic heating elements 230, and/or at least one thermocouple 240. In one aspect, the plurality of ECG contact pads is operatively attached to the top surface 214 of the table member. Each ECG contact pad senses an ECG signal within a portion of a small animal that is secured against the ECG contact pad. Each ECG contact pad 220 is spaced from an adjacent contact pad and can be positioned so that each one of the feet/paws of the small animal can be selectively positioned against one of the ECG contact pads. In one aspect, the plurality of ECG contact pads comprises four ECG contact pads that are positioned in a spaced "X" configuration so that the respective feet of the small animal can be positioned in a splayed position. Each ECG contact pad 220 generates an ECG signal 222 representative of the sensed ECG. The ECG signal can be transmitted through an A/D converter (not shown) to a control apparatus 250 on ECG signal line 224. This ECG signal can be transmitted through an isolated ECG amplifier and digital or analog anti-aliasing filter (not shown) to remove noise and amplify the signal before processing.

The grid of electronic heating elements 230 is disposed onto the top surface 214 of the table member 212 and is electrically coupled to the control apparatus 250. The temperature of the top surface 214 of the table member can be adjusted via the control apparatus so that a small animal's temperature can be maintained within a desired range when the small animal is positioned onto the top surface 214 of the table member. If used, the thermocouple 240 is connected to the top surface of the table member and can be positioned such that a portion of the small animal overlies the thermocouple when the small animal is secured to the top surface 214. In one example, the thermocouple is positioned near the center of the top surface 214 of the table member 212 and is spaced from the at least one grid of electronic heating elements 230. The thermocouple 240 generates a temperature signal 242 representative of the sensed temperature of the small animal proximate the thermocouple. The temperature signal 242 can be transmitted through an AID converter (not shown) to the control apparatus 250 on temperature signal line 244. This temperature signal can be transmitted through an isolated amplifier and digital or analog anti-aliasing filter (not shown) to remove noise and amplify the signal before processing.

The table subassembly 210 can also comprise a rectal temperature probe 246. The rectal temperature probe generates an internal temperature signal 248 representative of the sensed internal temperature of the small animal with the rectum of the small animal the thermocouple. The internal temperature signal 248 can be transmitted through an A/D converter (not shown) to the control apparatus on temperature signal line 249. This internal temperature signal can be transmitted through an isolated amplifier and digital or analog anti-aliasing filter (not shown) to remove noise and amplify the signal before processing.

In one example, if external embryonic imaging is desired, the table subassembly 210 can further comprise a walled dish 360 and a dish support mechanism 370. The dish 360 has a peripheral wall 362 and defines an opening 364 in the bottom of the dish. The dish is formed of a substantially rigid material, such as, for example, a rigid plastic. A pliable membrane 366 defining a slit 368 is connected to the opening to form a moisture proof connection. In one aspect, in a relaxed position, the slit in the membrane is closed and is moisture proof. In a stretched position, the slit in the membrane is open. The pliable membrane can be a rubber membrane. In another aspect, the slit 368 in the membrane 366 is open in both the relaxed and stretched positions.

The dish 360 can be selectively held in position relative to the top surface 214 of the table member 212 by selective actuation of a dish support mechanism 370. The dish support mechanism has an arm member 372 and a fastener 374. The arm member has an upper portion 376 that is constructed and arranged for selectively clamping onto a portion of the wall 262 of the dish. As one will appreciate, the dish 260 can be removed by removing knurled screw 378. The arm member 372 has a lower portion defining an elongate slot 379. The fastener 374 passes through the slot 379 and can selectively secure the lower portion of the arm member to an edge of the table member. In use, the position of an attached dish can be adjusted by loosening the fastener 374, adjusting the dish 360 into the desired position, and tightening the fastener 374 to secure the dish 260 in the desired position.

In certain externalized procedures, the small animal is secured to the top surface 214 of the table member and the dish 260 is disposed onto the small animal such that the pliable membrane 366 is in the stretched open position with the "open" slit forming a moisture proof seal between the small animal and the dish. In this aspect, embryos can be passed through the slit in the rubber membranes and can be imaged in the dish while still attached to the small animal.

The table subassembly 210 can also comprise a clamp member 380 secured to a portion of the top surface 214 of the table member. In one aspect, the clamp member 380 is constructed and arranged for grasping a portion of a conical small animal mask 382 that is shaped and sized for fit with the snout of the small animal. The mask 382 is connected to at least one anaesthetic line that is coupled to an external anaesthetic source, not shown. In an alternative aspect, the clamp member 380 can selectively grasp a portion of the at least one anaesthetic line.

Referring now to FIGS. 54-63, an alternative embodiment of the small-animal mount assembly 1200 of the present invention is illustrated. In this aspect, the small-animal mount assembly 1200 of the present invention includes a table subassembly 1210 and a mount subassembly 1240. The table subassembly 1210 comprises a table member 212 and a platform member 1212. In one aspect, the table member has a bottom surface 213 and defines a table plane and the platform member 1212 has a top face 1214 and an opposed bottom face 1213. The bottom surface 213 of the table member 212 is mounted thereon the top face 1214 of the platform member 1212.

The mount subassembly 1240 comprises a mount assembly base member 1202, which is mounted to the second rail 1032 as described above, a planar platform 1242, and a table orientation control mechanism 1260 selectively positioned onto a portion of an upper surface 1244 of the platform 1242. The table orientation control mechanism 1260 is constructed and arranged for adjusting the height, tilt and rotation of the operatively connected table member 212 relative to the upper surface 1244 of the platform 1242. The small-animal mount assembly can also comprise a release mount assembly 1330 that is constructed and arranged for releaseably mounting the platform member 1212 to the orientation control mechanism 1260.

In one aspect, an operator selectable plunger lock mechanism 1206 is mounted on the top surface of the mount assembly base member 1202. A distal portion of a plunger of the plunger lock mechanism is constructed and arranged for selectively engaging a portion of one position hole of the at least one position hole defined in the second rail. The plunger lock mechanism 1206 can include a spring mechanism for "locking" the plunger lock mechanism to the respective position hole until operator force is applied to the plunger lock mechanism 1206. In use, the operator draws the plunger of the plunger lock mechanism upward to separate the plunger from the respective position hole. While holding the plunger "up," the mount assembly base member 1202 can be moved along the longitudinal axis of the second rail until the plunger is close to the desired position. The plunger is then released and the mount assembly base member is moved fractionally until the distal end of the plunger seats into the selected position hole of the second rail. Further, the second rail can include a first end cap positioned at the distal end of the second rail and a second end cap positioned at the proximal end of the second rail. The end caps prevent the base member from sliding off of the ends of the second rail. Of course, in is contemplated that the end caps can be selectively removable on that the mount assembly base member 1202 can be selectively separated from the second rail as desired.

Similar to the aspect described above, the platform 1242 is movably connected to the mount assembly base member 1202 by a platform adjustment mechanism 1250. The platform 1242 has a lower surface 1246 that is opposed to the upper surface and defines a first axis A1 parallel to the longitudinal axis of the second rail and a second axis A2 normal to first axis. The platform can also have a raised edge 1248 extending substantially about the periphery of the platform to help prevent the orientation control mechanism from falling from the upper surface 1244 of the platform.

The platform adjustment mechanism 1250 is constructed and arranged for moving the platform in a platform plane defined by the respective first axis and second-axis of the platform. A platform base 1252 of the platform adjustment mechanism is connected to a portion of the top surface 1204 of the mount assembly base member and an adjustable armature 1254 of the platform adjustment mechanism is connected to a portion of an edge of the platform 1242. In use, rotational movement of a first control knob 1256 of the platform adjustment mechanism moves the platform hi-directionally relative to the mount assembly base member along the first axis of the platform. In the same manner, rotational movement of a second control knob 1258 of the platform adjustment mechanism moves the platform bi-directionally relative to the mount assembly base member along the second axis of the platform. As one will appreciate movement of the platform 1242 relative to the mount assembly base member forward or rearward along the respective first or second axis depends upon the direction the first or second control knob is moved. In one aspect, the platform can be moved relative to the mount assembly base member 1202 between end points along each of its respective first and second axis less than and including about 100 mm. In another aspect, less than and including about 80 mm. In yet another aspect, less than and including about 60 mm. In another aspect, less than and including about 50 mm.

In this aspect, the lower surface 1246 of the platform can rest on the top surface 1204 of the mount assembly base member 1202. Further, the upper and lower surfaces 1244, 1246 of the platform and the top surface 1204 of the mount assembly base member are positioned in parallel planes. A coating or sheet of low-friction material such as, for example, Teflon™, can cover the lower surface 1246 of the platform or the top surface 1204 of the mount assembly base member 1202. One skilled in the art will appreciate that other low-friction materials are contemplated. Thus, in use, the platform can be selectively moved in the first and second axis within the platform plane under the control of the platform adjustment mechanism 1250. The low-friction coating allows this motion to take place with minimal friction.

It is contemplated that the orientation control mechanism 1260 can comprise any combination of a magnetic lock 1600, a tilt and rotation mechanism 1290, a fine be mechanism 1300, and a coarse height mechanism 1310. In one aspect, and as one will appreciate, the bottom of the orientation control mechanism is disposed onto and can be selectively slid along the upper surface 1244 of the platform 1242. The upper surface of the platform can also be coated with low-friction material. This low-friction coating allows the operator to readily position the housing of the orientation control mechanism onto a desired portion of the upper surface of the platform. The orientation control mechanism can comprise a magnetic lock 1600 that is housed within a bottom portion of a housing. Upon movement of a magnet control knob 1602, which extends beyond the exterior of the housing, the magnetic lock 1600 is movable from a retracted, non-engaged position, to an engaged position in which a magnet 1604 is brought into attractive contact with the upper surface of the platform. As one will appreciate, when the magnetic lock is in the engaged position, the housing of the orientation control mechanism is fixed relative to the platform due to the attraction of the magnet and the platform. However, even if the magnetic lock 1600 is in the engaged position, the housing can slide on the upper surface of the platform if sufficient force is exerted onto the housing or the connected table assembly.

As noted above, the orientation control mechanism 1260 can further comprise a tilt and rotation mechanism 1290, a fine height mechanism 1300, and a coarse height mechanism 1310. The tilt and rotation mechanism 1290 allows the table plane defined by the table member to be positioned at a desired orientation with respect to an upright axis, which extends generally along the longitudinal axis of the orientation control mechanism and is substantially normal to the longitudinal axis of the second rail. In one aspect, the tilt and rotation mechanism 1290 comprises a ball-joint lock assembly 1292 having a distal end 1294 and a proximal end 1296. In one aspect, the table subassembly 1210 is mounted to the distal end of the ball-joint lock assembly. As discussed below, in one aspect, it is contemplated that the table subassembly is releaseably mounted. The ball-joint lock assembly has a friction lock member 1298 that allows the ball-joint lock assembly to move between a locked position, in which the table plane of the table member is fixed at a selected orientation relative to the upright axis, and an unlocked position, in which the table member is freely movable about the upright axis. It is contemplated that, in an intermediate position between the locked and unlocked positions, the table member can be moved into a desired position by exerting sufficient force on the table/platform member to overcome the friction lock of the ball-joint lock assembly.

In one aspect, the table plane of the table member further defines an x-axis and a y-axis that form a common coordinate system. As one will appreciate, the ball-joint lock assembly is constructed and arranged for selectively adjusting and securing the tilt of the table member at selected angles relative to the respective x and y axis of the table plane, which positions the table member is the desired orientation. In this aspect, the selected angle of the respective x and y axis is less than and including about 60 degrees (i.e., +/−30 degrees). In another aspect, the selected angle is less than and including about 45 degrees (i.e., +/−22.5 degrees). In yet another aspect, the selected angle is less than and including about 30 degrees (i.e., +/−15 degrees). Thus, in operation, selective manipulation of the ball-joint lock assembly by the operator allows the table member to be oriented in a desired table surface plane.

The fine height mechanism 1300 comprises a cap 1302, an upright shaft member 1304, a first housing 1306, and a fine height control mechanism 1308. The cap 1302 has a top surface 1303 to which, in one exemplified aspect, the proximal end 1296 of the ball-joint lock assembly 1292 is disposed. The cap is further connected to the upright shaft member 1304 that extends substantially co-axial to the longitudinal axis of the orientation control mechanism. The first housing 1306 is constructed and arranged for support and rotatable connection of the shaft member. In use, the upright shaft member is operatively engaged with the first housing such that the upright shaft member can be selectively rotated about the upright axis. The fine height control mechanism is constructed and arranged for selective bidirectional movement of the distal end of the upright shaft, with its attached cap, along the upright axis relative to atop of the first housing. In use, clockwise or counter-clockwise rotation of the fine height control mechanism 1308 allows the cap 1302 to be raised/lowered to the desired height. Thus, upon movement of a height control wheel 1309 of the fine height control mechanism 1308, the cap can be raised or lowered as desired. In one embodiment, the cap can be moved relative to the top of the first housing member between end points along the upright axis less than and including about 50 min. In another aspect, less than and including about 30 mm. In yet another aspect, less than and including about 20 min. In another aspect, less than and including about 10 mm.

The coarse height mechanism 1310 is housed within a second housing 1312 and is constructed and arranged for selective bi-directional movement of the first housing 1306 relative to the second housing 1312 along the upright axis of the orientation control mechanism 1260. At least a portion of the first housing is movably housed within an upper portion of a defined interior volume of the second housing. Further, the coarse height mechanism 1310 comprises a bias element, such as a spring, that is housed within a lower portion of the defined interior volume of the second housing. In one aspect, the magnetic lock 1600 is disposed within the interior volume of the second housing and is positioned at the bottom of the second housing. In this aspect, the bias element is positioned intermediate the magnetic lock and the first housing. The first housing can have a groove 1307 defined within a portion of the exterior surface of the first housing. The groove 1307 extends generally parallel to the upright axis and is sized and shaped to cooperate with a male protrusion 1303 defined in an interior surface of the interior volume of the second housing. The cooperating groove and male protrusions of the respective first and second housing allow for relative bidirectional movement of the first housing with respect to the second housing to occur without relative rotation of the first housing with respect to the second housing.

Thus, upon movement of a lever control 1318 of the coarse height control mechanism, the first housing 1306 can be, relative to the second housing 1312, raised or lowered as desired between a top, extended, position and a lowered, contracted, position. To accommodate the movement of the lever control 1318, the housing defines a shaped slot 1320 in one side having an upright portion 1322, a lower longitudinally extending portion 1324 proximate the bottom of the second housing, and au upper longitudinally extending portion 1326 proximate the top of the second housing. In the lowered position, the lever control 1318 is in the lower longitudinally extending portion proximate the bottom of the second housing and the bias element 1314 is in its most compressed position. In order to raise the first housing to its top position relative to the second housing, the lever control 1318 is lifted upward the extent of the upright portion of the slot 1322 and is then slid into and seated within the upper longitudinally extending portion of the slot proximate the top of the second housing. The bias element 1314 acts against a bottom portion of the first housing such that the first housing is urged toward a top portion of the second housing and toward its top position as the lever control is positioned in the upper portions of the defined slot.

In one aspect, the release mount assembly 1330 of the small-animal mount assembly comprises a shoe member 1340, a foot member 1350 and a lock assembly 1360. In one aspect, the shoe member defines a shaped trough 1342. The trough has a pair of opposing guide edges 1343 and a back edge 1344 extending therebetween respective ends of the opposing guide edges. A portion of the back edge of the trough forms an angled flange surface 1346 that extended outward at an angle to overlie a portion of the interior of the trough. The foot member 1350 is sized and shaped for complementary disposition therein a portion of the trough of the shoe member. In one aspect, the foot member 1350 had a first beveled edge 1352 and a second opposed beveled edge 1354. The first beveled edge 1352 being sized and shaped for complementary engagement with the angled flange surface 1346 of the shoe member.

In one aspect, the shoe member 1340 is connected to a distal portion of the orientation control mechanism (such as, in one aspect, the distal end of the ball-joint lock assembly member) such that the defined trough faces outward and the back surface of the foot member 1350 is connected to the bottom face of the platform member. In an alternative aspect, if the ball-joint lock assembly is not a part of the orientation control mechanism, the shoe member can be connected to the top surface of the cap of the course height mechanism.

The lock assembly 1360 comprises a lock lever 1362 that is rotatably mounted to the shoe member 1340. The lock lever has an eccentrically shaped edge surface 1364, a portion of which has a beveled cross-sectional shape 1366. The lock lever 1362 being movable between a clamped position and an unclamped position. In the clamped position, the beveled portion 1366 of the edge surface of the lock lever engages a portion of the second beveled edge 1354 of the foot member and acts to force a portion of first beveled edge 1352 of the foot member into a locked position with a portion of the angled flange surface 1346 of the shoe member. Thus, in one aspect, the flange surface of the shoe member is forced into complementary engagement with the first beveled edge of the foot member and the beveled edge of the lock lever is forced into complementary engagement with the second beveled edge when the lock lever is positioned in the clamped position. In the unclamped position, as one will appreciate, the foot member can be selectively removed from the trough of the shoe member. It will be appreciated that it is contemplated that the foot member can be mounted on the distal portion of the orientation control mechanism and, in this aspect, the shoe member can be mounted to the bottom face of the platform member.

In one aspect, the platform has at least one leg mounted to and extending from the bottom face of the platform member. Each leg 1380 has a predetermined height that is less than a height of the foot member.

As noted above, the table member 212 has a top surface 214 that is disposed in the table surface plane. The table subassembly 210 can also comprise a plurality of ECG electrode contact pads 220, at least one grid of electronic heating elements 230, and/or at least one thermocouple 240. In one aspect, the plurality of ECG contact pads is operatively attached to the top surface 214 of the table member. Each ECG contact pad senses an ECG signal within a portion of a small animal that is secured against the ECG contact pad. Each ECG contact pad 220 is spaced from an adjacent contact pad and can be positioned so that each one of the feel/paws of the small animal can be selectively positioned against one of the ECG contact pads. In one aspect, the plurality of ECG contact pads comprises four ECG contact pads that are positioned in a spaced "X" configuration so that the respective feet of the small animal can be positioned in a splayed position. Each ECG contact pad 220 generates an ECG signal 222 representative of the sensed ECG. The ECG signal can be transmitted through an A/D converter (not shown) to a control apparatus 250 on ECG signal line 224. This ECG signal can be transmitted through an isolated ECG amplifier and digital or analog anti-aliasing filter (not shown) to remove noise and amplify the signal before processing.

The grid of electronic heating elements 230 is disposed onto the top surface 214 of the table member 212 and is electrically coupled to the control apparatus 250. The temperature of the top surface 214 of the table member can be adjusted via the control apparatus so that a small animal's temperature can be maintained within a desired range when the small animal is positioned onto the top surface 214 of the table member.

If used, the thermocouple 240 is connected to the top surface of the table member and can be positioned such that a portion of the small animal overlies the thermocouple when the small animal is secured to the top surface 214. In one aspect, the thermocouple is positioned near the center of the top surface 214 of the table member 212 and is spaced from the at least one grid of electronic heating elements 230. The thermocouple 240 generates a temperature signal 242 representative of the sensed temperature of the small animal proximate the thermocouple. The temperature signal 242 can be transmitted through an A/D converter (not shown) to the control apparatus 250 on temperature signal line 244. This temperature signal can be transmitted through an isolated amplifier and digital or analog anti-aliasing filter (not shown) to remove noise and amplify the signal before processing.

The table subassembly 210 can also comprise a rectal temperature probe 246. The rectal temperature probe generates an internal temperature signal 248 representative of the sensed internal temperature of the small animal with the rectum of the small animal the thermocouple. The internal temperature signal 248 can be transmitted through an A/D converter (not shown) to the control apparatus on temperature signal line 249. This internal temperature signal can be transmitted through an isolated amplifier and digital or analog anti-aliasing filter (not shown) to remove noise and amplify the signal before processing.

In one aspect, if external embryonic imaging is desired, the table subassembly 210 can comprise a walled dish 360 and a dish support mechanism 370. The dish 360 has a peripheral wall 362 and defines an opening 364 in the bottom of the dish. The dish is formed of a substantially rigid material, such as, for example, a rigid plastic. A pliable membrane 366 defining a slit 368 is connected to the opening to form a moisture proof connection. In one aspect, in a relaxed position, the slit in the membrane is closed and is moisture proof. In a stretched position, the slit in the membrane is open. The pliable membrane can be a rubber membrane. In another aspect, the slit 368 in the membrane 366 is open in both the relaxed and stretched positions.

The dish 360 can be selectively held in position relative to the top surface 214 of the table member 212 by selective actuation of a dish support mechanism 370. The dish support mechanism has an arm member 372 and a fastener 374. The arm member has an upper portion 376 that is constructed and arranged for selectively clamping onto a portion of the wall 262 of the dish. As one will appreciate, the dish 260 can be removed by removing knurled screw 378. The arm member 372 has a lower portion defining an elongate slot 379. The fastener 374 passes through the slot 379 and can selectively secure the lower portion of the arm member to an edge of the platform member. In use, the position of an attached dish can be adjusted by loosening the fastener 374, adjusting the dish 360 into the desired position, and tightening the fastener 374 to secure the dish 260 in the desired position.

In certain externalized procedures, the small animal is secured to the top surface 214 of the table member and the dish 260 is disposed onto the small animal such that the pliable membrane 366 is in the stretched open position with the "open" slit forming a moisture proof seal between the small animal and the dish. In this example, embryos can be passed through the slit in the rubber membranes and can be imaged in the dish while still attached to the small animal.

The table subassembly 210 can also comprise a clamp member 380 secured to a portion of the top surface 214 of the table member. In an alternative aspect, the clamp member is connected to a portion of the edge of the platform member. In one aspect, the clamp member 380 is constructed and arranged for grasping a portion of a conical small animal mask 382 that is shaped and sized for fit with the snout of the small animal. The mask 382 is connected to at least one anaesthetic line that is coupled to an external anaesthetic source, not shown. In an alternative aspect, the clamp member 380 can selectively grasp a portion of the at least one anaesthetic line.

Needle Injection Assembly

Referring now to FIGS. 3243, one embodiment of the needle injection assembly 400 is shown. The needle injection assembly is constructed and arranged for operator control of a needle's insertion point, insertion depth, and angle of penetration. The needle injection assembly 400 further can be constructed and arranged for controlling a needle plunger 433 of the needle 432.

In one example, the needle injection assembly 400 includes the base member 402 (which is connected to the third rail 36 as described above), an injector subassembly 420, and a carriage subassembly 450. The injector subassembly 420 includes an injector unit 430 that has an elongated needle 432 operatively mounted therein. The needle 432 has a longitudinal length and a distal end 434. The carriage subassembly 450 is connected to the base member 402 and provides controls for setting the needle's insertion point in the small animal in a desired plane, which is typically the same plane as the scanhead unit is set up to image, i.e., the desired image plane. The carriage subassembly 450 also provides controls for pivoting the needle 432 so that the operator can set a desired angle of penetration to the needle's insertion point in the small animal. The carriage subassembly 450 can include a rotation adjustment mechanism 460, a height adjustment mechanism 470, a first lateral adjustment mechanism 480, a second lateral adjustment mechanism 490, a first tilt adjustment mechanism 500, a second tilt adjustment mechanism 510, and an articulating armature subassembly 530.

The rotation adjustment mechanism 460 is constructed and arranged for rotating portions of the carriage subassembly mounted thereon about an upright axis. In one example, the rotation adjustment mechanism includes a housing 462 that is connected to the top surface 404 of the base member 402. The rotation adjustment mechanism 460 further includes a conventional bearing 464 mounted within the housing that connects to and supports a frame member 465. The frame member 465 has a base 467 that is operatively connected to the bearing of the rotation adjustment mechanism. As one will appreciate, the frame member 465 can rotate about an upright axis extending normal to the longitudinal axis of the third rail and through the center of the bearing. The rotation adjustment mechanism 460 can include a rotation lock knob 466 for selectively locking the rotation of the frame member so that the amount of rotation of the frame member about the upright axis is limited. The rotation adjustment mechanism can also include a fine rotation adjustment control knob 468 that allows the operator to rotate the frame member through a limited angle about the upright axis after the rotation lock knob has been engaged. In one embodiment the limited angle is about and between 10 degrees (+/−5 degrees). In another embodiment, the angle is about and between 8 degrees (+/−4 degrees). In yet another embodiment, the angle is about and between 6 degrees (+/−3 degrees).

The height adjustment mechanism 470 is operatively connected to the frame member 465 and is constructed and arranged for raising portions of the carriage subassembly supported thereon along an upright axis. The height adjustment mechanism includes a platform 472 that can be selectively moved along an upright axis parallel to the upright axis of the rotation adjustment mechanism 460 between a top fixed end point and a bottom fixed end point. In use, rotation of the height adjustment knob 474 of the height adjustment mechanism moves the platform of the height adjustment mechanism bi-directionally relative to the base 467 of the frame member along the upright axis. As one will appreciate, movement of the platform 472 upward or downward along the upright axis depends upon the direction the height adjustment knob 474 is moved. In one embodiment, the platform 474 of the height adjustment mechanism can be moved about a center point between fixed end points about and between +/−25 mm. In another embodiment, about and between +/−18 degrees. In another example, about and between +/−13 degrees.

The first lateral adjustment mechanism 480 is connected to and is mounted onto the top surface 476 of the platform 472. The second lateral adjustment mechanism 490 is connected to and mounts thereon a selectively movable top surface 482 of the first lateral adjustment mechanism 480. The first adjustment mechanism 500 is connected to and mounts thereon a selectively movable top surface 492 of the second lateral adjustment mechanism 490. Similarly, the second tilt adjustment mechanism 510 is connected to and is mounted onto a selectively movable top surface 502 of the first tilt adjustment mechanism 500. The articulating armature subassembly 520 is operatively connected to a selectively movable top surface 512 of the second tilt adjustment mechanism 510.

The first lateral adjustment mechanism 480 is constructed and arranged for moving the top surface 482 of the first lateral adjustment mechanism relative to the platform 472 and parallel to an x-axis defined by the platform. This allows the top surface 482 of the first lateral adjustment mechanism 480 to shift toward or away from the proximal end of the third rail 36. In use, rotation of a first lateral adjustment knob 484 moves the top surface 482 of the first lateral adjustment mechanism 480 bi-directionally relative to the platform. Similarly, the second lateral adjustment mechanism 490 is constructed and arranged for moving the top surface 492 of the second lateral adjustment mechanism relative to the top surface 482 of the first lateral adjustment mechanism 480 and parallel to a y-axis defined by the platform (which is normal to the defined x-axis). This allows the top surface 492 of the second lateral adjustment mechanism to shift toward or away from the respective side edges of the third rail 36. In use, rotation of a second lateral adjustment knob 494 moves the top surface 492 of the second lateral adjustment mechanism bi-directionally relative to the top surface 482 of the first lateral adjustment mechanism. As one will appreciate, in another example, the second lateral adjustment mechanism 490 can be connected to and mounted onto the top surface 476 of the platform 472 and the first lateral adjustment mechanism 480 can then be connected to and mounted thereon the selectively movable top surface 492 of the second lateral adjustment mechanism 490.

The articulating armature subassembly 520 has a mount member 522 that is, in one example, connected to the top surface 512 of the second tilt adjustment mechanism 510. The mount member 522 of the articulating armature subassembly defines a mount plane that further defines an x-axis and a y-axis. One will appreciate that the x and y axis of the mount plane form a common coordinate system. In one example, the first tilt adjustment mechanism 500 is operatively connected to the top surface 492 of the second lateral adjustment mechanism 490 and is constructed and arranged for selectively adjusting and securing the tilt of the mount member 522 relative to and about the y-axis of the mount member. The second tilt adjustment mechanism 510 is operatively connected to the top surface 502 of the first tilt mechanism 500 and is constructed and arranged for selectively adjusting and securing the tilt of the mount member 522 relative to the x-axis of the mount member.

In this configuration, the first and the second tilt adjustment mechanisms 500, 510 allow the mount member 522 to be angled with respect to the respective y-axis and x-axis of the mount member. In one embodiment, the angle is less than and including about 40 degrees +/−20 degrees). In another embodiment, the angle is less than and including about 20 degrees (i.e., +/−10 degrees). In yet another embodiment, the angle is less than and including about 10 degrees (i.e., +/−5 degrees).

One will appreciate that, in another example, the second tilt adjustment mechanism 510 can be connected to and mounted thereon a selectively movable top surface of the uppermost of the first or second lateral adjustment mechanisms. In this example, the first tilt adjustment mechanism 500 is connected to and is mounted onto the selectively movable top surface 512 of the second tilt adjustment mechanism 510. The mount member of the articulating armature subassembly 520 would be operatively connected to the selectively movable top surface 502 of the first tilt adjustment mechanism.

The articulating armature assembly 520 includes a plurality of cooperative arm members 530 that are operatively connected to the mount member and can be moved by selective actuation of an armature control mechanism 524. As one will appreciate, selective manipulation of the rotation adjustment mechanism 460, the height adjustment mechanism 470, the first lateral adjustment mechanism 480, the second lateral adjustment mechanism 490, the first tilt adjustment mechanism 500, and/or the second tilt adjustment mechanism 510 allows the mount member 522 of the articulating armature assembly to be positioned into a desired mount plane defined by a plane extending through the mount member. The injector unit 430 of the injector subassembly 420 is operatively mounted within a seat 532 positioned at a distal portion 534 of the plurality of cooperative arm members such that the distal end 434 of the needle 432 extends beyond the plurality of cooperative arm members. As one will appreciate, the injector unit 430 is positioned in a needle plane that is normal to the mount plane of the mount member 522.

The articulating armature assembly 520 is constructed and arranged for rotating the injector unit 430 about the distal end 434 of the needle in a desired needle plane that is normal to the desired mount plane. In operation, the desired needle plane is substantially coplanar to the desired image plane. As an armature control knob 526 is selectively rotated, the injector unit is between a first fixed end point in which the needle 432 is angled at a lower angle of penetration θ relative to an upright axis to a second fixed end point in which the needle is angled at a higher angle of penetration θ relative to the upright axis. Thus, the operator can selective set the exact insertion point of the needle and, via manipulation of the control of the articulating armature assembly, can select, within the desired needle plane, a desired angle of penetration θ of the needle into the subject small animal. The articulating armature assembly 520 also includes a position brake mechanism 540 that can be selectively engaged to fix the plurality of cooperative arm members is a desired position. By "fixing" the plurality of cooperative arm members is the desired position, the operator can "fix" the desired angle of penetration θ of the needle. By tightening knob 542 onto a portion of the mount member, the plurality of cooperative arm members can be selectively "locked" into position.

The injector subassembly 420 includes the injector unit 430 mounted thereon the seat 532 of the articulating armature assembly. In one example, the injector unit 430 includes a plunger 433, a barrel 436, and the elongate needle 432. The plunger 433 is movable within a defined chamber 437 of the barrel 436. A bore of the needle 432 is in communication with the chamber of the barrel. In use, the plunger 433 can by manually moved in a conventional manner to inject a desired amount of material into the subject small animal or to draw material thereinto the chamber of the barrel. In another example, the injector unit 430 also includes a conventional actuator 440 that is operatively coupled to the plunger 433. In this example, the actuator 440 is also electrically coupled to a plunger control unit 442. The user can actuate controls on the plunger control unit 442 to retract or extend the plunger of the injector unit a desired amount.

The injector subassembly further comprises a needle insertion mechanism 540 constructed and arranged for controlling the extension and the retraction of the injector unit 430 relative to the seat 532 of the plurality of cooperative arm members 530. In use, rotation of a needle insertion control knob 542 of the needle insertion mechanism moves the injector unit 430, and the attached needle, bi-directionally along the seat and along longitudinal axis of the needle 432. As one will appreciate insertion or retraction movement of the injector unit and the attached needle depends upon the direction the needle insertion control knob 542 is moved.

Referring now to FIGS. 64-67, an alternative embodiment of the needle injection assembly 1400 is shown. As noted above, the needle injection assembly is constructed and arranged for operator control of a needle's insertion point, insertion depth, and angle of penetration. In one aspect, the needle injection assembly 1400 further can be constructed and arranged for controlling a needle plunger 433 of the needle 432.

In one aspect, the needle injection assembly 1400 comprises an injection assembly base member 1402 (which is connected to the first rail as described above), an injector subassembly 420, and a carriage subassembly 1450. The injector subassembly 420 comprises an injector unit 430 that has an elongated needle 432 operatively mounted therein. The needle 432 has a longitudinal length and a distal end 434. The carriage subassembly 1450 is connected to the injection assembly base member 1402 and provides controls for setting the needle's insertion point in the small animal in a desired plane, which is typically the same plane as the scanhead unit is set up to image, i.e., the desired image plane. The carriage subassembly 1450 also provides controls for orienting the needle 432 so that the operator can set a desired angle of penetration to the needle's insertion point in the small animal. The carriage subassembly 1450 can comprise a rotation adjustment mechanism 1460, a first height adjustment mechanism 1470, an injection angle adjustment mechanism 1490, a second height adjustment mechanism 1500, and a lateral adjustment mechanism 1490.

The carriage subassembly 1450 comprises a fifth rail 1035. The rotation adjustment mechanism 1460 is constructed and arranged for rotating the fifth rail 1035 about an upright axis extending substantially transverse to the injection assembly base member 1402 and that is substantially parallel to the longitudinal axis of the fifth rail. In one aspect, the rotation adjustment mechanism comprises a housing 1462 that is connected to the top surface 1404 of the injection assembly base member 1402. The rotation adjustment mechanism further comprises a conventional bearing mounted within the housing that connects to and supports a frame member 1465. The frame member has a base that is operatively connected to the bearing of the rotation adjustment mechanism. As one will appreciate, the frame member can rotate about the upright axis. The rotation adjustment mechanism 1460 can comprise a rotation lock knob 1466 for selectively locking the rotation of the frame member so that the amount of rotation of the frame member about the upright axis is limited. The rotation adjustment mechanism can also comprise at least one preset position, such as, for example, a preset position substantially co-axial to the longitudinal axis of the first rail and a preset position substantially transverse to the longitudinal axis of the first rail.

The first height adjustment mechanism 1470 is operatively connected to the frame member 1465 and is constructed and arranged for raising portions of the carriage subassembly 1450 supported thereon along an upright axis. The first height adjustment mechanism comprises a housing 1472, a threaded rod member 1474, and an injection assembly mount member 1476. The first height adjustment housing 1472 is mounted thereon the frame Member. One end of the fifth rail is mounted to the first height adjustment housing such that it extends from the top of the housing parallel to the upright axis. The first height adjustment mechanism also comprises an end member 1478 mounted at the distal end of the fifth rail. The end member defines a cavity for operative receipt of a bearing. The proximal end of the threaded rod member is rotatably mounted to the first height adjustment housing and the distal end of the threaded rod is rotatably mounted in the bearing in the end member such that the threaded rod is positioned substantially parallel to the longitudinal axis of the fifth rail. As shown in the figures, the proximal end of the rod member is housed within the first height adjustment housing and has a beveled gear attached thereto. A crank member 1471 is provided having an end disposed therein the height adjustment housing that has a complementary beveled gear mounted thereon. In use, rotation of the crank member results in a rotation of the threaded rod member about its axis. As one will appreciate, and as shown, bearings can be provided on the threaded rod member and the crank member.

The injection assembly mount member 1476 is mounted to the fifth rail and defines a threaded bore 1478 that is sized and shaped for complementary engagement with the threaded surface of the threaded rod member 1474. In use, when the crank member 1471 is rotated and the threaded rod member rotates, the injection assembly mount member 1476 selectively moves bi-directionally relative to the top of the housing along the longitudinal axis of the fifth rail. As one will appreciate, upward or downward movement of the injection assembly mount member along the threaded rod member depends upon the direction the crank member is moved.

To selectively secure the injection assembly mount member 1476 in a desired position, a rail lock assembly 1480 is provided. In this aspect, the rail lock assembly 1480 comprises a body member 1482 that is mounted to portions of the back face 1479 of the injection assembly mount member such that a portion of the body member overlies the back face of the fifth rail. The portion of the body member defines a threaded bore 1484 sized and shaped for complementary receipt of a threaded knob 1486. In use, the injection assembly mount member 1476 is raised/lowered to the desired position as described above and the threaded knob 1486 is rotated such that a distal end of the knob 1486 frictionally engages the back face of the fifth rail to frictionally lock the injection assembly mount member into position relative to the fifth rail.

In one aspect, the injection angle adjustment mechanism 1490 is connected to and is mounted onto a top surface 1473 of the injection assembly mount member 1476. The second height adjustment mechanism 1500 is connected to and mounts thereon a mount surface 1492 of a selectively movable member 1494 of the injection angle adjustment mechanism 1490. The lateral adjustment mechanism 1510 is connected to and mounts thereon a mount surface 1502 of a selectively movable member 1504 of the second height adjustment mechanism 1500. The injector subassembly 420 is operatively connected to and mounts thereon a mount surface 1512 of a selectively movable mount member 1514 of the lateral adjustment mechanism 1510.

The injection angle adjustment mechanism 1490 is constructed and arranged for rotating a member 1494 of the injection angle adjustment mechanism relative to the top surface 1473 of the injection assembly mount member. This allows the mount surface 1492 of the injection angle adjustment mechanism to be rotated about an axis substantially transverse to the longitudinal axis of the fifth rail. In use, rotation of an injection angle adjustment knob 1496 rotates the movable member 1494 of the injection angle adjustment mechanism relative to the top surface 1473 of the injection assembly mount member.

The second height adjustment mechanism 1500 is constructed and arranged for moving a member 1504 of the second height adjustment mechanism relative to the mount surface 1492 of the movable member 1494 of the injection angle adjustment mechanism along an axis substantially parallel to a rail plane that bisects the longitudinal axis of the fifth rail. This allows the mount surface of the second height adjustment mechanism to shift upwards or downwards in a plane substantially parallel to a rail plane. In use, rotation of a height adjustment knob 1506 moves the movable member 1504 of the height adjustment mechanism bi-directionally along its movement axis relative to the mount surface 1492 of the lateral adjustment mechanism.

Similarly, the lateral adjustment mechanism 1510 is constructed and arranged for moving the mount surface 1512 of the lateral adjustment mechanism relative to the mount surface 1502 of the movable member 1504 of the second height adjustment mechanism along an axis that is substantially normal to the rail plane of the fifth rail. This allows the mount surface 1512 of the lateral adjustment mechanism to shift toward or away from the rail plane of the fifth rail. In use, rotation of a lateral adjustment knob 1516 moves the movable member 1514 of the lateral adjustment mechanism hi-directionally along its movement axis relative to the mount surface of the height adjustment mechanism.

As one will appreciate, in another aspect, the lateral adjustment mechanism 1510 can be connected to and mounted onto the top surface 1473 of the injection assembly mount member and the second height adjustment mechanism 1500 can then be connected to and mounted thereon the mount surface 1512 of the selectively movable member 1514 of the lateral adjustment mechanism.

As one will appreciate, selective manipulation of the rotation adjustment mechanism 1460, the first height adjustment mechanism 1470, the injection angle adjustment mechanism 1490, the second height adjustment mechanism 1500, and the lateral adjustment mechanism 1510 allows the mount member 1504 of the lateral adjustment mechanism to be positioned into a desired mount plane defined by a plane extending through the mount member. The injector unit 439 of the injector subassembly 420 is operatively mounted to the mount member within a seat 532 positioned on the mount member of the lateral adjustment mechanism such that the distal end 434 of the needle 432 extends outwardly from in a desired needle plane.

In operation, the desired needle plane is substantially coplanar to the desired image plane. Thus, the operator can selective set the exact insertion point of the needle and, via manipulation of the controls of the respective adjustment mechanisms, can select, within the desired needle plane, a desired angle of penetration θ of the needle into the subject small animal.

As noted above, the injector subassembly 420 includes the injector unit 430 mounted thereon the seat 532 of the articulating armature assembly. In one example, the injector unit 430 includes a plunger 433, a barrel 436, and the elongate needle 432. The plunger 433 is movable within a defined chamber 437 of the barrel 436. A bore of the needle 432 is in communication with the chamber of the barrel. In use, the plunger 433 can by manually moved in a conventional manner to inject a desired amount of material into the subject small animal or to draw material thereinto the chamber of the barrel. In another example, the injector unit 430 also includes a conventional actuator 440 that is operatively coupled to the plunger 433. In this example, the actuator 440 is also electrically coupled to a plunger control unit 442. The user can actuate controls on the plunger control unit 442 to retract or extend the plunger of the injector unit a desired amount.

The injector subassembly further comprises a needle insertion mechanism 540 constructed and arranged for controlling the extension and the retraction of the injector unit 430 relative to the mount member. In use, rotation of a needle insertion control knob 542 of the needle insertion mechanism moves the injector unit 430, and the attached needle, bi-directionally along the seat and along longitudinal axis of the needle 432. As one skilled in the art will appreciate, insertion or retraction movement of the injector unit and the attached needle depends upon the direction the needle insertion control knob 542 is moved.

It will be appreciated that the combination of the releasable coupling between the base members of the respective assemblies and the respective rails allows for repositioning of the assemblies while maintaining alignment and relative positioning of the various components. The assemblies can be set up and aligned in their respective procedure positions and subsequently moved out of position to, for example, replace the small animal on the table member. The assemblies can then be returned to their procedure positions to and be aligned in the same manner as for the previous small-animal on the table member. In this manner, it will be recognized that the potentially time-consuming process of re-aligning the assemblies can be avoided. Once the small-animal on the table member is imaged (and injected), a second small-animal can easily be introduced into the field of view with minimal adjustment to either the scanhead unit or, if used, the injector unit since the small-animal mount assembly can slide out of the image plane on its own rail.

The imaging system 10 can also comprise the computer 20 having a system processor 22. The processor 22 can be coupled to a display or monitor 24 and to a user input device 26, such as a keyboard, mouse, or other suitable device. If the monitor 24 is touch sensitive, then the monitor 24 itself can be employed as the user input device 26. A computer readable storage medium 28 is coupled to the processor. As one will appreciate, the operation of the scanhead assembly 100, table subassembly 210 of the small-animal mount assembly 200, and, if used, the needle injection assembly 400, could be operatively coupled to and controlled by the computer 20. Further, if used, the scanhead articulation unit could be operatively coupled to and controlled by the computer 20. As one skilled in the art will appreciate, the computer readable medium 28 can include hardware and/or software such as, by way of example only, magnetic disks, magnetic tape, optically readable medium such as CD ROM's, and semi-conductor memory such as PCMCIA cards. In each aspect, the medium 28 can take the form of a portable item such as a small disk, floppy diskette, cassette, or it can take the form of a relatively large or immobile item such as hard disk drive, solid state memory card, or RAM coupled to the processor 22. It should be noted that the above listed example mediums 28 can be used either alone or in combination. The display 24 could be multipurpose and also serve as a screen for the imaging system 10. Alternatively, the imaging system can have a separate screen.

Operation of the system begins by placing and securing the small animal onto the table member such that the small animal's paws are placed against the ECG pads. The rectal probe is inserted into the small-animal and the health parameters are monitored on the control apparatus 250 and/or the computer 20 throughout the imaging session. The respective controls of the mount subassembly of the small-animal mount assembly are selectively manipulated to place the table member in the desired table surface plane. In one aspect, in the embodiment shown in FIGS. 45-48, the small-animal mount assembly can be moved on the second rail until the plunger lock mechanism 206 engages a portion of the fixed stop 51 positioned intermediate the proximal and distal ends on the second rail. Alternatively, the small-animal mount assembly can be moved until a portion of the base member contacts a portion of a previously set movable stop on the second rail. In this position, the table member of the small-animal mount assembly is in the imaging field of the scanhead unit.

In one aspect, the mount of the scanhead assembly is positioned into a proximate procedure position on the first rail. In one aspect, the movable stop 50 is slid along and then secured onto the first rail at a desired procedure position that is within a few centimetres of the desired final procedure position of the mount. One will appreciate that fine adjustment to the position of the scanhead unit can be made through manipulation of the controls of the mount of the scanhead assembly.

The mount of the scanhead assembly is moved into contact with the movable stop so that the desired image plane of the scanhead unit is positioned such that the image plane bisects the portion of interest in the small-animal.

In another aspect, illustrated in FIGS. 44-63, the second rail is positioned relative to the first rail by selective positioning of the second rail base member. The small-animal mount assembly can be moved on the second rail until the plunger of the plunger lock mechanism 206 engages a desired position hole on the second rail. The magnetic lock of the orientation control mechanism releasable secures the bottom of the orientation control mechanism to the adjustable platform that is operatively connected to the base member. The controls of the orientation control mechanism are manipulated so that the height, tilt and rotation of the table member are adjusted such that the table member is positioned in the desired table plane. In this position, the table member of the small-animal mount assembly is in the imaging field of the scanhead unit.

In another aspect, the base member of the scanhead assembly is positioned and secured on a select portion of the first rail which proximates a procedure position on the first rail. The controls of the scanhead assembly are manipulated so that the scanhead unit is positioned in the desired table plane. As one will appreciate, in this position the table member of the small-animal mount assembly is in the imaging field of the scanhead unit.

As one will appreciate, when the imaging session is complete, the small-animal mount assembly and the imaging assembly can be moved away from the procedure positions on the first and second rails (toward the respective distal ends of the rails) while maintaining alignment and relative position of the small-animal mount assembly and the imaging assembly. Thus, the set image plane and the table surface plane will not change. A new small-animal can be positioned on the table member and the small-animal assembly and imaging assembly can be repositioned by relying upon the previous setting of the movable and/or fixed stops.

Figure 61:
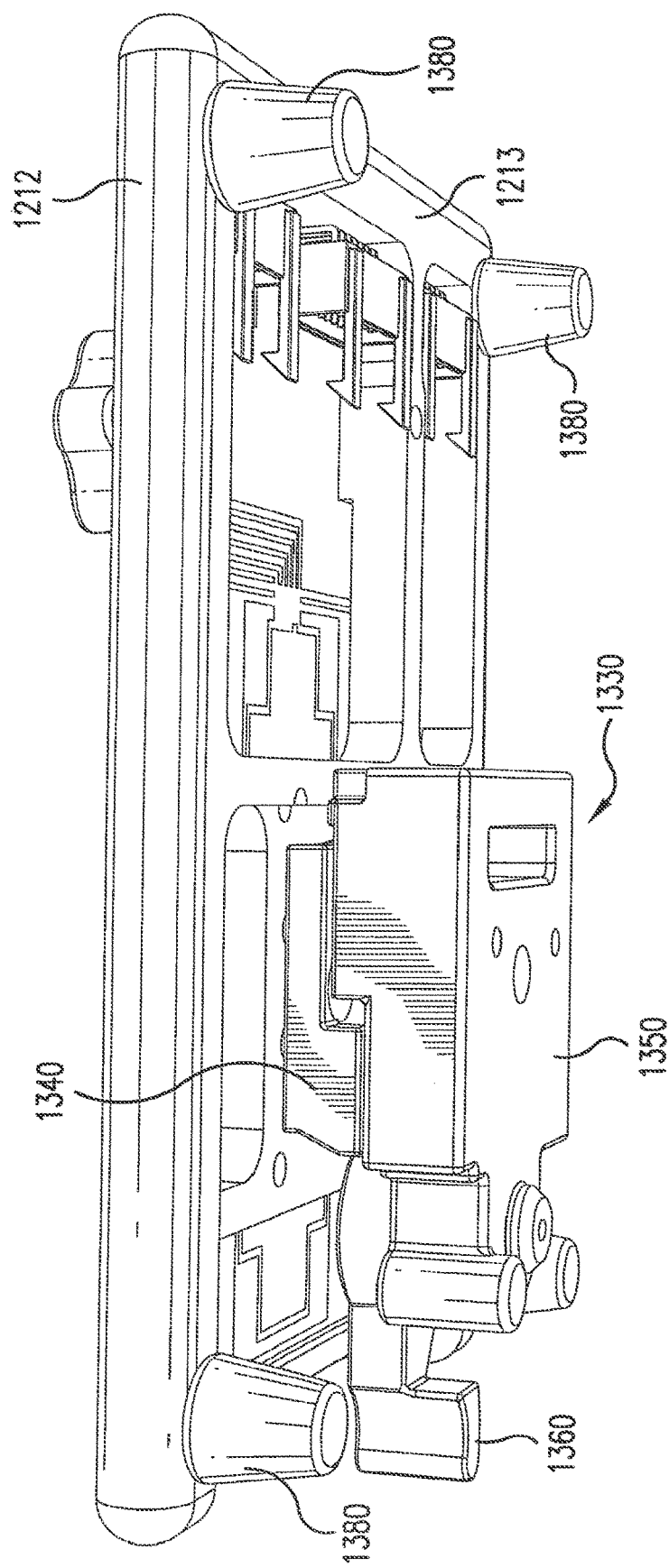
FIG. 61 is a partial semi-transparent perspective view of the release mount assembly mounted to the bottom face of the platform member.
Figure 62:
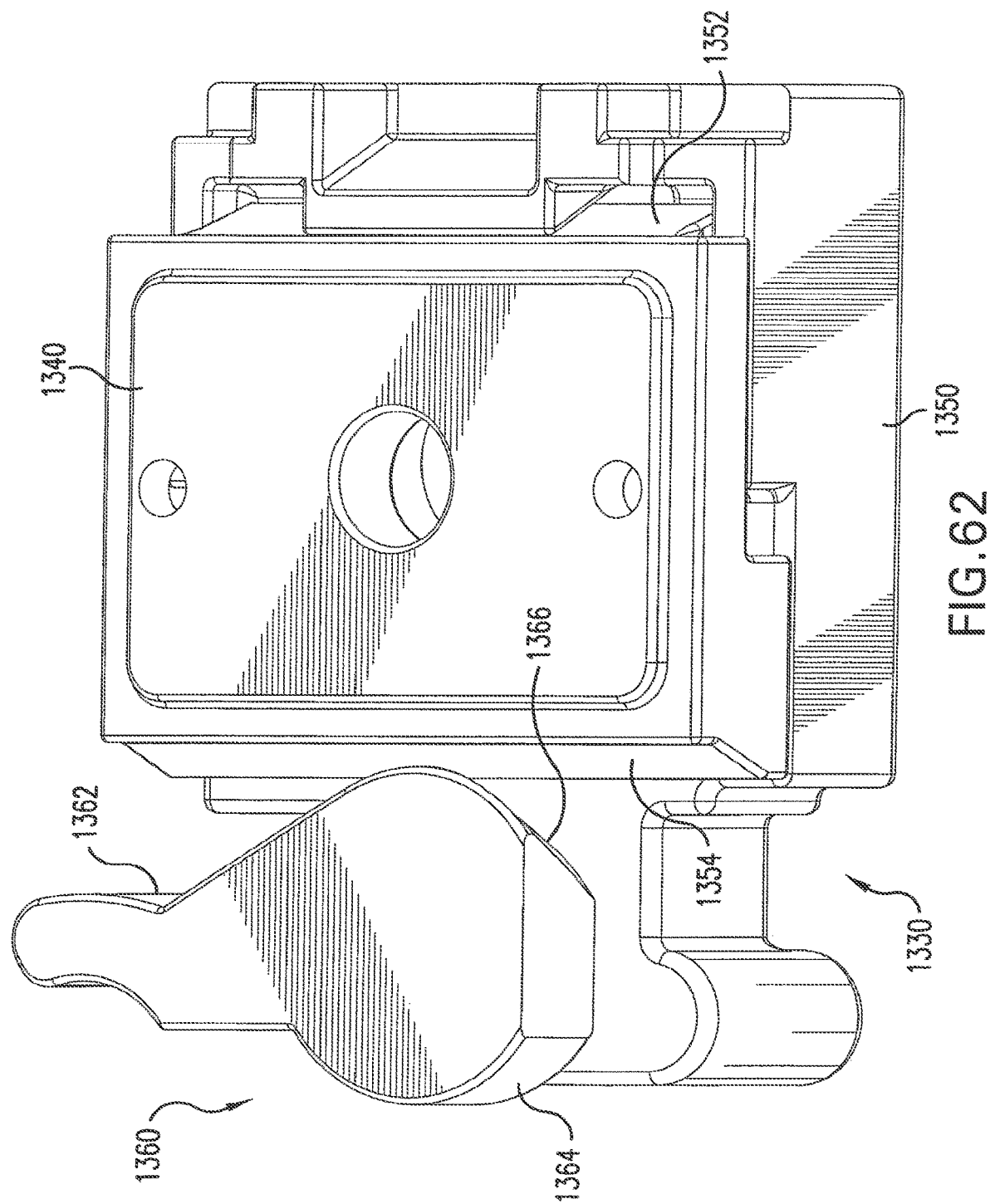
FIG. 62 is a perspective view of a shoe member, a foot member, and a lock assembly of the release mount assembly.
Figure 63:
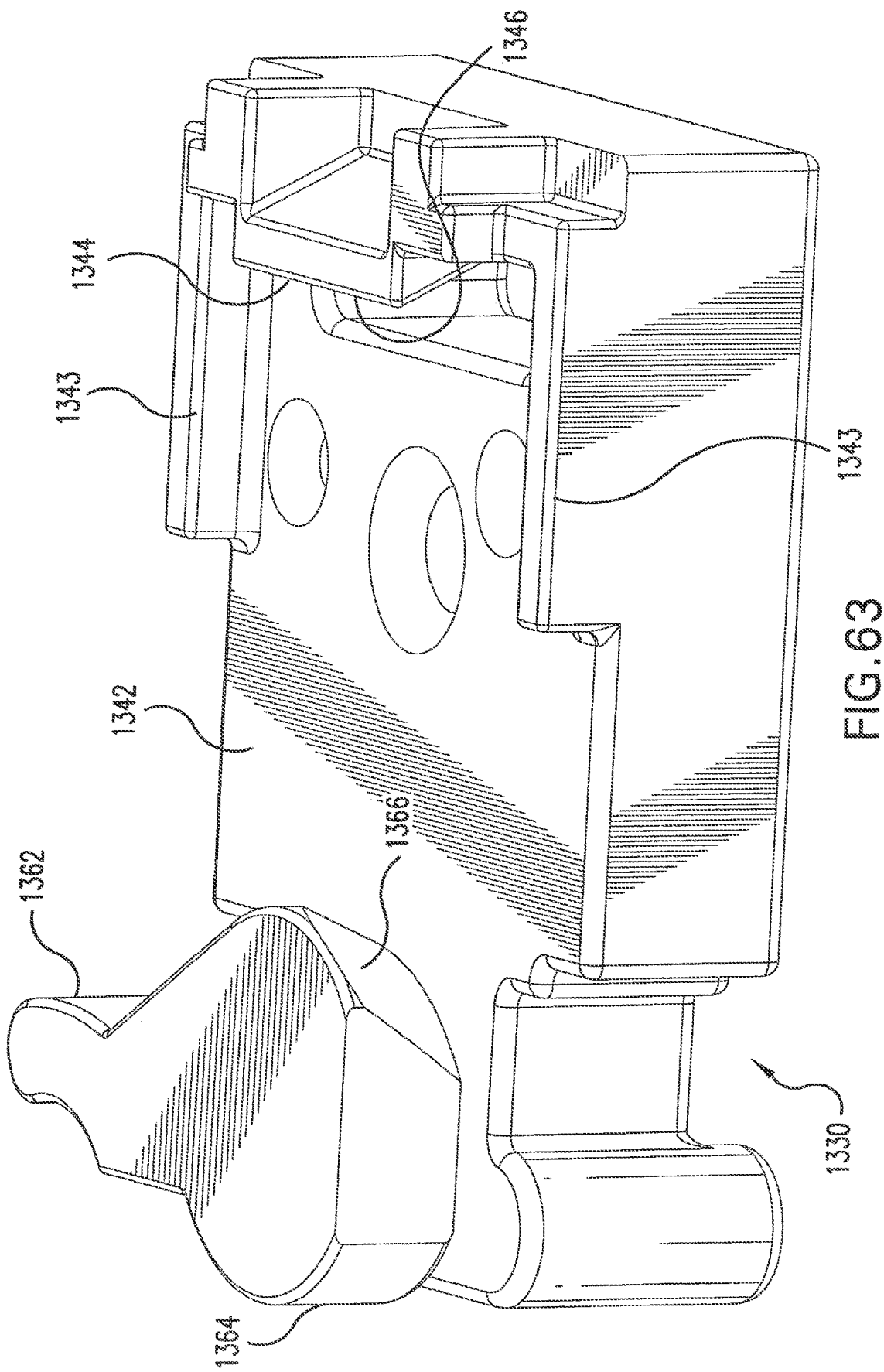
FIG. 63 is a perspective view of a shoe member of FIG. 58.
Figure 64:
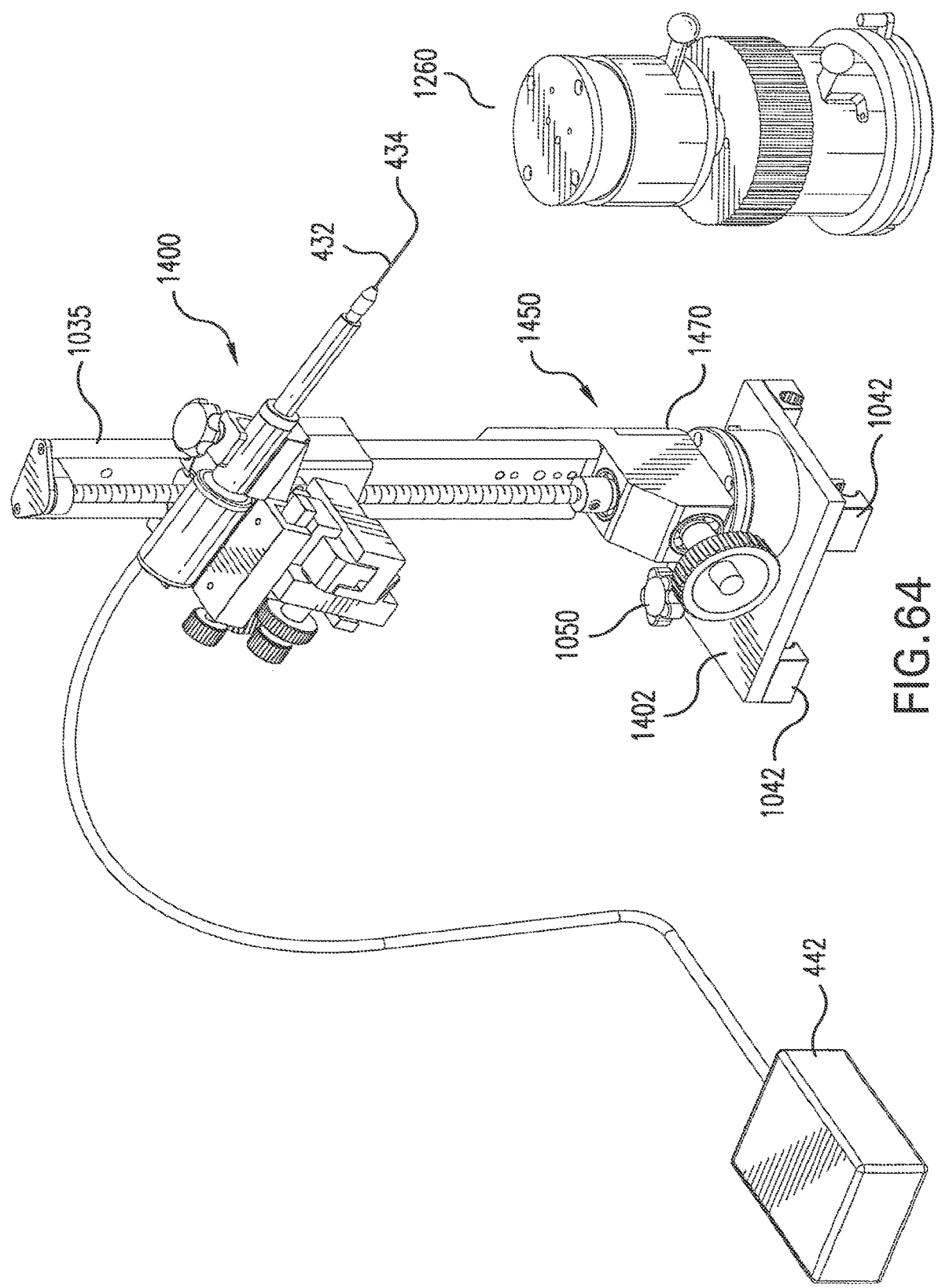
FIG. 64 is a partial system view of the imaging system of the present invention, showing a needle injection assembly, a plunger control unit, and the orientation control mechanism of the present invention.
Figure 65:
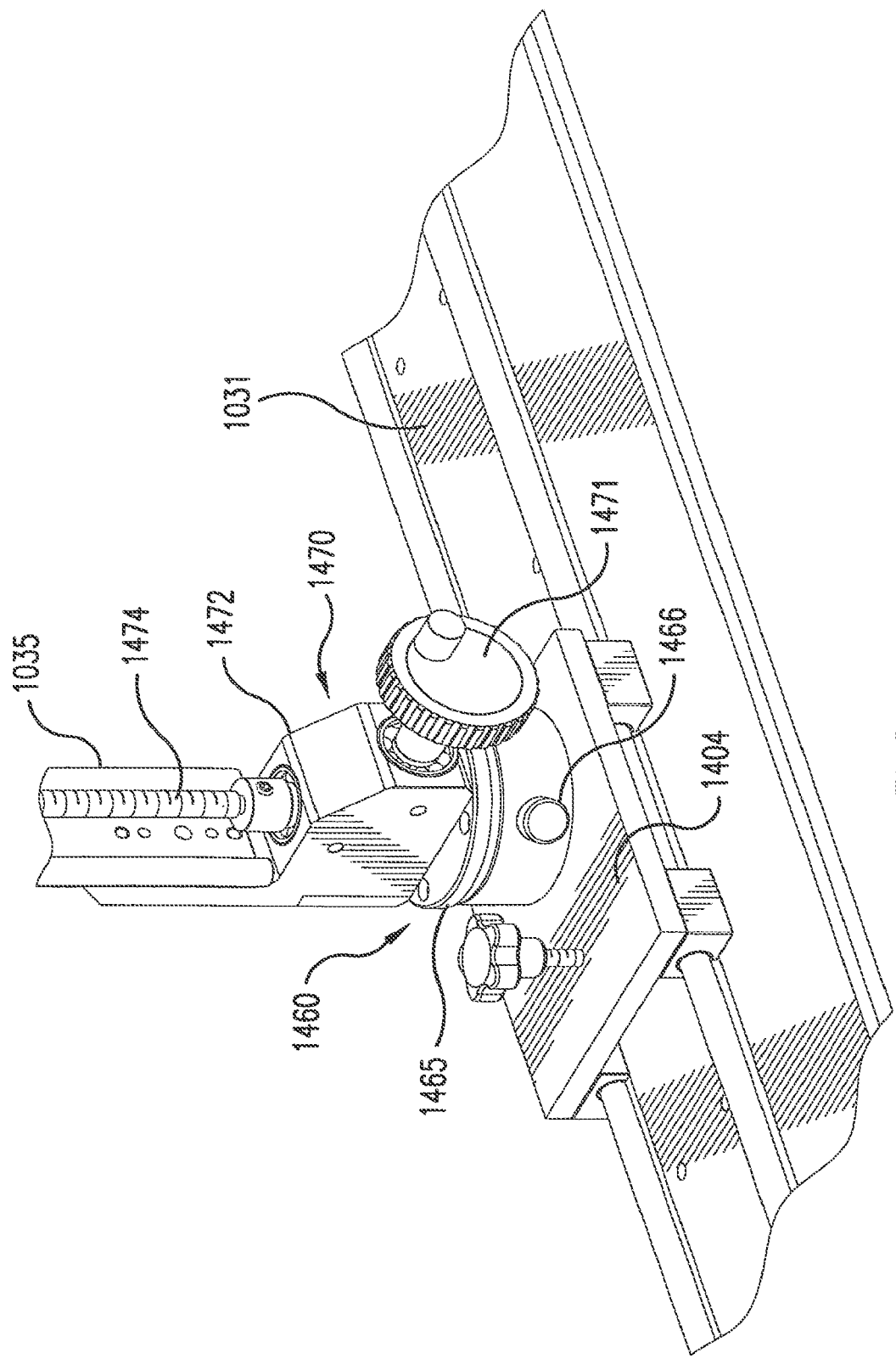
FIG. 65 is a partial perspective view of the needle injection assembly mounted thereon the first rail of the imaging system of the present invention.
Figure 66:
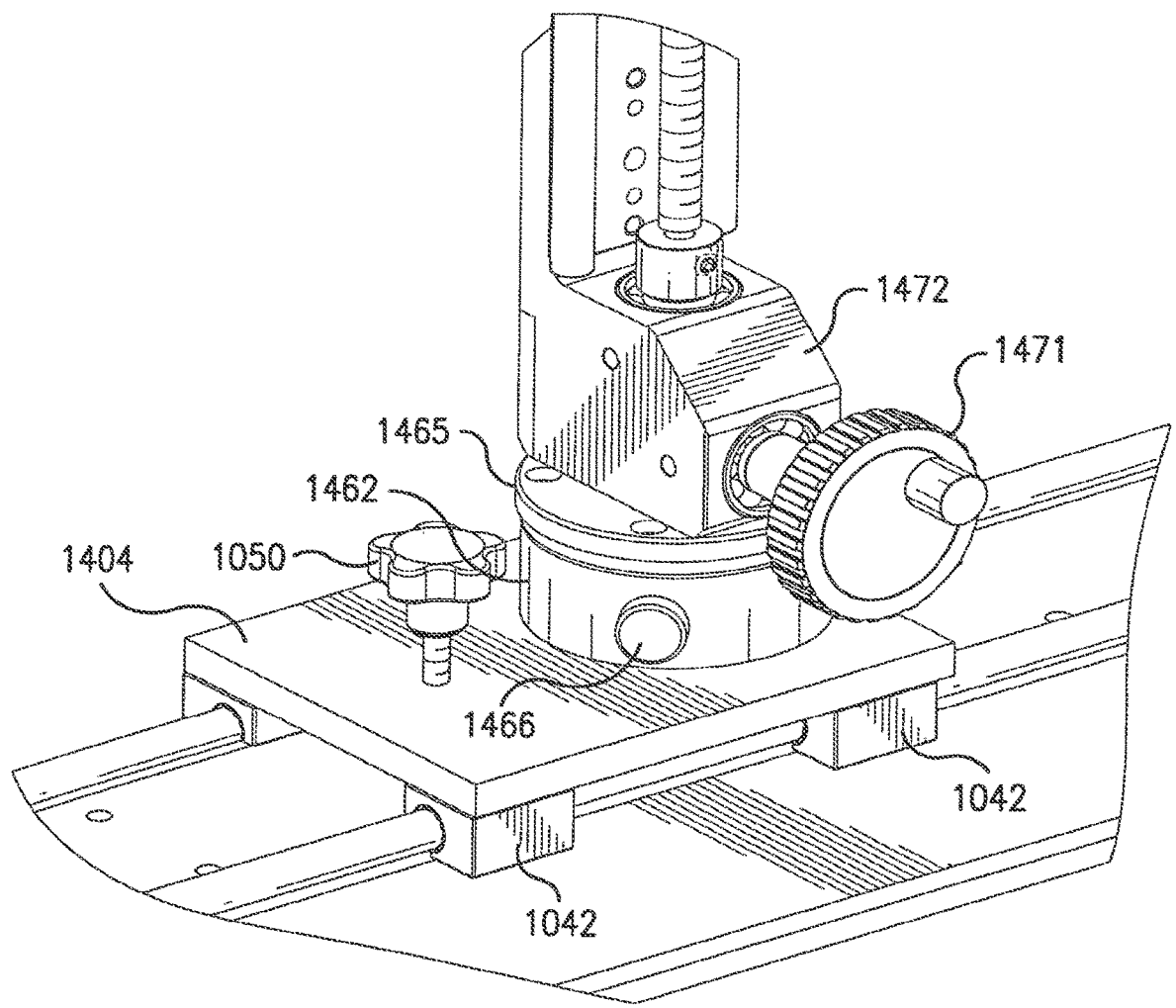
FIG. 66 is a partial semi-transparent perspective view of the rotation adjustment mechanism and a portion of the first height adjustment mechanism of the carriage assembly.
Figure 67:
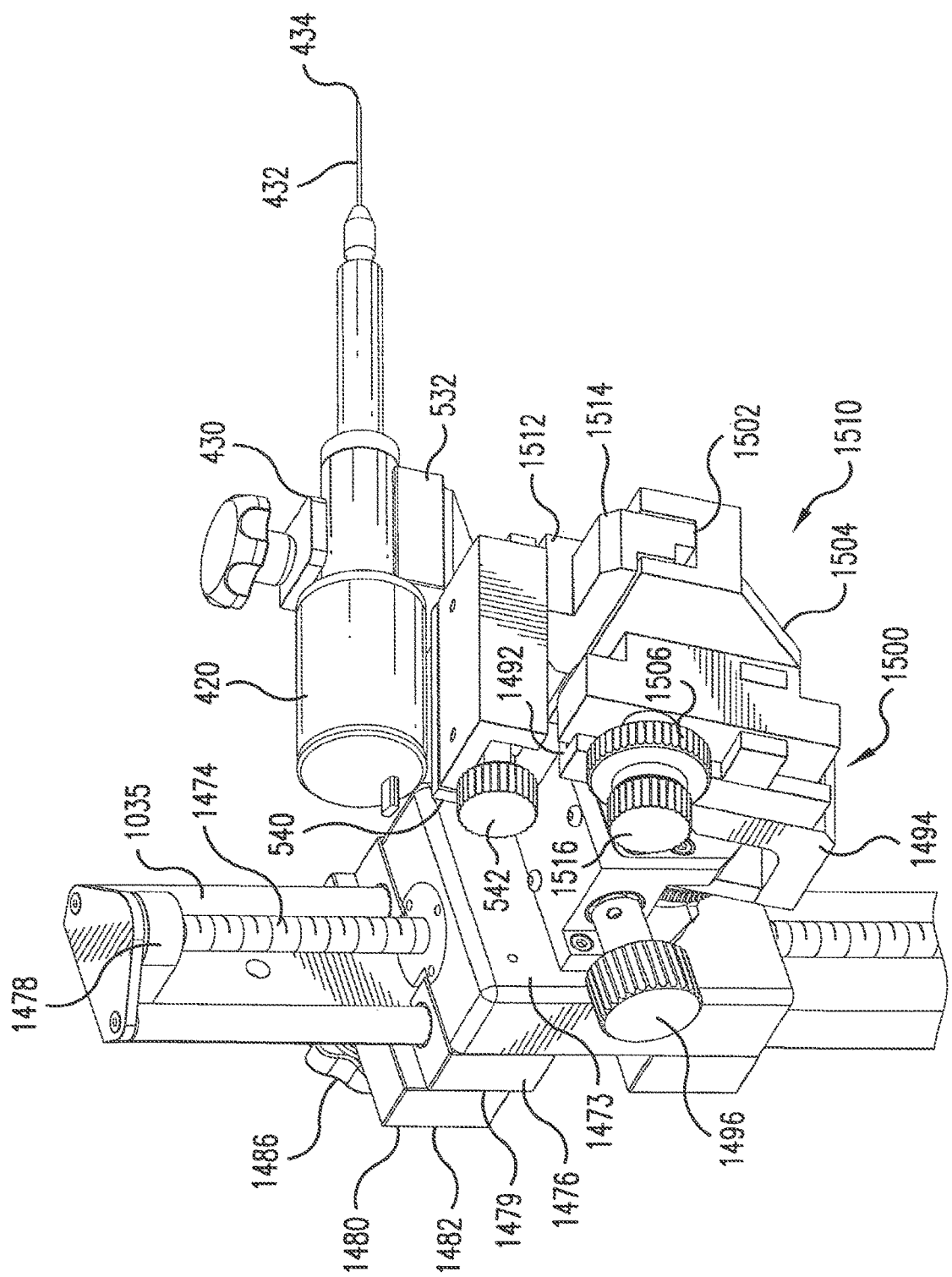
FIG. 67 is a perspective view of a portion of the carriage assembly to which the injection unit is mounted.

In an alternative aspect, shown in FIGS. 61-63, the table/platform member on which the imaged small-animal can be removed by actuating the mount assembly and removing the table/platform member from the orientation control mechanism. In this aspect, a new small-animal, which is positioned on a second table/platform member can be rapidly mounted onto and secured to the orientation control mechanism and the small-animal mount assembly and the imaging assembly can be rapidly repositioned.

If the needle injection assembly is used, the injector unit is filled with the fluid to be injected. In one aspect, the base member of the needle injection assembly is positioned into a proximate procedure position on the third rail. In one example, the movable stop is slid along and then secured onto the third rail at a desired procedure position that is within a few centimetres of the desired final procedure position of the base member. One will appreciate that fine adjustment to the position of the needle of the injection unit can be made through manipulation of the controls of the carriage subassembly. The base member of the needle injection assembly is moved into contact with the movable stop and the controls of the carriage subassembly are manipulated so that the needle can be placed in the desired needle plane, which can also be the set image plane of the scanhead unit. The carriage subassembly can also be manipulated to select the desired angle of penetration of the needle within the desired needle plane.

In another aspect, shown in FIGS. 46, 64-67, the base member of the needle injection assembly is positioned and secured into a proximate procedure position on the first rail such that the small-animal mount assembly is positioned between the needle injection assembly and the imaging assembly. The controls of the carriage subassembly are manipulated so that the needle of the injection unit is positioned in the desired needle plane, which can also be the set image plane of the scanhead unit. The carriage subassembly can also be manipulated to select the desired angle of penetration of the needle within the desired needle plane.

The needle is advanced into the subject small-animal at the needle's insertion point to a desired depth and the sample material is injected either manually or by using the plunge control unit. Typically, confirmation of injected material, such as fluid, can often be seen on the screen of the system as the tissue surrounding the distal end of the needle accommodates the extra volume. The needle can then be withdrawn and the procedure is complete.

Subsequently, the needle injection assembly, the scanhead assembly, and/or the small-animal mount assembly can be selectively moved away from their procedure positions. A new animal can be positioned onto the table member of the small-animal mount assembly and the needle injection assembly, the scanhead assembly, and/or the small-animal mount assembly can be repositioned by relying upon the previous settings of the movable/fixed stops. Alternatively, as noted above, the table/platform member can be removed from the orientation control mechanism and another table platform member, holding a new animal, can be positioned onto the orientation control mechanism the small-animal mount assembly and the needle injection assembly, the scanhead assembly, and/or the small-animal mount assembly can be repositioned readily. One will appreciate that the planes of the scanhead unit and the injector unit will remain co-planer.

It is contemplated that many other procedures can be done using the imaging system 10 of the present invention. The multi-rail design of the imaging system enables an operator to precisely align the needle of the needle injection assembly within the imaging plane of the scanhead unit of the scanhead assembly. The needle injection assembly, the small-animal mount assembly, and the scanhead assembly can then be moved back and forth along their respective rails and be brought back to their original procedure positions without losing the alignment of the image plane or the co-planer alignment between the needle of the injector unit and the image plane of the scanhead unit.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. An imaging system for imaging portions of small-animals, comprising:
   a plurality of elongated rails, comprising a first rail and a second rail, each rail having a longitudinal axis, wherein the second rail is connectable to the first rail and is movable in parallel with the longitudinal axis of the first rail, and wherein the second rail is configured in a direction orthogonal to the longitudinal axis of the first rail;
   a scanhead assembly having a mount, wherein the mount includes a scanhead assembly base member that is attachable to the first rail and is movable in parallel with the longitudinal axis of the first rail; and
   a small-animal mount assembly having a mount subassembly, wherein the mount subassembly includes a mount subassembly base member that is attachable to the second rail, and wherein the mount subassembly base member is movable in parallel with the longitudinal axis of the second rail.

2. The imaging system of claim 1, wherein the first rail is selectively mountable to a planar member, and wherein the planar member substantially underlies at least a portion of the first rail.

3. The imaging system of claim 1, wherein the longitudinal axis of the second rail is positioned substantially perpendicular to the longitudinal axis of the first rail.

4. The imaging system of claim 1, further comprising a needle injection assembly comprising an injection assembly base member that is selectively mountable onto the first rail such that the second rail is positioned between the scanhead assembly base member and the injection assembly base member, the injection assembly base member being constructed and arranged for movement in a linear bidirectional manner along the longitudinal axis of the first rail.

5. The imaging system of claim 1, wherein the elongated rails further comprise:
   a top surface;
   a first edge and an opposed second edge, each edge being substantially parallel to the longitudinal axis of the rail; and
   a raised lip extending therefrom each edge of the rail, substantially perpendicular to the top surface.

6. The imaging system of claim 5, wherein the scanhead assembly base member further comprises:
   a plurality of bearing members mounted thereon a bottom portion of the scanhead assembly base member, wherein at least one of the bearing members is disposed thereon a portion of the raised lip extending from the first edge of the first rail, and at least one of the bearing members is disposed thereon a portion of the raised lip extending from the second edge of the first rail.

7. The imaging system of claim 5, wherein the second rail further comprises a second rail base member, wherein the second rail base member comprises:
   a plurality of bearing members mounted thereon a bottom portion of the second rail base member, wherein at least one of the bearing members is disposed thereon a portion of the raised lip extending from the first edge of the first rail, and at least one of the bearing members is disposed thereon a portion of the raised lip extending from the second edge of the first rail.

8. The imaging system of claim 5, further comprising a needle injection assembly comprising an injection assembly base member that is selectively mountable onto the first rail such that the second rail is positioned between the scanhead assembly base member and the injection assembly base member, the injection assembly base member being constructed and arranged for movement in a linear bidirectional manner along the longitudinal axis of the first rail, wherein the injection assembly base member further comprises:
   a plurality of bearing members mounted thereon a bottom portion of the injection assembly base member, wherein at least one of the hearing members is disposed thereon a portion of the raised lip extending from the first edge of the first rail, and at least one of the bearing members is disposed thereon a portion of the raised lip extending from the second edge of the first rail.

9. The imaging system of claim 1, wherein the scanhead assembly further comprises a scanhead unit having an operative emitting end, the scanhead unit being electrically coupled to a computer.

10. An imaging system for small-animals, comprising:
   a plurality of elongated rails, comprising a first rail and a second rail, each rail having a longitudinal axis, wherein the second rail is attachable to the first rail and is movable in parallel with the longitudinal axis of the first rail, and wherein the second rail is configured to be oriented at an angle between about 30 degrees and about 150 degrees with respect to the longitudinal axis of the first rail;
   a scanhead assembly having a mount, the mount having a scanhead assembly base member that is selectively mountable to the first rail and is selectively movable in a linear bidirectional manner along the longitudinal axis of the first rail and
   a needle injection assembly comprising an injection assembly base member that is selectively mountable onto the first rail such that the second rail is positioned between the scanhead assembly base member and the injection assembly base member, the injection assembly base member being constructed and arranged for movement in a linear bidirectional manner along the longitudinal axis of the first rail.

11. The imaging system of claim 10, further comprising a small-animal mount assembly having a mount subassembly, the mount subassembly having a mount subassembly base member that is selectively mountable to the second rail and is selectively movable in a linear bi-directional manner along the longitudinal axis of the second rail.

12. The imaging system of claim 10, wherein the longitudinal axis of the second rail is positioned substantially perpendicular to the longitudinal axis of the first rail.

13. The imaging system of claim 10, wherein the elongated rails further comprise:
   a top surface;
   a first edge and an opposed second edge, each edge being substantially parallel to the longitudinal axis of the rail; and
   a raised lip extending therefrom each edge of the rail, substantially perpendicular to the top surface.

14. An imaging system for small-animals, comprising:
   a plurality of elongated rails, comprising a first rail and a second rail, each rail having a longitudinal axis, wherein the second rail is attachable to the first rail and movable in parallel with the longitudinal axis of the first rail, and wherein the second rail is configured to be oriented at an angle between about 30 degrees and about 150 degrees with respect to the longitudinal axis of the first rail;
   a scanhead assembly having a mount, the mount having a scanhead assembly base member that is selectively mountable to the first rail and is selectively movable in a linear bidirectional manner along the longitudinal axis of the first rail, wherein the scanhead assembly further comprises a scanhead unit having an operative emitting end, the scanhead unit being electrically coupled to a computer.

15. The imaging system of claim 14, wherein the scanhead assembly further comprises:
   an upright column member extending upwardly away from the scanhead assembly base member;
   a third rail connected to a top of the upright column and extending therefrom coaxial to the longitudinal axis of the column member, the third rail having a distal end;
   a cantilever base member mounted thereon the third rail, the cantilever base member being constructed and arranged for linear bi-directional movement along the longitudinal axis of the third rail, the cantilever base member having a rail lock assembly for selectively securing the cantilever mount member at a desired position in relation to the third rail;
   a fourth rail having a first end and being slidably mounted to the cantilever base member, wherein the fourth rail is constructed and arranged for linear bidirectional movement along its longitudinal axis with respect to the cantilever base member;
   a scanhead unit orientation control mechanism connected to a portion of the first end of the fourth rail and a portion of the scanhead unit, the scanhead unit orientation control mechanism constructed and arranged to position the emitting end of the scanhead unit in a desired image plane.

16. The imaging system of claim 11, wherein the small-animal mount assembly further comprises a small-animal mount sub-assembly for mounting a small animal, the sub-assembly comprising:
   a table member having a top surface, a bottom surface, and defining a table plane;
   a platform member having a top face and an opposed bottom face, the bottom surface of the table member being mounted thereon the top face of the platform member;
   a means for orienting the table member so that the table plane of the table is positioned in a desired table plane; and
   a means for releasably mounting the platform member to the means for orienting the table member.

17. The imaging system of claim 16, wherein the small-animal mount subassembly further comprises:
   a planar platform having an upper surface and a lower surface and defining a first axis parallel to the longitudinal axis of the second rail and a second axis normal to the first axis, the platform further defining a platform plane defined by the first axis and the second axis; and a platform adjustment assembly constructed and arranged for moving the platform in the platform plane, the platform adjustment assembly having a platform base and an adjustable armature, the platform base being connected to a portion of a top surface of the mount subassembly base member and the armature being connected to a portion of an edge of the planar platform.

18. The imaging system of claim 17, wherein the mount subassembly further comprises an orientation control mechanism selectively positionable onto a portion of the upper surface of the planar platform, the orientation control mechanism constructed and arranged for adjusting the table plane of the table member.

* * * * *